(12) United States Patent
Lei et al.

(10) Patent No.: US 10,434,045 B2
(45) Date of Patent: *Oct. 8, 2019

(54) POLYUREA OR POLYURETHANE CAPSULES

(71) Applicant: International Flavors & Fragrances Inc., New York, NY (US)

(72) Inventors: Yabin Lei, Holmdel, NJ (US); Li Xu, Edison, NJ (US); Lewis Michael Popplewell, Morganville, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/045,216

(22) Filed: Jul. 25, 2018

(65) Prior Publication Data

US 2018/0325786 A1 Nov. 15, 2018

Related U.S. Application Data

(63) Continuation of application No. 14/911,433, filed as application No. PCT/US2014/051309 on Aug. 15, 2014, now Pat. No. 10,092,486, which is a continuation-in-part of application No. 13/968,862, filed on Aug. 16, 2013, and a continuation-in-part of application No. 13/969,038, filed on Aug. 16, 2013, now Pat. No. 9,687,424, and a continuation-in-part of application No. 13/967,800, filed on Aug. 15, 2013.

(51) Int. Cl.

| *A61K 8/11* | (2006.01) |
|---|---|
| *A61K 8/04* | (2006.01) |
| *A61K 8/73* | (2006.01) |
| *A61K 8/84* | (2006.01) |
| *A61Q 13/00* | (2006.01) |
| *A61Q 5/00* | (2006.01) |
| *A61Q 5/02* | (2006.01) |
| *A61Q 5/12* | (2006.01) |
| *B01J 13/14* | (2006.01) |
| *B01J 13/16* | (2006.01) |
| *B01J 13/20* | (2006.01) |
| *C11B 9/00* | (2006.01) |
| *C11D 17/00* | (2006.01) |
| *C11D 3/50* | (2006.01) |

(52) U.S. Cl.

CPC ............... *A61K 8/11* (2013.01); *A61K 8/04* (2013.01); *A61K 8/731* (2013.01); *A61K 8/84* (2013.01); *A61Q 5/00* (2013.01); *A61Q 5/02* (2013.01); *A61Q 5/12* (2013.01); *A61Q 13/00* (2013.01); *B01J 13/14* (2013.01); *B01J 13/16* (2013.01); *B01J 13/206* (2013.01); *C11B 9/00* (2013.01); *C11D 3/505* (2013.01); *C11D 17/0039* (2013.01); *A61K 2800/412* (2013.01); *A61K 2800/624* (2013.01); *A61K 2800/805* (2013.01)

(58) Field of Classification Search

CPC . A61K 8/11; A61K 8/04; A61K 8/731; A61K 8/84; A61K 2800/412; A61K 2800/624; A61K 2800/805; A61Q 5/00; A61Q 5/02; A61Q 5/12; A61Q 13/00; B01J 13/14; B01J 13/16; B01J 13/206; C11B 9/00; C11D 3/505; C11D 17/0039

See application file for complete search history.

(56) References Cited

U.S. PATENT DOCUMENTS

| 3,743,601 A | 7/1973 | Rao |
|---|---|---|
| 3,963,680 A | 6/1976 | O'Keefe |
| 4,021,595 A | 5/1977 | Kiritani |
| 4,280,833 A | 7/1981 | Beestman |
| 4,309,213 A | 1/1982 | Graber |
| 4,428,983 A | 1/1984 | Nehen |
| 4,563,212 A | 1/1986 | Becher |
| 4,608,227 A | 8/1986 | Greiner |
| 4,640,709 A | 2/1987 | Beestman |
| 4,785,048 A | 11/1988 | Chao |
| 4,798,862 A | 1/1989 | Gillis |
| 5,164,126 A | 11/1992 | Kalishek |

(Continued)

FOREIGN PATENT DOCUMENTS

| EP | 1693104 A1 | 8/2006 | |
|---|---|---|---|
| EP | 2298439 A2 * | 3/2011 | .............. B01J 13/14 |

(Continued)

OTHER PUBLICATIONS

BASF. "Lupasol® types" (Sep. 2010). Retrieved from the internet <URL: http://www.carytrad.com.tw/chemical/download/basf/08_0806130e_Lupasol%20types.pdf>, pp. 1-10>. (Year: 2010).*
BASF (2010). "Lupasol® types". Retrieved on Jun. 14, 2017. Retrieved from the Internet <URL:http://www.carytrad.com.tw/chemical/download/basf/08_0806130eLupasol%20types.pdf>, pp. 1-10.
Chinese First Office Action dated Jan. 30, 2014 for Application No. CN 201010548980.0.

(Continued)

*Primary Examiner* — Doan T Phan
(74) *Attorney, Agent, or Firm* — Licata & Tyreell P.C.

(57) ABSTRACT

Polyurea capsule compositions. A subset of these compositions contain a plurality of capsules and a capsule formation aid, in which each of the capsules contains a polyurea wall and an oil core; the polyurea wall is formed of a reaction product of a polyisocyanate and a cross-linking agent in the presence of the capsule formation aid; and the oil core contains an active material. The polyisocyanate, cross-linking agent, and capsule formation aids are described herein. Also disclosed are methods of preparing polyurea capsule compositions, as well as consumer products containing one of these compositions.

14 Claims, 8 Drawing Sheets

(56) References Cited

U.S. PATENT DOCUMENTS

| | | | |
|---|---|---|---|
| 5,225,118 A * | 7/1993 | Juang | B01J 13/16 |
| | | | 264/4.33 |
| 5,304,448 A | 4/1994 | Keoshkerian | |
| 5,324,584 A | 6/1994 | Juang | |
| 5,635,211 A | 6/1997 | Nehen | |
| 5,705,174 A | 1/1998 | Benoff | |
| 5,866,153 A | 2/1999 | Hasslin | |
| 5,925,595 A | 7/1999 | Seitz | |
| 6,133,197 A | 10/2000 | Chen | |
| 6,340,653 B1 | 1/2002 | Scher | |
| 6,586,107 B2 | 7/2003 | Klug | |
| 6,797,670 B2 | 9/2004 | Kleban | |
| 6,964,994 B1 | 11/2005 | Antonietti | |
| 7,125,835 B2 | 10/2006 | Bennett | |
| 7,632,789 B2 | 12/2009 | Brain | |
| 8,026,206 B2 | 9/2011 | Sajic | |
| 8,299,011 B2 | 10/2012 | Lei | |
| 2002/0079599 A1 | 6/2002 | Kleban | |
| 2004/0121155 A1 | 6/2004 | Matsunami | |
| 2004/0156742 A1 | 8/2004 | Milan | |
| 2004/0254066 A1 | 12/2004 | Ramarao | |
| 2005/0153135 A1 | 7/2005 | Popplewell | |
| 2005/0153839 A1 | 7/2005 | Tamura | |
| 2005/0161843 A1 * | 7/2005 | Wang | B01J 13/04 |
| | | | 264/4.1 |
| 2005/0271735 A1 | 12/2005 | Stover | |
| 2007/0042182 A1 | 2/2007 | Markus | |
| 2007/0138672 A1 | 6/2007 | Lee | |
| 2007/0202063 A1 | 8/2007 | Dihora | |
| 2008/0103265 A1 | 5/2008 | Schocker | |
| 2008/0131695 A1 | 6/2008 | Aouad | |
| 2008/0187596 A1 | 8/2008 | Dihora | |
| 2008/0200363 A1 | 8/2008 | Smets | |
| 2008/0206291 A1 | 8/2008 | Ouali | |
| 2009/0053161 A1 | 2/2009 | Nguyen | |
| 2009/0259300 A1 | 10/2009 | Dorogy | |
| 2010/0009893 A1 | 1/2010 | Cavin | |
| 2010/0086575 A1 | 4/2010 | Dihora | |
| 2010/0119679 A1 | 5/2010 | Dihora | |
| 2011/0077188 A1 | 3/2011 | Ouali | |
| 2011/0077375 A1 | 3/2011 | Kulke | |
| 2011/0230390 A1 | 9/2011 | Ouali | |
| 2011/0245141 A1 | 10/2011 | Gizaw | |
| 2012/0016139 A1 | 1/2012 | Screen | |
| 2012/0148644 A1 * | 6/2012 | Popplewell | A61K 8/11 |
| | | | 424/401 |
| 2013/0109569 A1 | 5/2013 | Dave | |
| 2013/0330292 A1 | 12/2013 | Lei | |
| 2013/0337023 A1 | 12/2013 | Lei | |
| 2014/0017287 A1 | 1/2014 | Lei | |

FOREIGN PATENT DOCUMENTS

| | | | |
|---|---|---|---|
| JP | 5068970 A | 6/1975 | |
| WO | 2004098767 A1 | 11/2004 | |
| WO | 2006006003 A1 | 1/2006 | |
| WO | 2007137441 A1 | 12/2007 | |
| WO | 2008031241 A1 | 3/2008 | |
| WO | 2009091726 A1 | 7/2009 | |
| WO | 2009103615 A1 | 8/2009 | |
| WO | 2011104893 A1 | 9/2011 | |
| WO | 2011161265 A2 | 12/2011 | |
| WO | WO-2011154893 A1 * | 12/2011 | B01J 13/16 |
| WO | 2012107323 A1 | 8/2012 | |
| WO | 2013000587 A1 | 1/2013 | |
| WO | 2013059167 A2 | 4/2013 | |
| WO | 2013092958 A1 | 6/2013 | |
| WO | WO-2013092375 A1 * | 6/2013 | C11D 3/505 |
| WO | WO-2013092958 A1 * | 6/2013 | A61K 8/84 |

OTHER PUBLICATIONS

Dow Plastics—"PAPI135". Retrieved on Jan. 3, 2017. Retrieved from the internet <URL:http://msdssearch.dow.com/PublishedliteratureDOWCOM/dh_003f/0901b8038003f163.pdf>.

EP Extended Search Report dated Mar. 31, 2017 from 14836347.9 filed Aug. 15, 2014.

International Preliminary Report on Patentability in PCT/US2014/051309 dated Feb. 16, 2016.

International Search Report and Written Opinion in PCT/US2014/051309 dated Nov. 4, 2014.

Office Communication dated Oct. 18, 2011 from U.S. Appl. No. 12/562,578, filed Sep. 18, 2009.

Office Communication dated Aug. 21, 2012 from U.S. Appl. No. 13/163,320, filed Jun. 17, 2011.

Office Communication dated Nov. 21, 2012 from U.S. Appl. No. 13/163,320, filed Jun. 17, 2011.

Office Communication dated Jan. 4, 2017 from U.S. Appl. No. 15/047,364, filed Feb. 18, 2016.

Office Communication dated Jan. 4, 2017 from U.S. Appl. No. 15/047,590, filed Feb. 18, 2016.

* cited by examiner

POLYUREA OR POLYURETHANE CAPSULES

CROSS-REFERENCE TO RELATED APPLICATIONS

This application is a continuation of U.S. application Ser. No. 14/911,433 filed Feb. 10, 2016, which is a national phase entry under 35 USC 371 for International Application No. PCT/US2014/051309 filed Aug. 15, 2014. The international application is a continuation-in-part of three US patent applications: U.S. application Ser. No. 13/967,800 filed Aug. 15, 2013; U.S. application Ser. No. 13/968,862 filed Aug. 16, 2013; and U.S. application Ser. No. 13/969,038 filed Aug. 16, 2013, now issued as U.S. Pat. No. 9,687,424. The contents of the above-mentioned applications are incorporated herein by reference in their entirety.

BACKGROUND

Nano- or micro-encapsulation is used in a variety of different applications where there is a need to deliver, apply, or release an active material including a fragrance, flavor, and malodor counteraction agent to a target area in a time-delayed or controlled manner. Various techniques for preparing capsules are known in the art and are used, depending on the contents to be encapsulated, the environment in which the capsules should retain their integrity and the desired release mechanism.

Interfacial polycondensation is a known technique for preparing capsules and versatile capsule wall materials are used including polyureas and polyurethanes (WO 2011/154893, WO 2012/107323, US 2011/0077188, U.S. Pat. Nos. 5,635,211, 6,586,107, and 6,797,670). Such wall materials are produced by having a first phase which is water-immiscible and includes a polyfunctional isocyanate, i.e., a polyisocyanate having two or more isocyanate groups, and a second aqueous phase which includes (i) a polyfunctional alcohol (i.e., a polyol) having two or more —OH groups for obtaining a polyurethane capsule wall, or (ii) a polyfunctional amine (i.e., a polyamine) having two or more —$NH_2$ and/or —NH groups for obtaining a polyurea capsule wall.

If the active material to be encapsulated is hydrophobic, it will be included in the water-immiscible phase, thereafter the two phases are mixed by high shear mixing to form an oil-in-water emulsion. In this emulsion, the polycondensation reaction will take place. Thus, the small droplets of the water-immiscible phase will be surrounded by the capsule wall formed by polycondensation of the isocyanate and the polyalcohol or polyamine as starting materials. Conversely, if the material to be encapsulated is hydrophilic, it will be included in the aqueous phase and the mixture of the two phases converted into a water-in-oil emulsion. The polycondensation reaction will then form capsule walls surrounding the droplets of water-miscible phase. Suitable emulsifiers are often utilized to aid in the preparation and stabilization of the emulsion.

Suitable raw materials and processes for preparing capsules by polycondensation are described in U.S. Pat. No. 4,640,709 and the literature described therein. As is exemplified therein, and also in U.S. Pat. No. 6,133,197, polyurea and polyurethane capsules are often used for rugged applications, such as for encapsulation of agrochemicals, e.g., herbicides and pesticides, where slow time-release is desired to set the agents free. For such applications, the capsules also require a relatively high mechanical strength. For the polycondensation reaction, suitable diisocyanate and symmetrical triisocyanate starting materials are disclosed in the prior art.

WO 2011/154893 discloses a process for the preparation of capsules, which includes mixing at least one aliphatic polyisocyanate and of at least one aromatic polyisocyanate, wherein the molar ratio between the two polyisocyanates is between 75:25 and 20:80.

WO 2013/000587 discloses a process for the preparation of polyurea capsules, which includes dissolving at least one polyisocyanate having at least two isocyanate functional groups, in a perfume to form a solution; adding to the solution an aqueous solution of an emulsifier or of a colloidal stabilizer; and adding to the mixture to 3,5-diamino-1,2,4-triazole to form a polyurea wall.

U.S. Pat. No. 5,304,448 describes an encapsulated toner composition using reaction of amino acids and polyisocyanates.

Known polyurea or polyurethane capsules face various issues, e.g., low olfactory intensity, low stability, and high toxicity. Their deposition to target surfaces is also problematic.

There is a need to develop a safe, stable, and high efficient capsules for use in laundry, washing, cleaning, surface care and personal and skin care. For such applications quicker and easier release and/or less mechanical strength are often desirable. Also, it would be desirable to more precisely influence the capsule wall permeability and other capsule wall properties to achieve the desired release profile and consumer benefits.

SUMMARY OF THE INVENTION

This invention is based on the discovery that certain capsule compositions possess unexpected desirable properties including high perceived olfactory intensity, prolonged stability, low toxicity, and improved deposition.

Accordingly, one aspect of this invention relates to a method for preparing a polyurea or polyurethane capsule composition. The method includes the steps of: (a) preparing an oil phase having an active material and a polyisocyanate; (b) preparing an aqueous phase having a cross-linking agent that is a multi-functional amine or multi-functional alcohol; (c) emulsifying the oil phase into the aqueous phase to form an active emulsion; (d) causing formation of polyurea or polyurethane capsules in the active emulsion to obtain a capsule slurry; (e) curing the capsule slurry; and (f) purifying the capsule slurry by washing with water, diafiltration, or centrifugation. Purification is usually carried out after the curing step.

Another aspect of this invention relates to a method for preparing a polyurea or polyurethane capsule composition. This method includes the steps of: (a) providing a capsule slurry containing polyurea or polyurethane capsules and water; and (b) purifying the capsule slurry by washing with water, diafiltration, or centrifugation.

In the two above methods, preferably, the capsule slurry is purified by washing with water until a neutral pH in the capsule slurry is achieved. A salt can be added to the capsule slurry prior to washing it.

Still another aspect of this invention relates to polyurea or polyurethane capsule compositions prepared by any method described above. These capsule compositions can further contain a surfactant, polymer, deposition aid, alcohol (e.g., ethanol), or any combination thereof. The polymer is an anionic, cationic, nonionic or amphoteric polymer.

In any of the above capsule compositions, an active material is encapsulated in a polyurea or polyurethane capsule wall. The active material can be a fragrance, flavor, malodor counteracting agent, or combination thereof.

Also within the scope of this invention are polyurea and polyurethane capsule compositions that have a plurality of polyurea or polyurethane capsules and a capsule formation aid. Each of the capsules contains a polyurea or polyurethane wall and an oil core, in which the polyurea or polyurethane wall is formed of a reaction product of a polyisocyanate and a cross-linking agent in the presence of the capsule formation aid; and the oil core contains an active material (e.g., a fragrance, flavor, malodor counteracting agent, and combination thereof). The cross-linking agent includes, but are not limited to, multi-functional alcohols (e.g., polyols), multi-functional amines (e.g., polyamines), and any combination thereof. Exemplary multi-functional alcohols are pentaerythritol, and dipentaerythritol; glycerol and polyglycerol; trimethylolpropane, neopentyl glycol, and sorbitol. Exemplary multi-functional amines are ethylene-diamine, 1,3-diaminopropane, 1,4-diamino-butane, diethyl-ene-triamine, pentaethylenehexamine, hexanethylene diamine, bis(3-aminopropyl)amine, bis(hexanethylene)triamine, tris(2-aminoethyl)amine, triethylene-tetramine, N,N'-bis(3-aminopropyl)-1,3-propanediamine, tetraethylenepentamine, pentaethylenehexamine, branched polyethylenimine, chitosan, nisin, gelatin, 1,3-diamino-guanidine, 1,1-di-methylbiguanide, guanidine, arginine, lysine, ornithine, or a combination thereof. In some embodiments, compounds having one or more —OH groups and one or more —NH— or $NH_2$ groups are used as the cross-linking agent.

Branched polyethylenimines useful as cross-linking agents typically have a molecular weight of 200 to 2,000,000 Da (e.g., 800 to 2,000,000 Da, 2,000 to 1,000,000, 10,000 to 2,000,000 Da, and 20,000 to 100,000 Da).

Suitable capsule formation aids include polyvinyl alcohols, polystyrene sulfonates, carboxymethyl celluloses, naphthalene sulfonate, polyvinylpyrrolidones, copolymers of vinyl pyrrolidone and quaternized dimethylaminoethyl methacrylate, or any mixture thereof. Typical examples of the mixture are mixtures of carboxymethyl celluloses and polystyrene sulfonates, mixtures of carboxymethyl cellulose and polyvinylpyrrolidones, and mixtures of polyvinylpyrrolidones and copolymers of vinyl pyrrolidones and quaternized dimethylaminoethyl methacrylates.

Polyisocyanates useful in this invention can be aromatic polyisocyanates, aliphatic polyisocyanates, or any combination thereof. Suitable aromatic polyisocyanates include those containing a phenyl, tolyl, xylyl, naphthyl, or diphenyl moiety, or a combination thereof, such as a polyisocyanurate of toluene diisocyanate, a trimethylol propane-adduct of toluene diisocyanate, and a trimethylol propane-adduct of xylylene diisocyanate. Suitable aliphatic polyisocyanates include a trimer of hexamethylene diisocyanate, a trimer of isophorone diisocyanate, a biuret of hexamethylene diisocyanate, or a combination thereof. In certain embodiments, aliphatic polyisocyanates are used. In other embodiments, some capsule compositions are prepared without using any aromatic polyisocyanate.

In addition to fragrances, flavors, and malodor counteracting agents contained in the oil core, core modifiers are usually included.

Deposition aids, typically an anionic, cationic, nonionic, or zwitterionic polymer, can be also included in any capsule composition described above.

Still within the scope of this invention is a method of preparing polyurea or polyurethane capsule compositions. The method includes the steps of: (a) preparing an oil phase comprising an active material and a polyisocyanate; (b) preparing a dispersant solution containing a capsule formation aid; (c) emulsifying the oil phase into the dispersant solution to form an active emulsion; (d) adding a cross-linking agent to the active emulsion to form a capsule slurry; and (e) curing the capsule slurry, thereby obtaining a polyurea or polyurethane capsule composition of this invention. The polyisocyanates, active materials, and cross-linking agents are described above. They will be further elaborated below, as well as capsule formation aids.

The cross-linking agent can be added at 0-45° C. (e.g., 20-40° C. and 25-35° C.). The capsule slurry can be cured at 55-135° C. (e.g., 65-135° C., 75-135° C., 85-135° C., and 95-135° C.).

A base is optionally added into the active emulsion, especially when a salt (e.g., guanidine carbonate, 1,3-di-aminoguanidine monohydrochloride, 1,1-dimethylbiguanide hydrochloride, and arginine monohydrochloride) is used as a cross-linking agent. Typical bases include a metal carbonate (e.g., sodium carbonate, cesium carbonate, potassium carbonate, and lithium carbonate), a metal bicarbonate (e.g., sodium bicarbonate and potassium bicarbonate), and a metal hydroxide (e.g., sodium hydroxide, potassium hydroxide, lithium hydroxide, and magnesium hydroxide). These bases can neutralize salt-containing cross-linking agents and also catalyze the reaction between a polyisocyanate and a cross-linking agent. Sometime, one or more additional catalysts can be added, e.g., 1,4-diazabicyclo[2.2.2]octane ("DABCO").

In some embodiments, a core modifier is added to the oil phase before emulsifying. In other embodiments, a deposition aid is added before or after curing the capsule slurry. Both the core modifier and the deposition aid are described above.

The above method can further include purifying the cured capsules by diafiltration, centrifugation, or washing with water until a neutral pH is achieved. Before washing with water, a salt is optionally added to the cured capsule slurry to improve the washing efficiency.

Also provided in this disclosure are polyurea or polyurethane capsule compositions prepared by any one of the methods described above.

A consumer product containing any above capsule composition is also provided. Exemplary consumer products include a shampoo, a hair conditioner, a soap, a body wash, a cosmetic preparation, a body liquid detergent, an all-purpose cleaner, a fabric softener or refresher, an ironing water, a fabric detergent, a softener, a drier sheet, a fine fragrance, an Eau De Toilette product, a deodorant, an roll-on product, and an aerosol product.

The details of one or more embodiments of the invention are set forth in the description below. Other features, objects, and advantages of the invention will be apparent from the description and the claims.

DETAILED DESCRIPTION OF THE INVENTION

Figure 1A:
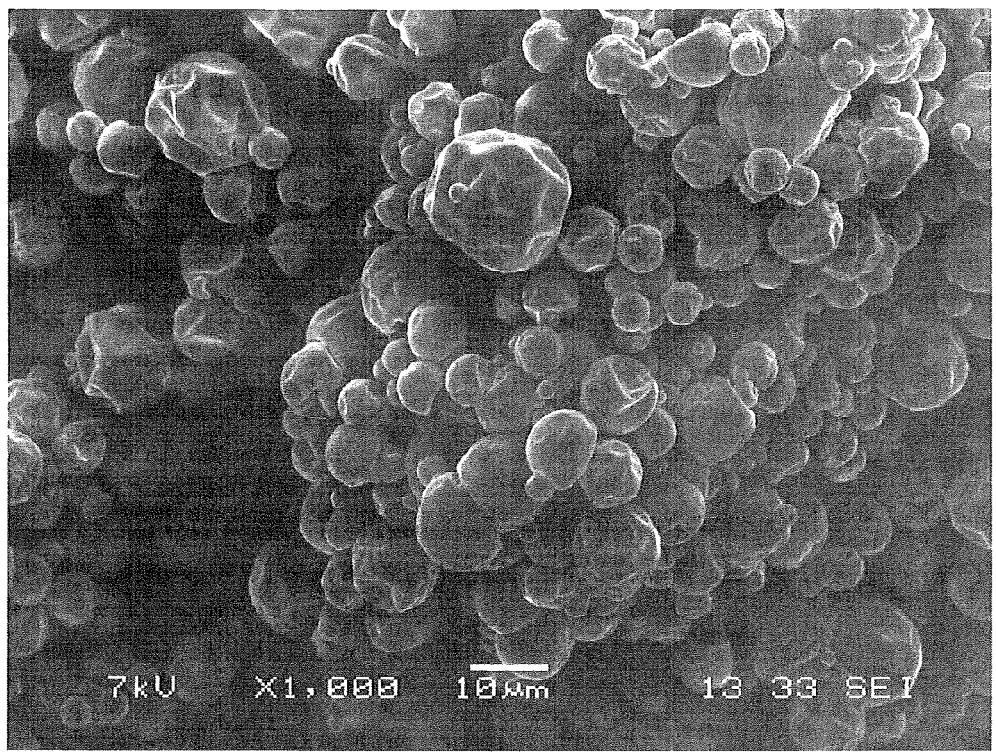
FIG. 1A shows a scanning electron microscope (SEM) image of capsules prepared in accordance with the present invention.

It has been found that polyurea/polyurethane capsule compositions prepared with a polyisocyanate and a cross-linking agent are very suitable for carrying various kinds of hydrophobic or hydrophilic active materials of use in products intended for application to animate and inanimate surfaces.

Polyurea/polyurethane capsule compositions of this invention are useful in a wide range of consumer applications, e.g., personal care products including shampoo, hair conditioners, personal wash such as soaps, body wash, personal cleaners and sanitizers, fabric care such as fabric refreshers, softeners and dryer sheets, ironing water, industrial cleaners, liquid and powder detergent, rinse conditioners, fine fragrances, an Eau De Toilette product, a deodorant, an roll-on product, or an aerosol product.

Specifically, the capsule compositions of this invention are well-suited for use in hydroalcoholic medium such as fine fragrance and for use in leave-on personal care applications. Moreover, the inclusion of a capsule formation aid in the capsule wall-forming reaction provides capsules with excellent storage stability and retention of an encapsulated fragrance.

Certain capsules prepared from anionic capsule formation aids have a positive zeta-potential of 5 mV to 200 mV (e.g., 20-80 mV), which provides strong affinity to specific animate and inanimate surfaces.

The capsule compositions of this invention can be prepared by reacting a polyisocyanate with a cross-linking agent in the presence of a capsule formation aid (e.g., a dispersant) and/or a catalyst (e.g., a base) so that an active material is encapsulated in an oil core by a capsule wall. The oil core optionally contains a core modifier.

These capsule-forming materials are described in detail below.

Polyisocyanate. The polyurea or polyurethane capsules of this invention are prepared using one or more polyisocyanates. Each of them has two or more isocyanate groups, i.e., O=C=N—, wherein said polyisocyanate can be aromatic, aliphatic, linear, branched, or cyclic. In certain embodiments, the polyisocyanate contains, on average, 2 to 4 —N=C=O groups. In particular embodiments, the polyisocyanate contains at least three isocyanate functional groups. In certain embodiments, the polyisocyanate is water insoluble.

In particular embodiments, the polyisocyanate used in this invention is an aromatic polyisocyanate. Desirably, the aromatic polyisocyanate includes a phenyl, tolyl, xylyl, naphthyl or diphenyl moiety as the aromatic component. In certain embodiments, the aromatic polyisocyanate is a polyisocyanurate of toluene diisocyanate, a trimethylol propane-adduct of toluene diisocyanate or a trimethylol propane-adduct of xylylene diisocyanate.

In other embodiments, the polyisocyanate is an aliphatic polyisocyanate. In certain embodiments, the aliphatic polyisocyanate is a trimer of hexamethylene diisocyanate, a trimer of isophorone diisocyanate or a biuret of hexamethylene diisocyanate. Exemplary aliphatic polyisocyanates include those commercially available, e.g., BAYHYDUR N304 and BAYHYDUR N305, which are aliphatic water-dispersible polyisocyanates based on hexamethylene diisocyanate; DESMODUR N3600, DESMODUR N3700, and DESMODUR N3900, which are low viscosity, polyfunctional aliphatic polyisocyanates based on hexamethylene diisocyanate; and DESMODUR 3600 and DESMODUR N100 which are aliphatic polyisocyanates based on hexamethylene diisocyanate, each of which is available from Bayer Corporation, Pittsburgh, Pa.).

One class of suitable polyisocyanates are aromatic polyisocyanates that have the generic structure below, and its structural isomers

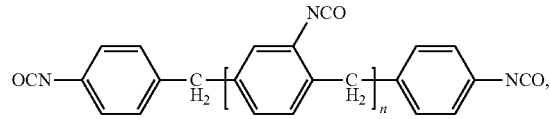

wherein n can vary from zero to a desired number depending on the type of polyamine or polyol used. For the purpose of this invention, the number of n is limited to less than 6. The starting polyisocyanate may also be a mixture of polyisocyanates where the value of n can vary from 0 to 6. In the case where the starting polyisocyanate is a mixture of various polyisocyanates, the average value of n preferably falls in between 0.5 and 1.5.

Specific examples of wall monomer isocyanates include, for example, 1,5-naphthylene diisocyanate, 4,4'-diphenylmethane diisocyanate (MOI), hydrogenated MDI (H12MDI), xylylene diisocyanate (XDI), tetramethylxylol diisocyanate (TMXDI), 4,4'-diphenyldimethylmethane diisocyanate, di- and tetraalkyldiphenylmethane diisocyanate, 4,4'-dibenzyl diisocyanate, 1,3-phenylene diisocyanate, 1,4-phenylene diisocyanate, the isomers of tolylene diisocyanate (TDI), optionally in a mixture, 1-methyl-2,4-diisocyanato-cyclohexane, 1,6-diisocyanato-2,2,4-trimethylhexane, 1,6-diisocyanato-2,4,4-trimethylhexane, 1-isocyanatomethyl-3- isocyanato-1,5,5-trimethylcyclohexane, chlorinated and brominated diisocyanates, phosphorus-containing diisocyanates, 4,4'-diisocyanatophenylperfluoroethane, tetramethoxybutane 1,4-diisocyanate, butane 1,4-diisocyanate, hexane 1,6-diisocyanate (HDI), dicyclohexylmethane diisocyanate, cyclohexane 1,4-diisocyanate, ethylene diisocyanate, phthalic acid bisisocyanatoethyl ester, also polyisocyanates with reactive halogen atoms, such as 1-chloromethylphenyl 2,4-diisocyanate, 1-bromomethylphenyl 2,6-diisocyanate, 3,3-bischloromethyl ether 4,4'-diphenyldiisocyanate. Sulfur-containing polyisocyanates are obtained, for example, by reacting 2 mol of hexamethylene diisocyanate with 1 mol of thiodiglycol or dihydroxydihexyl sulfide. Further suitable diisocyanates are trimethylhexamethylene diisocyanate, 1,4-diisocyanatobutane, 1,2-diisocyanatododecane and dimer fatty acid diisocyanate.

Other suitable commercially-available polyisocyanates include LUPRANATE M20 (BASF), where the average n is 0.7; PAPI 27 (Dow Chemical) where the average n is 0.7; MONDUR MR (Bayer) where the average n is 0.8; MONDUR MR Light (Bayer) where the average n is 0.8; MONDUR 489 (Bayer) where the average n is 1.0; poly[(phenylisocyanate)-co-formaldehyde] (Aldrich Chemical, Milwaukee, Wis.), other isocyanate monomers such as DESMODUR N3200 (Bayer), and TAKENATE D110-N (Mitsui Chemicals corporation, Rye Brook, N.Y.).

In particular embodiments, the polyisocyanate of the invention has the structure:

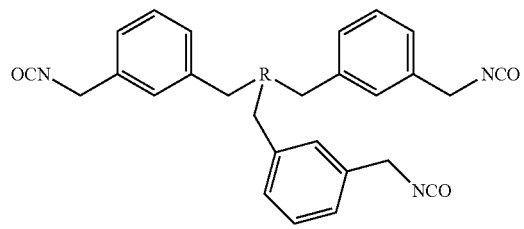

or its structural isomer. Representative polyisocyanates having this structure are TAKENATE D-110N (Mitsui), DESMODUR L75 (Bayer), and DESMODUR IL (Bayer).

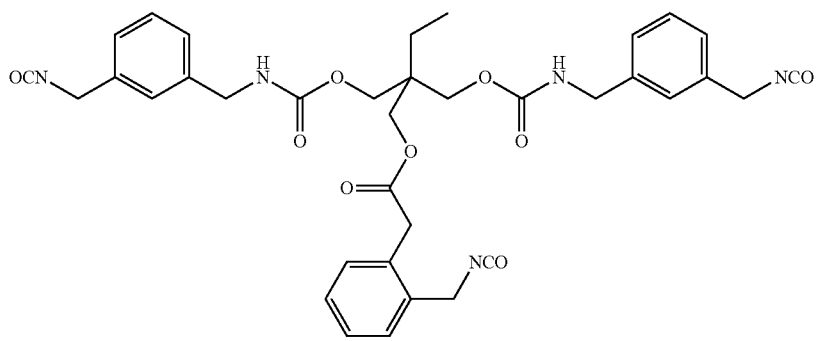

TAKENATE D-110N

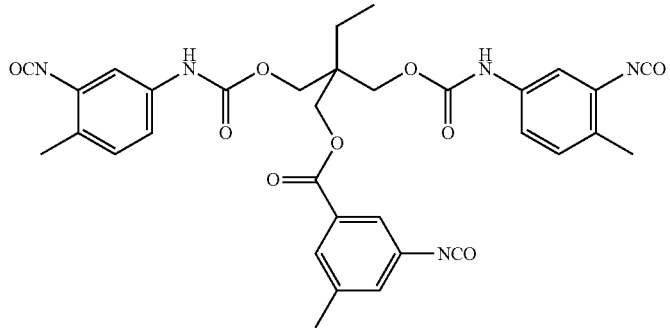

DESMODUR L75

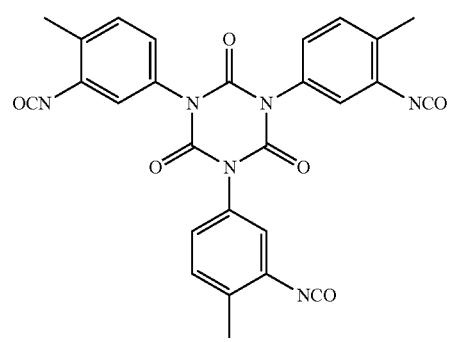

DESMODUR IL

In some embodiments, the polyisocyanate used in the preparation of the polyurea or polyurethane capsules of this invention is a single polyisocyanate. In other embodiments the polyisocyanate is a mixture of polyisocyanates. In some embodiments, the mixture of polyisocyanates includes an aliphatic polyisocyanate and an aromatic polyisocyanate. In particular embodiments, the mixture of polyisocyanates is a biuret of hexamethylene diisocyanate and a trimethylol propane-adduct of xylylene diisocyanate. In certain embodiments, the polyisocyanate is an aliphatic isocyanate or a mixture of aliphatic isocyanate, free of any aromatic isocyanate. In other words, in these embodiments, no aromatic isocyanate is used to prepare the polyurea compositions of this invention.

The average molecular weight of certain polyisocyanates useful in this invention varies from 250 to 1000 Da and preferable from 275 to 500 Da. In general, the range of the polyisocyanate concentration in the composition of this invention varies from 0.1% to 10%, preferably from 0.1% to 8%, more preferably from 0.2 to 5%, and even more preferably from 1.5% to 3.5%, all based on the total capsule composition.

More examples of suitable isocyanates can be found in PCT 2004/054362; EP 0 148149; EP 0 017 409 B1; U.S. Pat. Nos. 4,417,916, 4,124,526, 5,583,090, 6,566,306, 6,730,635, PCT 90/08468, PCT WO 92/13450, U.S. Pat. Nos. 4,681,806, 4,285,720 and 6,340,653.

Cross-Linking Agent. Cross-linking agents are used to form the capsule walls. These agents in general contains multiple (i.e., two or more) function groups (e.g., —NH—, —NH$_2$ and —OH) that can react with polyisocyanates to form polyureas or polyurethanes. Examples include multi-functional amines (e.g., polyamines) and multi-functional alcohols (e.g., polyols).

Suitable polyamines contain two or more amine groups including —NH$_2$ and —R*NH, R* being substituted and unsubstituted $C_1$-$C_{20}$ alkyl, $C_1$-$C_{20}$ heteroalkyl, $C_1$-$C_{20}$ cycloalkyl, 3- to 8-membered heterocycloalkyl, aryl, and heteroaryl.

Two classes of such polyamines include polyalkylene polyamines having the following structures:

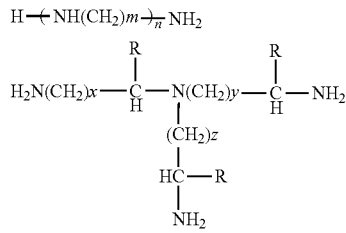

In which R is hydrogen or —CH$_3$; and m, n, x, y, and z each are integers from 0-2000 (e.g., 1, 2, 3, 4, and 5). Examples include ethylene diamine, 1,3-diaminepropane, diethylene triamine, triethylene tetramine, 1,4-diaminobutane, hexanethylene diamine, hexamethylene diamine, pentaethylenehexamine, and the like.

Another class of polyamines are polyalkylene polyamines of the type:

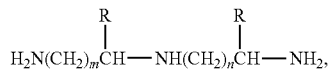

where R equals hydrogen or —CH$_3$, m is 1-5 and n is 1-5, e.g., diethylene triamine, triethylene tetraamine and the like. Exemplary amines of this type also include diethylenetriamine, bis(3-aminopropyl)amine, bis(hexanethylene)triamine.

Another class of amine that can be used in the invention is polyetheramines. They contain primary amino groups attached to the end of a polyether backbone. The polyether backbone is normally based on either propylene oxide (PO), ethylene oxide (EO), or mixed PO/EO. The ether amine can be monoamine, diamine, or triamine, based on this core structure. An example is:

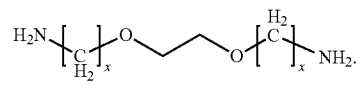

Exemplary polyetheramines include 2,2'-ethylenedioxy)bis (ethylamine) and 4,7,10-trioxa-1,13-tridecanediamine.

Other suitable amines include, but are not limited to, tris(2-aminoethyl)amine, triethylenetetramine, N,N'-bis(3-aminopropyl)-1,3-propanediamine, tetraethylene pentamine, 1,2-diaminopropane, N,N,N',N'-tetrakis(2-hydroxyethyl)ethylene diamine, N,N,N',N'-tetrakis(2-hydroxypropyl)ethylene diamine, branched polyethylenimine, 2,4-diamino-6-hydroxypyrimidine and 2,4,6-triaminopyrimidine.

Amphoteric amines, i.e., amines that can react as an acid as well as a base, are another class of amines of use in this invention. Examples of amphoteric amines include proteins and amino acids such as gelatin, L-lysine, D-lysine, L-arginine, D-arginine, L-lysine monohydrochloride, D-lysine monohydrochloride, L-arginine monohydrochloride, D-arginine monohydrochloride, L-ornithine monohydrochloride, D-ornithine monohydrochloride or a mixture thereof.

Guanidine amines and guanidine salts are yet another class of multi-functional amines of use in this invention. Exemplary guanidine amines and guanidine salts include, but are not limited to, 1,3-diaminoguanidine monohydrochloride, 1,1-dimethylbiguanide hydrochloride, guanidine carbonate and guanidine hydrochloride.

Commercially available examples of amines include JEFFAMINE EDR-148 (where x=2), JEFFAMINE EDR-176 (where x=3) (from Huntsman). Other polyether amines include the JEFFAMINE ED Series, JEFFAMINE TRI-AMINES, polyethylenimines from BASF (Ludwigshafen, Germany) under LUPASOL grades (e.g., Lupasol FG, Lupasol G20 waterfree, Lupasol PR 8515, Lupasol WF, Lupasol FC, Lupasol G20, Lupasol G35, Lupasol G100, Lupasol G500, Lupasol HF, Lupasol PS, Lupasol HEO 1, Lupasol PN50, Lupasol PN60, Lupasol PO100 and Lupasol SK). Other commercially available polyethylenimines include EPOMIN P-1000, EPOMIN P-1050, EPOMIN RP18W and EPOMIN PP-061 from NIPPON SHOKUBAI (New York, N.Y.). Polyvinylamines such as those sold by BASF under LUPAMINE grades can also be used. A wide range of polyetheramines may be selected by those skilled in the art. In certain embodiments, the cross-linking agent is hexamethylene diamine, polyetheramine or a mixture thereof.

The structures of specific cross-linking agents are shown in the table below:

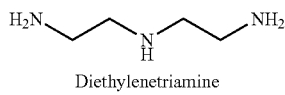
Diethylenetriamine

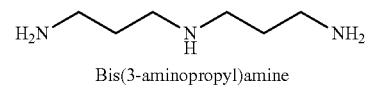
Bis(3-aminopropyl)amine

-continued
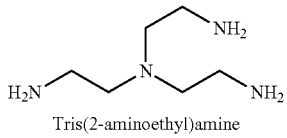
Tris(2-aminoethyl)amine
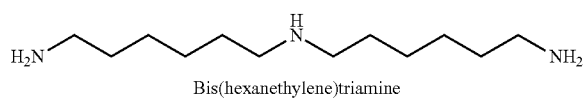 [SMILES: NCCCCCCNCCCCCCN]
Bis(hexanethylene)triamine
H(NHCH₂CH₂)₅NH₂
Pentaethylenehexamine
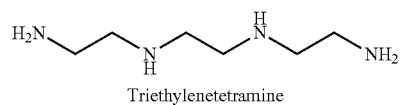
Triethylenetetramine
1,3-Diaminoguanidine monohydrochloride
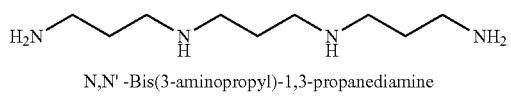 [SMILES: NCCCNCCCNCCCN]
N,N'-Bis(3-aminopropyl)-1,3-propanediamine
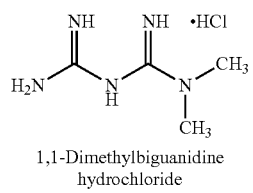
1,1-Dimethylbiguanidine hydrochloride
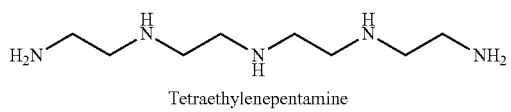 [SMILES: NCCNCCNCCNCCN]
Tetraethylenepentamine
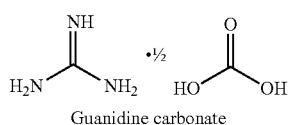
Guanidine carbonate
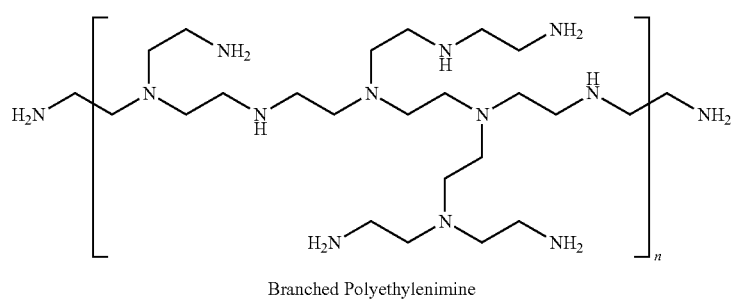
Branched Polyethylenimine
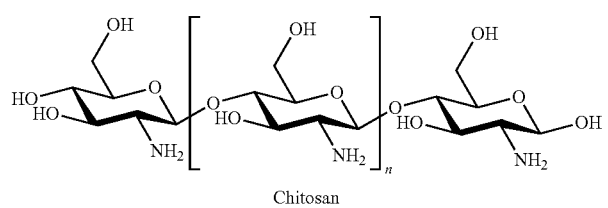
Chitosan -continued

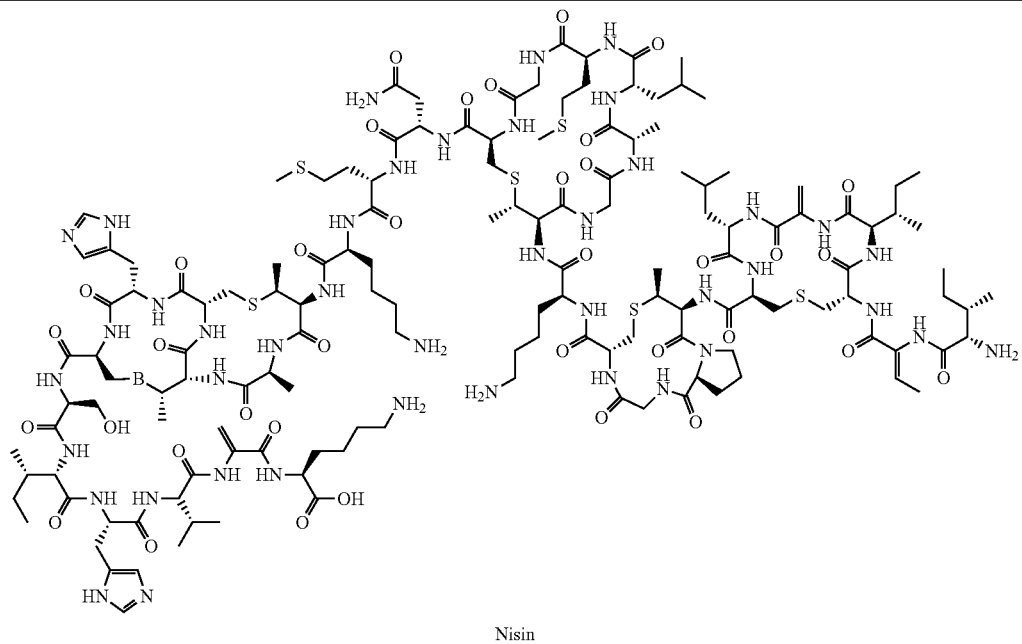

Nisin

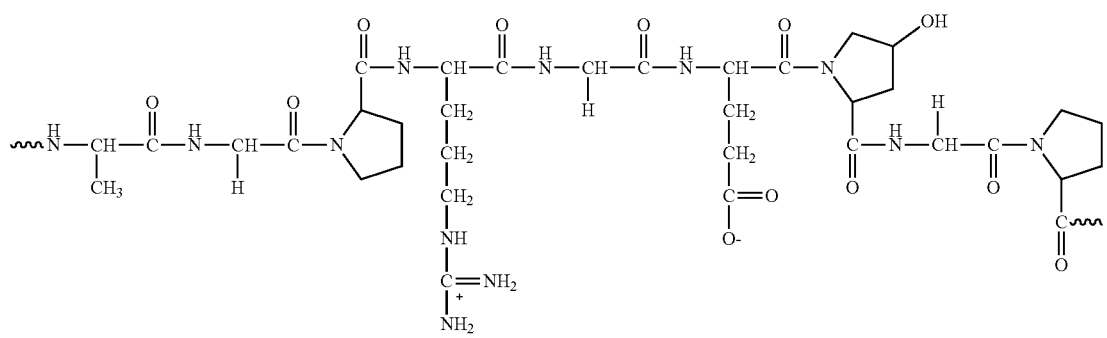

Gelatin

Polyols of use in this invention generally have at least two nucleophilic centers, e.g., ethylene glycol, hexylene glycol, pentaerythritol, glucose, sorbitol, and 2-aminoethanol.

The range of polyamine or polyol concentration can vary from 0.1% to 5% e.g., 0.2% to 3%, 0.2% to 2%, 0.5% to 2%, and 0.5% to 1%) by weight of the polyurea or polyurethane capsule composition.

By adding excess amount of a cross-linking agent, it has been observed that polyurea/polyurethane formation is driven toward completion thereby reducing the amount of residual polyisocyanate. The reaction stoichiometry requires one amine/hydroxyl group per one isocyanate group. By way of illustration, when combining LUPRANATE M20 (having a molecular weight of 360 and isocyanate functionality of 2.7) and hexamethylenediamine (HMDA; having a molecular weight of 116.21 and amine functionality of 2), the stoichiometry of the system indicates that for each gram of HMDA, 2.23 grams of LUPRANATE is needed. The amount of amine will be in excess if more than one gram of HMDA is used per 2.23 grams of LUPRANATE M20. Using a cross-linker in accordance with this invention, residual isocyanate amounts are reduced by at least 30%.

In one embodiment of the invention, the cross linking agent is added to the capsule reaction at a temperature of 0-55° C. (e.g., 10-50° C., 15-45° C., 20-40° C., and 22-35° C.).

Capsule Formation Aid. Some capsules useful in the compositions of this invention also contains a capsule formation aid, which can be a surfactant or dispersant. Not to be bound by any theory, capsule formation aids improve the performance of the capsule system. Performance is measured by the intensity of the fragrance release during the pre-rub phase and post-rub. The pre-rub phase is the phase when the capsules have been deposited on the cloth, e.g., after a fabric softener containing capsules has been used during the wash cycle. The post-rub phase is after the capsules have been deposited and the capsules are broken by friction or other similar mechanisms.

In some embodiments, the capsule formation aid is a protective colloid or emulsifier including, e.g., maleic-vinyl copolymers such as the copolymers of vinyl ethers with maleic anhydride or acid, sodium lignosulfonates, maleic anhydride/styrene copolymers, ethylene/maleic anhydride copolymers, and copolymers of propylene oxide and ethylene oxide, polyvinylpyrrolidone (PVP), polyvinyl alcohols (PVA), sodium salt of naphthalene sulfonate condensate, carboxymethyl cellulose (CMC), fatty acid esters of polyoxyethylenated sorbitol, sodium dodecylsulfate, and any combination thereof. In general, the range of surfactant concentration in the capsule composition varies from 0.1 to 5% (e.g., 0.5% to 4%, 0.2% to 2%, and 1% to 2%).

Commercially available surfactants include, but are not limited to, sulfonated naphthalene-formaldehyde condensates such as MORWET D425 (naphthalene sulfonate, Akzo Nobel, Fort Worth, Tex.); partially hydrolyzed polyvinyl alcohols such as MOWIOLs, e.g., MOWIOL 3-83 (Air Products); ethylene oxide-propylene oxide block copolymers or poloxamers such as PLURONIC, SYNPERONIC or PLURACARE materials (BASF); sulfonated polystyrenes such as FLEXAN II (Akzo Nobel); ethylene-maleic anhydride polymers such as ZEMAC (Vertellus Specialties Inc.); and Polyquaternium series such as Polyquaternium 11 ("PQ11;" a copolymer of vinyl pyrrolidone and quaternized dimethylaminoethyl methacrylate; sold by BASF as LUVIQUAT PQ11 AT 1).

Processing aids can include hydrocolloids, which improve the colloidal stability of the slurry against coagulation, sedimentation and creaming. The term "hydrocolloid" refers to a broad class of water-soluble or water-dispersible polymers having anionic, cationic, zwitterionic or non-ionic character. Hydrocolloids useful in the present invention include, but are not limited to, polycarbohydrates, such as starch, modified starch, dextrin, maltodextrin, and cellulose derivatives, and their quaternized forms; natural gums such as alginate esters, carrageenan, xanthanes, agar-agar, pectines, pectic acid, and natural gums such as gum arabic, gum tragacanth and gum karaya, guar gums and quaternized guar gums; gelatine, protein hydrolysates and their quaternized forms; synthetic polymers and copolymers, such as poly(vinyl pyrrolidone-co-vinyl acetate), poly(vinyl alcohol-co-vinyl acetate), poly((met)acrylic acid), poly(maleic acid), poly(alkyl(meth)acrylate-co-(meth)acrylic acid), poly(acrylic acid-co-maleic acid)copolymer, poly(alkyleneoxide), poly(vinylmethylether), poly(vinylether-co-maleic anhydride), and the like, as well as poly-(ethyleneimine), poly((meth)acrylamide), poly(alkyleneoxide-co-dimethylsiloxane), poly(amino dimethylsiloxane), and the like, and their quaternized forms.

The capsule formation aid may also be used in combination with CMC and/or a surfactant during processing to facilitate capsule formation. Examples of surfactants that can be used in combination with the capsule formation aid include, but are not limited to, cetyl trimethyl ammonium chloride (CTAC), poloxamers such as PLURONICS (e.g., PLURONIC F127), PLURAFAC (e.g., PLURAFAC F127), or MIRANET-N, saponins such as QNATURALE (National Starch Food Innovation); or a gum Arabic such as Seyal or Senegal. The amount of surfactant present in the capsule slurry can vary depending on the surfactant used. In some embodiments the amount of surfactant is in the range of 0.05% to 0.2% by weight of the capsule compositions, in particular when CTAC is employed. In another embodiment, the amount of surfactant is in the range of 1% to 3%.

When combined with CMC, a lighter color PVA is preferred. According to the invention, the CMC polymer may be represented by the following structure:

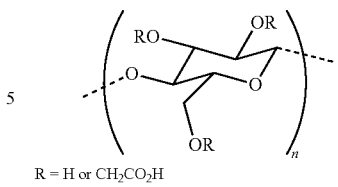

R = H or CH$_2$CO$_2$H

In certain embodiments, the CMC polymer has a molecular weight range between about 90,000 Daltons to 1,500,000 Daltons, preferably between about 250,000 Daltons to 750,000 Daltons and more preferably between 400,000 Daltons to 750,000 Daltons. The CMC polymer has a degree of substitution between about 0.1 to about 3, preferably between about 0.65 to about 1.4, and more preferably between about 0.8 to about 1.0.

The carboxymethyl cellulose polymer is present in the capsule slurry at a level from about 0.1% to about 2% and preferably from about 0.3% to about 0.7%.

In some embodiments, capsules formed in presence of a capsule aid may unexpectedly provide a perceived fragrance intensity increase of greater than about 15%, and preferably an increase of greater than about 25% as compared to capsules formed without a capsule formation aid.

Additional Polymers. In addition to the polyisocyanate, cross-linking agent, the encapsulating polymer can also include one or more additional polymers. Additional polymers that can be added to the wall at the formation of the capsules include, e.g., polyamines (polyethylenimine, poly vinyl amines, etc.), polyacrylates and polyquaterniums. In certain embodiments, the additional polymers may be selected from, but is not limited to, amphoteric and cationic polymers having a molecular weight in the range of from 1,000 to 1,000,000, preferably from 10,000 to 500,000, and more preferred between 100,000 to 200,000.

Examples of amphoteric and cationic polymers include, but not limited to, polyquaternium (e.g., polyquaternium-6 commercially available as MERQUAT 100, polyquaternium-47 commercially available as MERQUAT 2001) and polyvinylamine and its copolymers with vinylformamide and mixtures thereof. Polyvinylamines are polymers which are prepared by acidic or alkaline hydrolysis of poly(N-vinylformamides), as described, e.g., by Gu, et al. ((2002) *J. Appl. Pol. Sci.* 86:3412-3419). The corresponding products are produced in various molecular weights by BASF AG under the trade name "LUPAMIN". These products are used on a large scale, for example, as paper chemicals, in the personal care sector, as super-absorbents or dispersants. The LUPAMIN commercial products still contain the salts formed from the hydrolysis. For the application sector described, the modification of waveguide surfaces, both the salt-containing and the desalinified form can be used. The desalinification can be effected, for example, by ultrafiltration. In a preferred embodiment the polyvinylamine is LUPAMIN 9095 (polyvinylamine PVAm 340,000 g/mol) commercially available from BASF.

In some embodiments, the encapsulating polymer contains from 0.01 to 20 weight percent of the additional polymer, on a solid basis. In other embodiments, the encapsulating polymer contains from 0.1 to 10 weight percent of the additional polymer, on a solid basis. In particular embodiments, the additional polymer is polyquaternium-6 and is present, on a solid basis, in the range of 0.25 to about 10 weight percent. In a further embodiment, the polymer is a mixture of polyquaternium-6 and a polyvinyl amine, specifically LUPAMIN 9095, wherein the polyquaternium-6 may be present, on a solid basis, in the range of preferably 0.5 to 5 weight percent and the polyvinylamine present, on a solid basis, from about 0.25 to 10 weight percent. In still a further embodiment, the additional polymer is a mixture of polyquaternium-6 and polyvinylamine wherein the polyquaternium-6 is present, on a solid basis, in the range of preferably 0.5 to 5 weight percent and the polyvinylamine is present, on a solid basis, in the range of preferably 0.5 to 8 weight percent. In yet another embodiment, the additional polymer is a mixture of polyquaternium-6 and polyvinylamine wherein the polyquaternium-6 is present, on a solid basis, at a level of about 1.5 weight percent and the polyvinylamine is present, on a solid basis, 1 weight percent.

According to certain other embodiments of the invention, the additional polymer is added at between 35° C. and 55° C.

Catalysts. Catalysts suitable for use in the invention are metal carbonates, metal hydroxide, amino or organometallic compounds and include, for example, sodium carbonate, cesium carbonate, potassium carbonate, lithium hydroxide, 1,4-diazabicyclo[2.2.2]octane (i.e., DABCO), N,N-dimethylaminoethanol, N,N-dimethylcyclohexylamine, bis-(2-dimethylaminoethyl) ether, N,N dimethylacetylamine, stannous octoate and dibutyltin dilaurate.

Core/Active Materials. The core of the capsules of the invention can include one or more active materials including, but not limited to, flavors and/or fragrance ingredients such as fragrance oils. Individual perfume ingredients that can be included in the capsules of this invention include fragrances containing:

i) hydrocarbons, such as, for example, 3-carene, α-pinene, β-pinene, α-terpinene, γ-terpinene, p-cymene, bisabolene, camphene, caryophyllene, cedrene, farnesene, limonene, longifolene, myrcene, ocimene, valencene, (E,Z)-1,3,5-undecatriene, styrene, and diphenylmethane;

ii) aliphatic alcohols, such as, for example, hexanol, octanol, 3-octanol, 2,6-dimethylheptanol, 2-methyl-2-heptanol, 2-methyl-2-octanol, (E)-2-hexenol, (E)- and (Z)-3-hexenol, 1-octen-3-ol, a mixture of 3,4,5,6,6-pentamethyl-3/4-hepten-2-ol and 3,5,6,6-tetramethyl-4-methyleneheptan-2-ol, (E,Z)-2,6-nonadienol, 3,7-dimethyl-7-methoxyoctan-2-ol, 9-decenol, 10-undecenol, 4-methyl-3-decen-5-ol, aliphatic aldehydes and their acetals such as for example hexanal, heptanal, octanal, nonanal, decanal, undecanal, dodecanal, tridecanal, 2-methyloctanal, 2-methylnonanal, (E)-2-hexenal, (Z)-4-heptenal, 2,6-dimethyl-5-heptenal, 10-undecenal, (E)-4-decenal, 2-dodecenal, 2,6,10-trimethyl-5,9-undecadienal, heptanal-diethylacetal, 1,1-dimethoxy-2,2,5-trimethyl-4-hexene, and citronellyl oxyacetaldehyde;

iii) aliphatic ketones and oximes thereof, such as, for example, 2-heptanone, 2-octanone, 3-octanone, 2-nonanone, 5-methyl-3-heptanone, 5-methyl-3-heptanone oxime, 2,4,4,7-tetramethyl-6-octen-3-one, aliphatic sulfur-containing compounds, such as for example 3-methylthiohexanol, 3-methylthiohexyl acetate, 3-mercaptohexanol, 3-mercaptohexyl acetate, 3-mercaptohexyl butyrate, 3-acetylthiohexyl acetate, 1-menthene-8-thiol, and aliphatic nitriles (e.g., 2-nonenenitrile, 2-tridecenenitrile, 2,12-tridecenenitrile, 3,7-dimethyl-2,6-octadienenitrile, and 3,7-dimethyl-6-octenenitrile);

iv) aliphatic carboxylic acids and esters thereof, such as, for example, (E)- and (Z)-3-hexenylformate, ethyl acetoacetate, isoamyl acetate, hexyl acetate, 3,5,5-trimethylhexyl acetate, 3-methyl-2-butenyl acetate, (E)-2-hexenyl acetate, (E)- and (Z)-3-hexenyl acetate, octyl acetate, 3-octyl acetate, 1-octen-3-yl acetate, ethyl butyrate, butyl butyrate, isoamyl butyrate, hexylbutyrate, (E)- and (Z)-3-hexenyl isobutyrate, hexyl crotonate, ethylisovalerate, ethyl-2-methyl pentanoate, ethyl hexanoate, allyl hexanoate, ethyl heptanoate, allyl heptanoate, ethyl octanoate, ethyl-(E,Z)-2,4-decadienoate, methyl-2-octinate, methyl-2-noninate, allyl-2-isoamyl oxyacetate, and methyl-3,7-dimethyl-2,6-octadienoate;

v) acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as formates, acetates, propionates, isobutyrates, butyrates, isovalerates, pentanoates, hexanoates, crotonates, tiglinates and 3-methyl-2-butenoates thereof;

vi) acyclic terpene aldehydes and ketones, such as, for example, geranial, neral, citronellal, 7-hydroxy-3,7-dimethyloctanal, 7-methoxy-3,7-dimethyloctanal, 2,6,10-trimethyl-9-undecenal, α-sinensal, β-sinensal, geranylacetone, as well as the dimethyl- and diethylacetals of geranial, neral and 7-hydroxy-3,7-dimethyloctanal;

vii) cyclic terpene alcohols, such as, for example, menthol, isopulegol, alpha-terpineol, terpinen-4-ol, menthan-8-ol, menthan-1-ol, menthan-7-ol, borneol, isoborneol, linalool oxide, nopol, cedrol, ambrinol, vetiverol, guaiol, and the formates, acetates, propionates, isobutyrates, butyrates, isovalerates, pentanoates, hexanoates, crotonates, tiglinates and 3-methyl-2-butenoates of alpha-terpineol, terpinen-4-ol, methan-8-ol, methan-1-ol, methan-7-ol, borneol, isoborneol, linalool oxide, nopol, cedrol, ambrinol, vetiverol, and guaiol;

viii) cyclic terpene aldehydes and ketones, such as, for example, menthone, isomenthone, 8-mercaptomenthan-3-one, carvone, camphor, fenchone, α-ionone, β-ionone, α-n-methylionone, β-n-methylionone, α-isomethylionone, β-isomethylionone, alpha-irone, α-damascone, β-damascone, β-damascenone, δ-damascone, γ-damascone, 1-(2,4,4-trimethyl-2-cyclohexen-1-yl)-2-buten-1-one, 1,3,4,6,7,8a-hexahydro-1,1,5,5-tetramethyl-2H-2,4a-methanonaphthalen-8(5H-)-one, nootkatone, dihydronootkatone; acetylated cedarwood oil (cedryl methyl ketone);

ix) cyclic alcohols, such as, for example, 4-tert-butylcyclohexanol, 3,3,5-trimethylcyclohexanol, 3-isocamphylcyclohexanol, 2,6,9-trimethyl-Z2,Z5,E9-cyclododecatrien-1-ol, 2-isobutyl-4-methyltetrahydro-2H-pyran-4-ol;

x) cycloaliphatic alcohols, such as, for example, alpha,3,3-trimethylcyclo-hexylmethanol, 2-methyl-4-(2,2,3-trimethyl-3-cyclopent-1-yl)butanol, 2-methyl-4-(2,2,3-trimethyl-3-cyclopent-1-yl)-2-buten-1-ol, 2-ethyl-4-(2,2,3-trimethyl-3-cyclopent-1-yl)-2-buten-1-ol, 3-methyl-5-(2,2,3-trimethyl-3-cyclopent-1-yl)-pentan-2-ol, 3-methyl-5-(2,2,3-trimethyl-3-cyclopent-1-yl)-4-penten-2-ol, 3,3-dimethyl-5-(2,2,3-trimethyl-3-cyclopent-1-yl)-4-penten-2-ol, 1-(2,2,6-trimethylcyclohexyl)pentan-3-ol, 1-(2,2,6-trimethylcyclohexyl)hexan-3-ol;

xi) cyclic and cycloaliphatic ethers, such as, for example, cineole, cedryl methyl ether, cyclododecyl methyl ether;

xii) (ethoxymethoxy)cyclododecane; alpha-cedrene epoxide, 3a,6,6,9a-tetramethyldodecahydronaphtho[2,1-b]furan, 3a-ethyl-6,6,9a-trimethyldodecahydronaphtho[2,1-b]furan, 1,5,9-trimethyl-13-oxabicyclo[10.1.0]-trideca-4,8-diene, rose oxide, 2-(2,4-dimethyl-3-cyclohexen-1-yl)-5-methyl-5-(1-methylpropyl)-1,3-dioxan-;

xiii) cyclic ketones, such as, for example, 4-tert.-butyl-cyclohexanone, 2,2,5-trimethyl-5-pentylcyclopentanone, 2-heptylcyclopentanone, 2-pentylcyclopentanone, 2-hydroxy-3-methyl-2-cyclopenten-1-one, 3-methyl-cis-2-penten-1-yl-2-cyclopenten-1-one, 3-methyl-2-pentyl-2-cyclopenten-1-one, 3-methyl-4-cyclopentadecenone, 3-methyl-5-cyclopentadecenone, 3-methylcyclopentadecanone, 4-(1-ethoxyvinyl)-3,3,5,5-tetramethylcyclohexanone, 4-tert.-pentylcyclohexanone, 5-cyclohexadecen-1-one, 6,7-dihydro-1,1,2,3,3-pentamethyl-4(5H)-indanone, 5-cyclohexadecen-1-one, 8-cyclohexadecen-1-one, 9-cycloheptadecen-1-one, cyclopentadecanone, cycloaliphatic aldehydes, such as, for example, 2,4-dimethyl-3-cyclohexene carbaldehyde, 2-methyl-4-(2,2,6-trimethyl-cyclohexen-1-yl)-2-butenal, 4-(4-hydroxy-4-methylpentyl)-3-cyclohexene carbaldehyde, 4-(4-methyl-3-penten-1-yl)-3-cyclohexene carbaldehyde;

xiv) cycloaliphatic ketones, such as, for example, 1-(3,3-dimethylcyclohexyl)-4-penten-1-one, 1-(5,5-dimethyl-1-cyclohexen-1-yl)-4-penten-1-one, 2,3,8,8-tetramethyl-1,2,3,4,5,6,7,8-octahydro-2-naphtalenyl methyl-ketone, methyl-2,6,10-trimethyl-2,5,9-cyclododecatrienyl ketone, tert.-butyl-(2,4-dimethyl-3-cyclohexen-1-yl)ketone;

xv) esters of cyclic alcohols, such as, for example, 2-tert.-butylcyclohexyl acetate, 4-tert-butylcyclohexyl acetate, 2-tert-pentylcyclohexyl acetate, 4-tert-pentylcyclohexyl acetate, decahydro-2-naphthyl acetate, 3-pentyltetrahydro-2H-pyran-4-yl acetate, decahydro-2,5,5,8a-tetramethyl-2-naphthyl acetate, 4,7-methano-3a,4,5,6,7,7a-hexahydro-5 or 6-indenyl acetate, 4,7-methano-3a,4,5,6,7,7a-hexahydro-5 or 6-indenyl propionate, 4,7-methano-3a,4,5,6,7,7a-hexahydro-5 or 6-indenyl-isobutyrate, 4,7-methanooctahydro-5 or 6-indenyl acetate;

xvi) esters of cycloaliphatic carboxylic acids, such as, for example, allyl 3-cyclohexyl-propionate, allyl cyclohexyl oxyacetate, methyl dihydrojasmonate, methyl jasmonate, methyl 2-hexyl-3-oxocyclopentanecarboxylate, ethyl 2-ethyl-6,6-dimethyl-2-cyclohexenecarboxylate, ethyl 2,3,6,6-tetramethyl-2-cyclohexenecarboxylate, ethyl 2-methyl-1,3-dioxolane-2-acetate;

xvii) aromatic and aliphatic alcohols, such as, for example, benzyl alcohol, 1-phenylethyl alcohol, 2-phenylethyl alcohol, 3-phenylpropanol, 2-phenylpropanol, 2-phenoxyethanol, 2,2-dimethyl-3-phenylpropanol, 2,2-dimethyl-3-(3-methylphenyl)propanol, 1,1-dimethyl-2-phenylethyl alcohol, 1,1-dimethyl-3-phenylpropanol, 1-ethyl-1-methyl-3-phenylpropanol, 2-methyl-5-phenylpentanol, 3-methyl-5-phenylpentanol, 3-phenyl-2-propen-1-ol, 4-methoxybenzyl alcohol, 1-(4-isopropylphenyl)ethanol;

xviii) esters of aliphatic alcohols and aliphatic carboxylic acids, such as, for example, benzyl acetate, benzyl propionate, benzyl isobutyrate, benzyl isovalerate, 2-phenylethyl acetate, 2-phenylethyl propionate, 2-phenylethyl isobutyrate, 2-phenylethyl isovalerate, 1-phenylethyl acetate, α-trichloromethylbenzyl acetate, α,α-dimethylphenylethyl acetate, alpha, alpha-dimethylphenylethyl butyrate, cinnamyl acetate, 2-phenoxyethyl isobutyrate, 4-methoxybenzyl acetate, araliphatic ethers, such as for example 2-phenylethyl methyl ether, 2-phenylethyl isoamyl ether, 2-phenylethyl-1-ethoxyethyl ether, phenylacetaldehyde dimethyl acetal, phenylacetaldehyde diethyl acetal, hydratropaaldehyde dimethyl acetal, phenylacetaldehyde glycerol acetal, 2,4,6-trimethyl-4-phenyl-1,3-dioxane, 4,4a,5,9b-tetrahydroindeno[1,2-d]-m-dioxin, 4,4a,5,9b-tetrahydro-2,4-dimethylindeno[1,2-d]-m-dioxin;

xix) aromatic and aliphatic aldehydes, such as, for example, benzaldehyde; phenylacetaldehyde, 3-phenylpropanal, hydratropaldehyde, 4-methylbenzaldehyde, 4-methylphenylacetaldehyde, 3-(4-ethylphenyl)-2,2-dimethylpropanal, 2-methyl-3-(4-isopropylphenyl)propanal, 2-methyl-3-(4-tert.-butylphenyl)propanal, 3-(4-tert.-butylphenyl) propanal, cinnamaldehyde, alpha-butylcinnamaldehyde, alpha-amylcinnamaldehyde, alpha-hexylcinnamaldehyde, 3-methyl-5-phenylpentanal, 4-methoxybenzaldehyde, 4-hydroxy-3-methoxybenzaldehyde, 4-hydroxy-3-ethoxybenzaldehyde, 3,4-methylene-dioxybenzaldehyde, 3,4-dimethoxybenzaldehyde, 2-methyl-3-(4-methoxyphenyl)propanal, 2-methyl-3-(4-methylendioxyphenyl)propanal;

xx) aromatic and aliphatic ketones, such as, for example, acetophenone, 4-methylacetophenone, 4-methoxyacetophenone, 4-tert.-butyl-2,6-dimethylacetophenone, 4-phenyl-2-butanone, 4-(4-hydroxyphenyl)-2-butanone, 1-(2-naphthalenyl)ethanone, benzophenone, 1,1,2,3,3,6-hexamethyl-5-indanyl methyl ketone, 6-tert.-butyl-1,1-dimethyl-4-indanyl methyl ketone, 1-[2,3-dihydro-1,1,2,6-tetramethyl-3-(1-methyl-ethyl)-1H-5-indenyl]ethanone, 5 ',6',7',8'-tetrahydro-3 ',5',5',6',8',8'-hexamethyl-2-acetonaphthone;

xxi) aromatic and araliphatic carboxylic acids and esters thereof, such as, for example, benzoic acid, phenylacetic acid, methyl benzoate, ethyl benzoate, hexyl benzoate, benzyl benzoate, methyl phenylacetate, ethyl phenylacetate, geranyl phenylacetate, phenylethyl phenylacetate, methyl cinnamate, ethyl cinnamate, benzyl cinnamate, phenylethyl cinnamate, cinnamyl cinnamate, allyl phenoxyacetate, methyl salicylate, isoamyl salicylate, hexyl salicylate, cyclohexyl salicylate, cis-3-hexenyl salicylate, benzyl salicylate, phenylethyl salicylate, methyl 2,4-dihydroxy-3,6-dimethylbenzoate, ethyl 3-phenylglycidate, ethyl 3-methyl-3-phenylglycidate;

xxii) nitrogen-containing aromatic compounds, such as, for example, 2,4,6-trinitro-1,3-dimethyl-5-tert-butylbenzene, 3,5-dinitro-2,6-dimethyl-4-tert-butylacetophenone, cinnamonitrile, 5-phenyl-3-methyl-2-pentenonitrile, 5-phenyl-3-methylpentanonitrile, methyl anthranilate, methy-N-methylanthranilate, Schiff's bases of methyl anthranilate with 7-hydroxy-3,7-dimethyloctanal, 2-methyl-3-(4-tert.-butylphenyl)propanal or 2,4-dimethyl-3-cyclohexene carbaldehyde, 6-isopropylquinoline, 6-isobutylquinoline, 6-sec-butylquinoline, indole, skatole, 2-methoxy-3-isopropylpyrazine, 2-isobutyl-3-methoxypyrazine;

xxiii) phenols, phenyl ethers and phenyl esters, such as, for example, estragole, anethole, eugenol, eugenyl methyl ether, isoeugenol, isoeugenol methyl ether, thymol, carvacrol, diphenyl ether, beta-naphthyl methyl ether, beta-naphthyl ethyl ether, beta-naphthyl isobutyl ether, 1,4-dimethoxybenzene, eugenyl acetate, 2-methoxy-4-methylphenol, 2-ethoxy-5-(1-propenyl)phenol, p-cresyl phenylacetate;

xxiv) heterocyclic compounds, such as, for example, 2,5-dimethyl-4-hydroxy-2H-furan-3-one, 2-ethyl-4-hydroxy-5-methyl-2H-furan-3-one, 3-hydroxy-2-methyl-4H-pyran-4-one, 2-ethyl-3-hydroxy-4H-pyran-4-one;

xxv) lactones, such as, for example, 1,4-octanolide, 3-methyl-1,4-octanolide, 1,4-nonanolide, 1,4-decanolide, 8-decen-1,4-olide, 1,4-undecanolide, 1,4-dodecanolide, 1,5-decanolide, 1,5-dodecanolide, 1,15-pentadecanolide, cis- and trans-11-pentadecen-1,15-olide, cis- and trans-12-pentadecen-1,15-olide, 1,16-hexadecanolide, 9-hexadecen-1,16-olide, 10-oxa-1,16-hexadecanolide, 11-oxa-1,16-hexadecanolide, 12-oxa-1,16-hexadecanolide, ethylene-1,12-dodecanedioate, ethylene-1,13-tridecanedioate, coumarin, 2,3-dihydrocoumarin, and octahydrocoumarin; and xxvi) essential oils, concretes, absolutes, resins, resinoids, balsams, tinctures such as for example ambergris tincture, amyris oil, *angelica* seed oil, *angelica* root oil, aniseed oil, valerian oil, basil oil, tree moss absolute, bay oil, armoise oil, benzoe resinoid, bergamot oil, beeswax absolute, birch tar oil, bitter almond oil, savory oil, buchu leaf oil, cabreuva oil, cade oil, calamus oil, camphor oil, *cananga* oil, cardamom oil, cascarilla oil, *cassia* oil, cassie absolute, castoreum absolute, cedar leaf oil, cedar wood oil, cistus oil, citronella oil, lemon oil, copaiba balsam, copaiba balsam oil, coriander oil, costus root oil, cumin oil, cypress oil, davana oil, dill weed oil, dill seed oil, eau de brouts absolute, oakmoss absolute, elemi oil, estragon oil, *eucalyptus citriodora* oil, *eucalyptus* oil (cineole type), fennel oil, fir needle oil, *galbanum* oil, *galbanum* resin, geranium oil, grapefruit oil, guaiacwood oil, gurjun balsam, gurjun balsam oil, helichrysum absolute, helichrysum oil, ginger oil, iris root absolute, iris root oil, jasmine absolute, calamus oil, blue camomile oil, Roman camomile oil, carrot seed oil, cascarilla oil, pine needle oil, spearmint oil, caraway oil, labdanum oil, labdanum absolute, labdanum resin, lavandin absolute, lavandin oil, lavender absolute, lavender oil, lemon-grass oil, lovage oil, lime oil distilled, lime oil expressed, linaloe oil, *Litsea cubeba* oil, laurel leaf oil, mace oil, marjoram oil, mandarin oil, massoi (bark) oil, *mimosa* absolute, ambrette seed oil, musk tincture, clary sage oil, nutmeg oil, myrrh absolute, myrrh oil, myrtle oil, clove leaf oil, clove bud oil, neroli oil, olibanum absolute, olibanum oil, opopanax oil, orange flower absolute, orange oil, *origanum* oil, palmarosa oil, patchouli oil, *perilla* oil, Peru balsam oil, parsley leaf oil, parsley seed oil, petitgrain oil, peppermint oil, pepper oil, pimento oil, pine oil, pennyroyal oil, rose absolute, rosewood oil, rose oil, rosemary oil, Dalmatian sage oil, Spanish sage oil, sandal-wood oil, celery seed oil: spike-lavender oil, star anise oil, storax oil, *tagetes* oil, fir needle oil, tea tree oil, turpentine oil, thyme oil, Tolu balsam, tonka bean absolute, tuberose absolute, vanilla extract, violet leaf absolute, *verbena* oil, vetiver oil, juniperberry oil, wine lees oil, wormwood oil, wintergreen oil, ylang-ylang oil, hyssop oil, civet absolute, cinnamon leaf oil, cinnamon bark oil, and fractions thereof or ingredients isolated therefrom.

In some embodiments, the amount of encapsulated active material is from about 0.5% to 80% by weight of the capsule composition, preferably from about 10% to about 60%, and more preferably from about 20% to about 50%.

In addition to the fragrance materials, the present invention also contemplates the incorporation of other core additives including solvent, emollients, and core modifier materials encapsulated by the encapsulating polymer.

The present invention also contemplates the incorporation of solvent materials, particles or polymeric core modifiers into the core. The solvent materials are hydrophobic materials that are miscible in the active materials. The solvent materials serve to increase the compatibility of various active materials, increase the overall hydrophobicity of the mixture containing the active materials, influence the vapor pressure, or serve to structure the mixture. Suitable solvents are those having reasonable affinity for the active materials and a C log P greater than 2.5, preferably greater than 3.5 and more preferably greater than 5.5. In some embodiments, the solvent is combined with the active materials that have C log P values as set forth above. It should be noted that selecting a solvent and active material with high affinity for each other will result in improvement in stability. Suitable solvents include triglyceride oil, mono and diglycerides, mineral oil, silicone oil, diethyl phthalate, polyalpha olefins, castor oil, isopropyl myristate, mono-, di- and tri-esters of mixtures thereof, fatty acids, and glycerine. The fatty acid chain can range from $C_4$-$C_{26}$ and can have any level of unsaturation. For instance, one of the following solvents can be used: capric/caprylic triglyceride known as NEOBEE M5 (Stepan Corporation); the CAPMUL series by Abitec Corporation (e.g., CAPMUL MCM); isopropyl myristate; fatty acid esters of polyglycerol oligomers, e.g., R2CO—[OCH$_2$—CH(OCOR1)-CH$_2$O—]$_n$, where R1 and R2 can be H or $C_4$-$C_{26}$ aliphatic chains, or mixtures thereof; and n ranges between 2 and 50, preferably 2 and 30; nonionic fatty alcohol alkoxylates like the NEODOL surfactants by BASF; the dobanol surfactants by Shell Corporation or the BIO-SOFT surfactants by Stepan, wherein the alkoxy group is ethoxy, propoxy, butoxy, or mixtures thereof and said surfactants can be end-capped with methyl groups in order to increase their hydrophobicity; di- and tri-fatty acid chain containing nonionic, anionic and cationic surfactants, and mixtures thereof; fatty acid esters of polyethylene glycol, polypropylene glycol, and polybutylene glycol, or mixtures thereof; polyalphaolefins such as the EXXONMOBIL PURESYM PAO line; esters such as the EXXONMOBIL PURESYN esters; mineral oil; silicone oils such polydimethyl siloxane and polydimethylcyclosiloxane; diethyl phthalate; di-octyl adipate and di-isodecyl adipate. In certain embodiments, ester oils have at least one ester group in the molecule. One type of common ester oil useful in the present invention are the fatty acid mono and polyesters such as cetyl octanoate, octyl isonanoanate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester and polyesters, sorbitol ester, and the like. A second type of useful ester oil is predominantly composed of triglycerides and modified triglycerides. These include vegetable oils such as jojoba, soybean, canola, sunflower, safflower, rice bran, avocado, almond, olive, sesame, persic, castor, coconut, and mink oils. Synthetic triglycerides can also be employed provided they are liquid at room temperature. Modified triglycerides include materials such as ethoxylated and maleated triglyceride derivatives provided they are liquids. Proprietary ester blends such as those sold by FINETEX as FINSOLV are also suitable, as is ethylhexanoic acid glyceride. A third type of ester oil is liquid polyester formed from the reaction of a dicarboxylic acid and a diol. Examples of polyesters suitable for the present invention are the polyesters marketed by EXXONMOBIL under the trade name PURESYN ESTER.

While no solvent is needed in the core, it is preferable that the level of solvent in the core of the capsule product is about 80 wt % or less, preferably about 50 wt % or less (e.g., 0-20 wt %).

When the active material is a fragrance, it is preferred that fragrance ingredients within a fragrance having a high C log P are employed. For instance, the ingredients having a C log P value between 2 and 7 (e.g., between 2 and 6, and between 2 and 5) are about 25% or greater (e.g., 50% or greater and 90% or greater) by the weight of the fragrance. Those skilled in the art will appreciate that many fragrances can be created employing various solvents and fragrance ingredients. The use of relatively low to intermediate C log P fragrance ingredients will result in fragrances that are suitable for encapsulation. These fragrances are generally water-insoluble, to be delivered through the capsule systems of this invention onto consumer products in different stages such as damp and dry fabric. Without encapsulation, the free fragrances would normally have evaporated or dissolved in water during use, e.g., wash. Whilst high log P materials have excellent encapsulation properties they are generally well delivered from a regular (non-encapsulated) fragrance in a consumer product. Such fragrance chemicals would generally only need encapsulation for overall fragrance character purposes, very long-lasting fragrance delivery, or overcoming incompatibility with the consumer product, e.g., fragrance materials that would otherwise be instable, cause thickening or discoloration of the product or otherwise negatively affect desired consumer product properties.

Nanoscale solid particulate materials such as those disclosed in U.S. Pat. No. 7,833,960 may also be incorporated into the core and may be selected from, but not limited to, metal or metallic particles, metal alloys, polymer particles, wax particles, inorganic particulates, minerals and clay particles.

The metal particles can be selected from a non-limiting list of main group elements, transition metal and post-transition metal elements including aluminum (Al), silica (Si), Titanium (Ti), chromium (Cr), manganese (Mn), iron (Fe), nickel (Ni), cobalt (Co), copper (Cu), gold (Au), silver (Ag), platinum (Pt) and palladium (Pd).

Polymer particles of any chemical composition and nature are suitable for the present invention as long as their physical dimension falls into the prescribed region and a liquid core is generated. The polymer particles can be selected from a nonlimiting list of polymers and co-copolymer based on polystyrene, polyvinyl acetate, polylactides, polyglycolides, ethylene maleic anhydride copolymer, polyethylene, polypropylene, polyamide, polyimide, polycarbonate, polyester, polyurethane, polyurea, cellulose and cellulose, and combinations and mixture of such polymers.

The inorganic particulate can be selected from a non-limiting list including silica, titanium dioxide ($TiO_2$), zinc oxide (ZnO), $Fe_2O_3$, and other metal oxides such as but not limited to NiO, $Al_2O_3$, SnO, $SnO_2$, $CeO_2$, ZnO, CdO, $RuO_2$, FeO, CuO, AgO, $MnO_2$, as well as other transition metal oxides.

Examples of nanoscaled material include AEROSIL R812, which has a particle size of less than 25 nm according to the specification from the manufacture, Degussa Corp. Other suitable materials from Degussa include, but not limited to, AEROSIL R972, AEROSIL R974, AEROSIL R104, AEROSIL R106, AEROSIL R202, AEROSIL R805, AEROSIL R812, AEROSIL R812S, AEROSIL R816, AEROSIL R7200, AEROSIL R9200, and AEROXIDE $TiO_2$ P25, AEROXIDE T805, AEROXIDE LE1, AEROXIDE LE2, AEROXIDE $TiO_2$ NKT 90, AEROXIDE Alu C805, titanium dioxide PF2, SIPERNAT D110, SIPERNAT D-380. The hydrophobic materials from Deguassa Corp. such as including AEROSILE R812 and R972 are especially preferred.

Nanoscaled materials such as UVINUL $TiO_2$ and Z-COTE HP1 manufactured by BASF can also be used as well as and TI-PURE titanium dioxide, TI-PURE R-700, and TI-SELECT. Additional suitable materials include TS-6200 from Dupont and ZEROFREE 516, HUBERDERM 2000 and HUBERDERM 1000 from the J.M. Huber Corporation, Havre De Grace, Md. Silica products such as SYLOID 63, 244, 72, 63FP 244FP, 72FP, SYLOX 15, 2 and Zeolites such as SYLOSIV A3, SYLOSIV A4 and SYLOSIV K300 from Grace Davison can also be used.

Polymeric core modifiers are also contemplated. It has been found that the addition of hydrophobic polymers to the core can also improve stability by slowing diffusion of the fragrance from the core. The level of polymer is normally less than 80% of the core by weight, preferably less than 50%, and most preferably less than 20%. The basic requirement for the polymer is that it be miscible or compatible with the other components of the core, namely the fragrance and other solvent. Preferably, the polymer also thickens or gels the core, thus further reducing diffusion. Polymeric core modifiers include copolymers of ethylene; copolymers of ethylene and vinyl acetate (ELVAX polymers by DOW Corporation); copolymers of ethylene and vinyl alcohol (EVAL polymers by Kuraray); ethylene/acrylic elastomers such as VALNAC polymers by Dupont; polyvinyl polymers, such as polyvinyl acetate; alkyl-substituted cellulose, such as ethyl cellulose (ETHOCEL made by DOW Corporation) and hydroxypropyl celluloses (KLUCEL polymers by Hercules); cellulose acetate butyrate available from Eastman Chemical; polyacrylates (e.g., AMPHOMER, DEMACRYL LT and DERMACRYL 79, made by National Starch and Chemical Company, the AMERHOLD polymers by Amerchol Corporation, and ACUDYNE 258 by ISP Corporation); copolymers of acrylic or methacrylic acid and fatty esters of acrylic or methacrylic acid such as INTELIMER POLYMERS made by Landec Corporation (see also U.S. Pat. Nos. 4,830,855, 5,665,822, 5,783,302, 6,255,367 and 6,492,462); polypropylene oxide; polybutylene oxide of poly(tetrahydrofuran); polyethylene terephthalate; polyurethanes (DYNAM X by National Starch); alkyl esters of poly(methyl vinyl ether); maleic anhydride copolymers, such as the GANTREZ copolymers and OMNIREZ 2000 by ISP Corporation; carboxylic acid esters of polyamines, e.g., ester-terminated polyamides (ETPA) made by Arizona Chemical Company; polyvinyl pyrrolidone (LUVISKOL series of BASF); block copolymers of ethylene oxide, propylene oxide and/or butylenes oxide including, e.g., PLURONIC and SYNPERONIC polymers/dispersants by BASF. Another class of polymers include polyethylene oxide-co-propyleneoxide-co-butylene oxide polymers of any ethylene, oxide/propylene oxide/butylene oxide ratio with cationic groups resulting in a net theoretical positive charge or equal to zero (amphoteric). The general structure is:

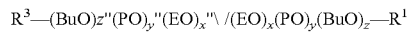

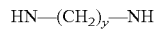

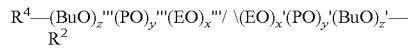

where $R^1$, $R^2$, $R^3$, and $R^4$ are independently H or any alkyl or fatty alkyl chain group. Examples of such polymers are the commercially known as TEIRONICS by BASF Corporation.

Sacrificial core ingredients can also be included. These ingredients are designed to be lost during or after manufacture and include, but are not limited to, highly water soluble or volatile materials.

One or more adjunct material may be added to the capsule compositions in the amount of from about 0.01% to about 25% (e.g., from about 0.5% to about 10%).

The adjunct material can be a solubility modifier, an antibacterial, a sunscreen active, an antioxidant, a malodor counteracting ingredient, a density modifier, a stabilizer, a viscosity modifier, a pH modifier, or any combination thereof. These modifiers can be present in the wall or core of the capsules, or outside the capsules in compositions of this invention. Preferably, they are in the core as a core modifier.

Nonlimiting examples of a solubility modifier include surfactants (e.g., SLS and Tween 80), acidic compounds (e.g., mineral acids such as sulfuric acid, hydrochloric acid, nitric acid, and phosphoric acid, and carboxylic acids such as acetic acid, citric acid, gluconic acid, glucoheptonic acid, and lactic acid), basic compounds (e.g., ammonia, alkali metal and alkaline earth metal hydroxides, primary, secondary, or tertiary amines, and primary, secondary, or tertiary alkanolamines), ethyl alcohol, glycerol, glucose, galactose, inositol, mannitol, glactitol, adonitol, arabitol, and amino acids.

Exemplary antibacterials include bisguanidines (e.g., chlorhexidine digluconate), diphenyl compounds, benzyl alcohols, trihalocarbanilides, quaternary ammonium compounds, ethoxylated phenols, and phenolic compounds, such as halo-substituted phenolic compounds, like PCMX (i.e., p-chloro-m-xylenol), triclosan (i.e., 2,4,4'-trichloro-2' hydroxy-diphenylether), thymol, and triclocarban.

Suitable sunscreen actives include oxybenzone, octylmethoxy cinnamate, butylmethoxy dibenzoyln ethane, p-aminobenzoic acid and octyl dimethyl-p-aminobenzoic acid.

Examples of antioxidants include beta-carotene, vitamin C (Ascorbic Acid) or an ester thereof, vitamin A or an ester thereof, vitamin E or an ester thereof, lutein or an ester thereof, lignan, lycopene, selenium, flavonoids, vitamin-like antioxidants such as coenzyme Q10 (CoQ10) and glutathione, and antioxidant enzymes such as superoxide dismutase (SOD), catalase, and glutathione peroxidase.

Malodor counteracting ingredients include, but not limited to, an α,β-unsaturated carbonyl compounds including but not limited to those disclosed in U.S. Pat. No. 6,610,648 and EP 2,524,704, amyl cinnamaldehyde, benzophenone, benzyl benzoate, benzyl isoeugenol, benzyl phenyl acetate, benzyl salicylate, butyl cinnamate, cinnamyl butyrate, cinnamyl isovalerate, cinnamyl propionate, decyl acetate, ethyl myristate, isobutyl cinnamate, isoamyl salicylate, phenethyl benzoate, phenethyl phenyl acetate, triethyl citrate, tripropylene glycol n-butyl ether, isomers of bicyclo[2.2.1]hept-5-ene-2-carboxylic acid, ethyl ester, nano silver, and zinc undecenylate. More suitable malodor counteracting ingredients are those described in US 2013/0101544 and 2013/0101545.

The density of the capsule slurry and/or the oil core can be adjusted so that the capsule composition has a substantially uniform distribution of the capsules using known density modifiers or technologies such as those described in Patent Application Publications WO 2000/059616, EP 1 502 646, and EP 2 204 155. Suitable density modifiers include hydrophobic materials and materials having a desired molecular weight (e.g., higher than about 12,000), such as silicone oils, petrolatums, vegetable oils, especially sunflower oil and rapeseed oil, and hydrophobic solvents having a desired density (e.g., less than about 1,000 Kg/m$^3$ at 25° C., such as limonene and octane.

In some embodiments, a stabilizer (e.g., a colloidal stabilizer) is added to a capsule composition to stabilize the emulsion and/or capsule slurry. Examples of colloidal stabilizers are polyvinyl alcohol, cellulose derivatives such hydroxyethyl cellulose, polyethylene oxide, copolymers of polyethylene oxide and polyethylene or polypropylene oxide, or copolymers of acrylamide and acrylic acid.

Viscosity control agents (e.g., suspending agents), which may be polymeric or colloidal (e.g., modified cellulose polymers such as methylcellulose, hydroxyethylcellulose, hydrophobically modified hydroxyethylcellulose, and cross-linked acrylate polymers such as Carbomer, hydrophobically modified polyethers) can be included in the capsule composition, in the capsule core or wall, or in the capsule slurry outside the capsules. Optionally, silicas, either hydrophobic or hydrophilic, can be included at a concentration from about 0.01% to about 20%, more preferable from 0.5% to about 5%, by the weight of the capsule composition.

Examples of hydrophobic silicas include silanols, surfaces of which are treated with halogen silanes, alkoxysilanes, silazanes, and siloxanes, such as SIPERNAT D17, AEROSIL R972 and R974 available from Degussa. Exemplary hydrophilic silicas are AEROSIL 200, SIPERNAT 22S, SIPERNAT 50S (available from Degussa), and SYLOID 244 (available from Grace Davison).

One or more humectants are optionally included to hold water in the capsule composition for a long period of time. Examples include glycerin, propylene glycol, alkyl phosphate esters, quaternary amines, inorganic salts (e.g., potassium polymetaphosphate, sodium chloride, etc.), polyethylene glycols, and the like.

Further suitable humectants, as well as viscosity control/suspending agents, are disclosed in U.S. Pat. Nos. 4,428,869, 4,464,271, 4,446,032, and 6,930,078. Details of hydrophobic silicas as a functional delivery vehicle of active materials other than a free flow/anticaking agent are disclosed in U.S. Pat. Nos. 5,500,223 and 6,608,017.

In some embodiments, one or more pH modifiers are included in the capsule composition to adjust the pH value of the capsule slurry and/or the capsule cores. The pH modifiers can also assist in the formation of capsule walls by changing the reaction rate of the crosslinking reactions that form the capsule walls. Exemplary pH modifiers include metal hydroxides (e.g., LiOH, NaOH, KOH, and Mg(OH)$_2$), metal carbonates and bicarbonates (CsCO$_3$Li$_2$CO$_3$, K$_2$CO$_3$, NaHCO$_3$, and CaCO$_3$), metal phosphates/hydrogen phosphates/dihydrogen phosphates, metal sulfates, ammonia, mineral acids (HCl, H$_2$SO$_4$, H$_3$PO$_4$, and HNO$_3$), carboxylic acids (e.g., acetic acid, citric acid, lactic acid, benzoic acid, and sulfonic acids), and amino acids.

The capsule compositions of this invention can also include one or more non-confined unencapsulated active materials from about 0.01% to about 50%, more preferably from about 5% to about 40%.

The level of solvent materials, particles, adjuncts, or core modifiers can be greater than about 10% (e.g., greater than about 30% and greater than about 70%). In addition to the solvent, it is preferred that higher C log P fragrance materials are employed. It is preferred that greater than about 60 weight percent, preferably greater than 80 and more preferably greater than about 90 weight percent of the fragrance chemicals have C log P values of greater than about 3.3, preferably greater than about 4 and most preferably greater than about 4.5. Those with skill in the art will appreciate that many formulations can be created employing various solvents and fragrance chemicals. The use of a high level of high C log P fragrance chemicals will likely require a lower level of hydrophobic solvent than fragrance chemicals with lower C log P to achieve similar performance stability. As those with skill in the art will appreciate, in a highly preferred embodiment, high C log P fragrance chemicals and hydrophobic solvents comprise greater than about 80, preferably more than about 90 and most preferably greater than 95 weight percent of the fragrance composition. As discussed above, specific C log P values may be measured between candidate solvents and water for the fragrance materials to be included in the core. In this way, an optimum solvent choice may be made. In fact, since most fragrances will have many ingredients, it may be preferable to measure the partitioning of a specific fragrance blend in solvent and water in order to determine the effect of any material interactions.

In addition to the capsules and adjunct materials described above, the capsule composition of this invention can contain one or more other delivery compositions such as polymer-assisted delivery compositions (see U.S. Pat. No. 8,187,580), fiber-assisted delivery compositions (US 2010/0305021), cyclodextrin host guest complexes (U.S. Pat. No. 6,287,603 and US 2002/0019369), pro-fragrances (WO 2000/072816 and EP 0 922 084), and any combination thereof.

Deposition Aids. Deposition aids can also be used to aid in deposition of capsules to surfaces such as fabric, hair or skin. These include but are not limited to anionically, cationically, nonionically, or zwitterionically charged water-soluble polymers which can be applied to the polyurea or polyurethane capsule. This water-soluble polymer can also be an amphoteric polymer with a ratio of cationic and anionic functionalities resulting in a net total charge of zero and positive, i.e., cationic. Those skilled in the art would appreciate that the charge of these polymers can be adjusted by changing the pH, depending on the product in which this technology is to be used. Any suitable method for coating the deposition aids onto the encapsulated fragrance materials can be used. The nature of suitable polymers for assisted capsule delivery to interfaces depends on the compatibility with the capsule wall chemistry since there has to be some association to the capsule wall. This association can be through physical interactions, such as hydrogen bonding, ionic interactions, hydrophobic interactions, electron transfer interactions or, alternatively, the polymer coating could be chemically (covalently) grafted to the capsule or particle surface. Chemical modification of the capsule or particle surface is another way to optimize anchoring of the polymer coating to capsule or particle surface. Furthermore, the capsule and the polymer need to want to go to the desired interface and, therefore, need to be compatible with the chemistry (polarity, for instance) of that interface. Therefore, depending on which capsule chemistry and interface (e.g., cotton, polyester, hair, skin, wool), the polymer can be selected from one or more polymers with an overall zero (amphoteric: mixture of cationic and anionic functional groups) or net positive charge, based on the following polymer backbones: polysaccharides, polypeptides, polycarbonates, polyesters, polyolefinic (vinyl, acrylic, acrylamide, poly diene), polyester, polyether, polyurethane, polyoxazoline, polyamine, silicone, polyphosphazine, olyaromatic, poly heterocyclic, or polyionene, with molecular weight (MW) ranging from about 1,000 to about 1000,000,000, preferably from about 5,000 to about 10,000,000. As used herein, molecular weight is provided as weight average molecular weight.

Particular examples of cationic polymers that can be used to coat the polyurea or polyurethane capsule include, e.g., polysaccharides such as guar, alginates, starch, xanthan, chitosan, cellulose, dextrans, arabic gum, carrageenan, and hyaluronates. These polysaccharides can be employed with cationic modification and alkoxy-cationic modifications such as cationic hydroxyethyl or cationic hydroxypropyl. For example, cationic reagents of choice are 3-chloro-2-hydroxypropyl trimethylammonium chloride or its epoxy version. Another example is graft-copolymers of polyDADMAC on cellulose, e.g., CELQUAT L-200 (POLYQUATERNIUM-4), POLYQUATERNIUM-10 and POLYQUATERNIUM-24, commercially available from National Starch, Bridgewater, N.J. Alternatively, polysaccharides can be employed with aldehyde, carboxyl, succinate, acetate, alkyl, amide, sulfonate, ethoxy, propoxy, butoxy, and combinations of these functionalities; or any hydrophobic modification (compared to the polarity of the polysaccharide backbone). The above modifications can be in any ratio and the degree of functionalization can be up to complete substitution of all functionalizable groups, as long as the theoretical net charge of the polymer is zero (mixture of cationic and anionic functional groups) or preferably positive. Furthermore, up to 5 different types of functional groups may be attached to the polysaccharides. Also, polymer graft chains may be differently modified to the backbone. The counterions can be any halide ion or organic counter ion. See U.S. Pat. Nos. 6,297,203 and 6,200,554.

Another source of cationic polymers contain protonatable amine groups so that the overall net charge is zero (amphoteric: mixture of cationic and anionic functional groups) or positive. The pH during use will determine the overall net charge of the polymer. Examples include silk protein, zein, gelatin, keratin, collagen and any polypeptide, such as polylysine.

Further cationic polymers include polyvinyl polymers with up to 5 different types of monomers can be used. The monomers of such polymer have the generic formula:

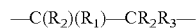

wherein, $R_1$ is any alkane from C1-C25 or H, wherein the number of double bonds ranges from 0-5, $R_1$ is an alkoxylated fatty alcohol with any alkoxy carbon-length of C1-C25, or $R_1$ is a liquid crystalline moiety that can provide the polymer with thermotropic liquid crystalline properties $R_2$ is H or $CH_3$; and $R_3$ is —Cl, —$NH_2$ (i.e., polyvinyl amine or its copolymers with N-vinyl formamide.

Such polyvinyl polymers are sold under the name LUPAMIN 9095 by BASF Corporation. Further suitable cationic polymers containing hydroxylalkylvinylamine units, as disclosed in U.S. Pat. No. 6,057,404.

Another class of materials are polyacrylates with up to 5 different types of monomers. Monomers of polyacrylates have the generic formula:

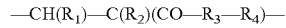

wherein, $R_1$ is any alkane from C1-C25 or H with number of double bonds from 0-5, $R_1$ is an alkoxylated fatty alcohol with a C1-C25 alkyl chain length, or $R_1$ is a liquid crystalline moiety that provides the polymer with thermotropic liquid crystalline properties;

$R_2$ is H or $CH_3$;

$R_3$ is a C1-25 alkyl alcohol or an alkylene oxide with any number of double bonds, or $R_3$ may be absent such that the C=O bond is (via the C-atom) directly connected to $R_4$; and $R_4$ can be —$NH_2$, —$NHR_1$, —$NR_1R_2$, —$NR_1R_2R_6$ (where $R_6$=$R_1$, $R_2$, or —$CH_2$—COOH or its salt), —NH—C(O)—, sulfobetaine, betaine, polyethylene oxide, poly(ethyleneoxide/propylene oxide/butylene oxide) grafts with any end group, H, OH, styrene sulfonate, pyridine, quaternized pyridine, alkyl-substituted pyrrolidone or pyridine, pyridine-N-oxide, imidazolinium halide, imidazolium halide, imidazol, piperidine, —$OR_1$, —OH, —COOH alkali salt, sulfonate, ethoxy sulphate, pyrrolidone, caprolactam, phenyl-$R_4$ or naphthalene-$R_5$, where $R_4$ and $R_5$ are $R_1$, $R_2$, $R_3$, sulfonic acid or its alkali salt or organic counter ion. Also, glyoxylated cationic polyacrylamides can be used. Typical polymers of choice are those containing the cationic monomer dimethylaminoethyl methacrylate (DMAEMA) or methacrylamidopropyl trimethyl ammonium chloride (MAPTAC). DMAEMA can be found in GAFQUAT and GAFFIX VC-713 polymers from ISP. MAPTAC can be found in BASF's LUVIQUAT PQ11 PN and ISP's GAFQUAT HS100.

Another group of polymers that can be used are those that contain cationic groups in the main chain or backbone. Included in this group are:

i) polyalkylene imines such as polyethylene imine, commercially available as LUPASOL from BASF. Any molecular weight and any degree of crosslinking of this polymer can be used in the present invention;

ii) ionenes as disclosed in U.S. Pat. Nos. 4,395,541 and 4,597,962;

iii) adipic acid/dimethyl amino hydroxypropyl diethylene triamine copolymers, such as CARTARETIN F-4 and F-23, commercially available from Sandoz;

iv) polymers of the general formula: —[N(CH$_3$)$_2$—(CH$_2$)$_x$—NH—(CO)—NH—(CH$_2$)$_y$—N(CH$_3$)$_2$—(CH$_2$)$_z$—O—(—CH$_2$)$_p$]$_n$—, with x, y, z, p=1-12, and n according to the molecular weight requirements. Examples are Polyquaternium 2 (MIRAPOL A-15), Polyquaternium-17 (MIRAPOL AD-1), and Polyquatemium-18 (MIRAPOL AZ-1). Other polymers include cationic polysiloxanes and cationic polysiloxanes with carbon-based grafts with a net theoretical positive charge or equal to zero (mixture of cationic and anionic functional groups). This includes cationic end-group functionalized silicones (i.e., Polyquaternium-80). Silicones with general structure: —Si(R$_1$)(R$_2$)—O—]$_x$—[Si(R$_3$)(R$_2$)—O—]$_y$— where R$_1$ is any alkane from C1-C25 or H with number of double bonds from 0-5, aromatic moieties, polysiloxane grafts, or mixtures thereof. R$_1$ can also be a liquid crystalline moiety that can provide the polymer with thermotropic liquid crystalline properties. R$_2$ can be H or CH$_3$; and R$_3$ can be —R$_1$—R$_4$, where R$_4$ can be —NH$_2$, —NHR$_1$, —NR$_1$R$_2$, —NR$_1$R$_2$R$_6$ (where R$_6$=R$_1$, R$_2$, or —CH$_2$—COOH or its salt), —NH—C(O)—, —COOH, —COO— alkali salt, any C1-25 alcohol, —C(O)—NH$_2$ (amide), —C(O)—N(R$_2$)(R$_2$')(R$_2$"), sulfobetaine, betaine, polyethylene oxide, poly(ethyleneoxide/propylene oxide/butylene oxide) grafts with any end group, H, —OH, styrene sulfonate, pyridine, quaternized pyridine, alkyl-substituted pyrrolidone or pyridine, pyridine-N-oxide, imidazolinium halide, imidazolium halide, imidazol, piperidine, pyrrolidone, caprolactam, sulfonate, ethoxysulphate phenyl-R$_5$ or naphthalene-R$_6$ where R$_5$ and R$_6$ are R$_1$, R$_2$, R$_3$, sulfonic acid or its alkali salt or organic counter ion. R$_3$ can also be —(CH$_2$)$_x$—O—CH$_2$—CH(OH)—CH$_2$—N(CH$_3$)$_2$—CH$_2$—COOH and its salts. Any mixture of these R$_3$ groups can be selected. X and y can be varied as long as the theoretical net charge of the polymer is zero (amphoteric) or positive. In addition, polysiloxanes containing up to 5 different types of monomeric units may be used. Examples of suitable polysiloxanes are found in U.S. Pat. Nos. 4,395,541 4,597,962 and 6,200,554. Another group of polymers that can be used to improve capsule/particle deposition are phospholipids that are modified with cationic polysiloxanes. Examples of these polymers are found in U.S. Pat. No. 5,849,313, WO Patent Application 95/18096A1 and European Patent EP0737183B1.

Furthermore, copolymers of silicones and polysaccharides and proteins can be used (e.g., those commercially available as CRODASONE brand products).

Another class of polymers includes polyethylene oxide-co-propyleneoxide-co-butylene oxide polymers of any ethylene oxide/propylene oxide/butylene oxide ratio with cationic groups resulting in a net theoretical positive charge or equal to zero (amphoteric). Examples of such polymers are the commercially available TETRONIC brand polymers.

Suitable polyheterocyclic (the different molecules appearing in the backbone) polymers include the piperazine-alkylene main chain copolymers disclosed by Kashiki and Suzuki (1986) *Ind. Eng. Chem. Fundani.* 25:120-125.

As indicated, the addition of hydrophobic polymers to the core can also improve stability by slowing diffusion of the fragrance from the core. The level of polymer is normally less than 80% of the core by weight, preferably less than 50%, and most preferably less than 20%. The basic requirement for the polymer is that it be miscible or compatible with the other components of the core, namely the fragrance and other solvent. Preferably, the polymer also thickens or gels the core, thus further reducing diffusion.

Any compound, polymer, or agent discussed above can be the compound, polymer, or agent itself as shown above, or its salt, precursor, hydrate, or solvate. A salt can be formed between an anion and a positively charged group on the compound, polymer, or agent. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group on the compound, polymer, or agent. Suitable cations include sodium ion, potassium ion, magnesium ion, calcium ion, and an ammonium cation (e.g., tetramethylammonium ion). A precursor can be ester and another suitable derivative, which, during the process of preparing a polyurea or polyurethane capsule composition of this invention, is capable of converting to the compound, polymer, or agent and being used in preparing the polyurea or polyurethane capsule composition. A hydrate refers to the compound, polymer, or agent that contains water. A solvate refers to a complex formed between the compound, polymer, or agent and a suitable solvent. A suitable solvent can be water, ethanol, isopropanol, ethyl acetate, acetic acid, and ethanolamine. Certain compounds, polymers, and agents have one or more stereocenters, each of which can be in the R configuration, the S configuration, or a mixture. Further, some compounds, polymers, and agents possess one or more double bonds wherein each double bond exists in the E (trans) or Z (cis) configuration, or combinations thereof. The compounds, polymers, and agents include all possible configurational stereoisomeric, regioisomeric, diastereomeric, enantiomeric, and epimeric forms as well as any mixtures thereof. As such, lysine used herein includes L-lysine, D-lysine, L-lysine monohydrochloride, D-lysine monohydrochloride, lysine carbonate, and so on. Similarly, arginine includes L-arginine, D-arginine, L-arginine monohydrochloride, D-arginine monohydrochloride, arginine carbonate, arginine monohydrate, and etc. Guanidine includes guanidine hydrochloride, guanidine carbonate, guanidine thiocyanate, and other guanidine salts including their hydrates. Ornithine include L-ornithine and its salts/hydrates (e.g., monohydrochloride) and D-ornithine and its salts/hydrates (e.g., monohydrochloride).

In accordance with the compositions and methods disclosed herein, the wall polymer level of the polyurea/polyurethane capsules can be from about 0.1% to about 15% of the total capsule suspension, preferably from about 1% to about 10% of the total capsule suspension, or more preferably from about 2% to about 5% of the total capsule suspension.

In a further embodiment of the invention, the amount of encapsulated active material is from about 5% to about 80% of the total capsule suspension, preferably from about 10% to about 60% of the total capsule suspension, or most preferably from about 20% to about 50% of the total capsule suspension.

In certain embodiments of the invention, the capsule slurry is cured at a temperature greater than about 55° C.; greater than about 65° C.; greater than about 75° C.; greater than about 85° C.; greater than about 95° C.; greater than about 105° C. or greater than 120° C.

Capsules prepared in accordance with this invention preferably have a size in the range of from 0.01 to 1000 microns (e.g., 0.5 to 150 microns and 2 to 15 microns). The capsule distribution can be narrow, broad, or multi-modal.

In some embodiments, the capsule compositions prepared in accordance with the present invention is subsequently purified. Purification can be achieved by washing with water, diafiltration, and centrifugation. Suitable diafiltration processes are those described in US Patent Application Publication 2014/0134242 and Sheth et al., J. of Membr. Sci. 2003, 211.2, 251-61. The capsule slurry can also be washed with water until a neutral pH in the capsule slurry is achieved. For the purposes of the present invention, the capsule compositions can be washed using any conventional method including the use of a separatory funnel, filter paper, centrifugation and the like. The capsule suspension can be washed one, two, three, four, five, six, seven, eight, nine, ten or more times until a neutral pH, i.e., pH 7±0.5, is achieved. The pH of the purified capsules can be determined using any conventional method including, but not limited to pH paper, pH indicators, or a pH meter.

A capsule suspension of this invention is "purified" in that it is 80%, 90%, 95%, 97%, 98% or 99% homogeneous to capsules. In accordance with the present invention, purity is achieved by washing the capsules until a neutral pH is achieved, which is indicative of removal of unwanted impurities and/or starting materials, e.g., polyisocyanate, cross-linking agent and the like.

In certain embodiments of this invention, the purification of the capsules includes the additional step of adding a salt to the capsule suspension prior to the step of washing the capsule suspension with water. Exemplary salts of use in this step of the invention include, but are not limited to, sodium chloride, potassium chloride or bi-sulphite salts.

Applications. The capsule compositions of the present invention are well-suited for use in personal care products including, without limitation, deodorants and antiperspirants, shampoos, hair conditioners, hair rinses, hair refreshers, body washes such as shower gels, body locations, body sprays, antiperspirants, deodorants, soaps products and the like. In particular embodiments, the compositions are of use in an aerosol antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant or spray deodorant. Exemplary personal care product formulations are provided in examples below.

The capsule compositions are also well-suited for use in fabric care products such as rinse conditioners and liquid and powder detergents; home care products such as all-purpose cleaners including bathroom cleaners; bath tissues; rug deodorizers; candles; room deodorizers; floor cleaners; disinfectants; window cleaner; and fabric refreshers; personal hygiene products such as hand sanitizers; toiletries; and oral care products such as tooth powder.

Further, the capsule compositions are useful in the following products: (a) household devices including paper towels, disposable wipes, room deodorizers, and fabric softener dryer sheets, (b) baby care products such as diaper rash cream/balm and baby powder, (c) baby care devices, e.g., diapers, bibs, and wipes, (d) health care products including tooth paste, oral rinse, tooth whiteners, denture adhesive, hand sanitizer, and antiinflammatory balms, ointment or spray, (e) health care devices, e.g., dental floss, toothbrushes, feminine hygiene products such as tampons, feminine napkins and wipes, and pantiliners; (f) personal care products including personal cleansers (bar soap, body wash), sunscreen (spray or lotion), wax-based deodorant, glycol/soap type deodorant, lotion, body powder, shave cream, bath soak, exfoliating scrub, (g) personal care devices such as facial tissues and cleansing wipes, (h) hair care products including shampoo (liquid and dry powder), hair conditioner (rinse out and leave-in), hair fixative and styling aids, hair bleaches, dyes and colorants, (i) beauty care like fine fragrance (See, e.g., U.S. Pat. No. 4,428,869), solid perfume, liquid foundation, powder foundation, eye shadow, lipstick/lip balm, (j) confectionaries such as chewing gums, breath fresheners, orally dissolvable strips, chewable candy, hard candy, (k) snacks/breakfast foods, potato, tortilla, vegetable or multigrain chips, popcorn, pretzels, cereal bars, extruded stacks, ready to heat cereal, cooked cereal, (l) beverages including ready to drink liquid drinks, liquid drink concentrates, powder drinks, coffee, tea, alcoholic, (m) spice blends and consumer prepared foods, e.g., powder gravy, sauce mixes, condiments, and fermented products, (n) ready to heat foods including soups, sauces, stews, and frozen entrees, and (o) dairy products soy, nut-milk products such as flavored milk beverages, yoghurt, ice cream, bean curd, cheese, and prepared egg products.

The above-listed applications are all well known in the art. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, and 4,767,547, 4,424,134. Liquid laundry detergents include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Liquid dish detergents are described in U.S. Pat. Nos. 6,069,122 and 5,990,065. Shampoo and conditioners that can employ the present invention include those described in U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681. Automatic Dish Detergents are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562.

The invention is described in greater detail by the following non-limiting examples.

EXAMPLE 1

Preparation of Polyurea Capsules with TAKENATE D-110N

Preparation of the Fragrance Emulsion. Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals Corporation, Rye Brook, N.Y.), to form the oil phase. In a separate beaker, a 1.0% surfactant solution (160 g) was prepared by dissolving sufficient amount of FLEXAN II (Akzo Nobel, Bridgewater, N.J.) in deionized (DI) water. The oil phase was then emulsified into the aqueous phase to form the fragrance emulsion under shearing (ULTRA TURRAX, T25 Basic, and IKA WERKE) at 6500 rpm for two minutes.

Formation of Fragrance Capsules. The fragrance emulsion was heated to 35° C. in a round bottom vessel and 10.4 g of 56% tris(2-aminoethyl)amine (Sigma-Aldrich, St. Louis, Mo.) was added under constant mixing with an overhead mixer. Formation of capsule was immediately visible by optical microscopy. The mixer speed was reduced after the addition of tris(2-aminoethyl)amine was complete. The capsule slurry was cured at 55° C. for two hours.

EXAMPLE 2

Polyurea Capsules Cured at Elevated Temperature

Preparation of the Fragrance Emulsion. Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals Corporation, Rye Brook, N.Y.), to form the oil phase. In a separate beaker, a 1.0% surfactant solution (160 g) was prepared by dissolving sufficient amount of FLEXAN II (Akzo Nobel, Bridgewater, N.J.) in Water. The oil phase was then emulsified into the aqueous phase to form the fragrance emulsion under shearing (ULTRA TURRAX, T25 Basic, and IKA WERKE) at 6500 rpm for two minutes.

Formation of Fragrance Capsules. The fragrance emulsion was heated to 35° C. in a round bottom vessel and 10.4 g of 56% tris(2-aminoethyl)amine (Sigma-Aldrich, St. Louis, Mo.) was added under constant mixing with an overhead mixer. Formation of capsules was immediately visible by optical microscopy. The mixer speed was reduced after the addition of tris(2-aminoethyl)amine was complete. The temperature was raised to 55° C. and kept at 55° C. for 2 hours and elevated to 75° C. for 2 hours.

EXAMPLE 3

Polyurea Capsules Prepared with a Blend of Dispersants

Preparation of the Fragrance Emulsion. Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals Corporation, Rye Brook, N.Y.), to form the oil phase. In a separate beaker, a solution (130 g) containing 1.0% of FLEXAN II (Akzo Nobel, Bridgewater, N.J.) was mixed with a solution (30 g) of 1% CMC in Water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules. The fragrance emulsion was heated to 35° C. in a round bottom vessel and 10.4 g of 56% tris(2-aminoethyl)amine (Sigma-Aldrich, St. Louis, Mo.) was added under constant mixing with an overhead mixer. Formation of capsules was immediately visible by optical microscopy. The mixer speed was reduced after the addition of tris(2-aminoethyl)amine was complete. The capsule slurry was cured at 55° C. for two hours.

EXAMPLE 4

Preparation of Polyurea Capsules with DESMODUR L75

Polyurea capsules were prepared with DESMODUR L75 by carrying out the process described in Example 1 and replacing TAKENATE D-110N with DESMODUR L75.

EXAMPLE 5

Polyurea Capsule with Elevated Amounts of Isocyanate Precursors and Amine Crosslinkers Preparation of the Fragrance Emulsion. Ninety-six grams of a fragrance, Greenfields (International Flavors and Fragrance, Union Beach, N.J.) was weighed out and combined with 24 g of NEOBEE oil (Stepan, Chicago, Ill.) and 14.4 g of isocyanate monomer, TAKENATE D-110N (Mitsui Chemicals Corporation, Rye Brook, N.Y.), to form the oil phase. In a separate beaker, a 1.0% surfactant solution (150 g) was prepared by dissolving sufficient amount of FLEXAN II (Akzo Nobel, Bridgewater, N.J.) in Water. The oil phase was then emulsified into the aqueous phase to form the fragrance emulsion under shearing (ULTRA TURRAX, T25 Basic, and IKA WERKE) at 6500 rpm for two minutes.

Formation of Fragrance Capsules. The fragrance emulsion was placed in a round bottom vessel and 15.6 g of 56% tris(2-aminoethyl)amine (Sigma-Aldrich, St. Louis, Mo.) was added under constant mixing with an overhead mixer. Formation of capsules was immediately visible by optical microscopy. The mixer speed was reduced after the addition of tris(2-aminoethyl)amine was complete. The capsule slurry was cured at 55° C. for two hours.

EXAMPLE 6

Polyurea Capsules Prepared with Diethylenetriamine

Preparation of the Fragrance Emulsion. Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals Corporation, Rye Brook, N.Y., USA), to form the oil phase. In a separate beaker, a solution (130 g) containing 1.0% of FLEXAN II (Akzo Nobel, Bridgewater, N.J.) was mixed with a solution (30 g) of 1% CMC in Water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules. The fragrance emulsion was heated to 35° C. in a round bottom vessel and 10.4 g of 40% diethylenetriamine (Sigma-Aldrich, St. Louis, Mo.) was added under constant mixing with an overhead mixer. Formation of capsules was immediately visible by optical microscopy. The mixer speed was reduced after the addition of diethylenetriamine was complete. The capsule slurry was cured at 55° C. for two hours.

EXAMPLE 7

Polyurea Capsules Prepared with Triethylenetetramine

Preparation of the Fragrance Emulsion. Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals Corporation, Rye Brook, N.Y.), to form the oil phase. In a separate beaker, a solution (130 g) containing 1.0% of FLEXAN II (Akzo Nobel, Bridgewater, N.J.) was mixed with a solution (30 g) of 1% CMC in Water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules. The fragrance emulsion was heated to 35° C. in a round bottom vessel and 10.4 g of 70% triethylenetetramine (Sigma-Aldrich, St. Louis, Mo.) was added under constant mixing with an overhead mixer. Formation of capsules was immediately visible by optical microscopy. The mixer speed was reduced after the addition of triethylenetetramine was complete. The capsule slurry was cured at 55° C. for two hours.

EXAMPLE 8

Polyurea Capsules Prepared with Tetraethylenepentamine

Preparation of the Fragrance Emulsion. Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals Corporation, Rye Brook, N.Y.), to form the oil phase. In a separate beaker, a solution (130 g) containing 1.0% of FLEXAN II (Akzo Nobel, Bridgewater, N.J.) was mixed with a solution (30 g) of 1% CMC in Water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules. The fragrance emulsion was heated to 35° C. in a round bottom vessel and 10.4 g of 70% tetraethylenepentamine (Sigma-Aldrich, St. Louis, Mo.) was added under constant mixing with an overhead mixer. Formation of capsules was immediately visible by optical microscopy. The mixer speed was reduced after the addition of tetraethylenepentamine was complete. The capsule slurry was cured at 55° C. for two hours.

EXAMPLE 9

Polyurea Capsules Prepared with Pentaethylenehexamine

Preparation of the Fragrance Emulsion. Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals Corporation, Rye Brook, N.Y.), to form the oil phase. In a separate beaker, a solution (130 g) containing 1.0% of FLEXAN II (Akzo Nobel, Bridgewater, N.J.) was mixed with a solution (30 g) of 1% CMC in Water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules. The fragrance emulsion was heated to 35° C. in a round bottom vessel and 10.4 g of 70% pentaethylenehexamine (Sigma-Aldrich, St. Louis, Mo.) was added under constant mixing with an overhead mixer. Formation of capsules was immediately visible by optical microscopy. The mixer speed was reduced after the addition of pentaethylenehexamine was complete. The capsule slurry was cured at 55° C. for two hours.

EXAMPLE 10

Polyurea Capsules Prepared with Branched Polyethyleneimide

Preparation of the Fragrance Emulsion. Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals Corporation, Rye Brook, N.Y.), to form the oil phase. In a separate beaker, a solution (130 g) containing 1.0% of FLEXAN II (Akzo Nobel, Bridgewater, N.J.) was mixed with a solution (30 g) of 1% CMC in Water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules. The fragrance emulsion was heated to 35° C. in a round bottom vessel and 10.4 g of 49% branched polyethyleneimide (Sigma-Aldrich, St. Louis, Mo.) was added under constant mixing with an overhead mixer. Formation of capsules was immediately visible by optical microscopy. The mixer speed was reduced after the addition of branched polyethyleneimide was complete. The capsule slurry was cured at 55° C. for two hours.

EXAMPLE 11

Polyurea Capsules Prepared with Nisin

Preparation of the Fragrance Emulsion. Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals Corporation, Rye Brook, N.Y.), to form the oil phase. In a separate beaker, a solution (120 g) containing 1.0% of MOWIOL 3-83 (Kuraray America Inc., Houston, Tex.) was mixed with a solution (30 g) of 1% CMC in Water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules. The fragrance emulsion was heated to 35° C. in a round bottom vessel and a mixture containing 20.1 g of 60% Nisin (Sigma-Aldrich, St. Louis, Mo.) and 0.3 g catalyst, DABCO Crystalline (1,4-diazabicyclo[2.2.2]octane) (Dow Chemical, Midland, Mich.), was added under constant mixing with an overhead mixer. Formation of capsules was immediately visible by optical microscopy. The mixer speed was reduced after the addition of Nisin was complete. The capsule slurry was cured at 75° C. for two hours.

EXAMPLE 12

Polyurea Capsules Prepared with 1,3-Diaminoguanidine Monohydrochloride

Preparation of the Fragrance Emulsion. Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals Corporation, Rye Brook, N.Y.), to form the oil phase. In a separate beaker, a solution (120 g) containing 1.0% of MOWIOL 3-83 (Kuraray America Inc., Houston, Tex.) was mixed with a solution (30 g) of 1% CMC in Water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules. The fragrance emulsion was heated to 35° C. in a round bottom vessel and a mixture containing 10.1 g of 48% 1,3-diaminoguanidine monohydrochloride (Sigma-Aldrich, St. Louis, Mo.), 10 g of 50% sodium carbonate (Sigma-Aldrich, St. Louis, Mo.) and 0.3 g catalyst, DABCO Crystalline (1,4-diazabicyclo[2.2.2]octane) (Dow Chemical, Midland, Mich.), was added under constant mixing with an overhead mixer. Formation of capsules was immediately visible by optical microscopy. The mixer speed was reduced after the addition of 1,3-diaminoguanidine monohydrochloride was complete. The capsule slurry was cured at 75° C. for two hours.

EXAMPLE 13

Polyurea Capsules Prepared with 1,1-Dimethylbiguanide Hydrochloride

Preparation of the Fragrance Emulsion. Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENATE D-110N (Mitsui Chemicals Corporation, Rye Brook, N.Y.), to form the oil phase. In a separate beaker, a solution (120 g) containing 1.0% of MOWIOL 3-83 (Kuraray America Inc., Houston, Tex.) was mixed with a solution (30 g) of 1% CMC in Water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules. The fragrance emulsion was heated to 35° C. in a round bottom vessel and a mixture containing 10.1 g of 46% 1,1-dimethylbiguanide hydrochloride (Santa Cruz Biotechnology, Dallas, Tex.), 10 g of 50% sodium carbonate (Sigma-Aldrich, St. Louis, Mo.) and 0.3 g catalyst, DABCO Crystalline (1,4-diazabicyclo[2.2.2]octane) (Dow Chemical, Midland, Mich.), was added under constant mixing with an overhead mixer. Formation of capsules was immediately visible by optical microscopy. The mixer speed was reduced after the addition of 1,1-dimethylbiguanide hydrochloride was complete. The capsule slurry was cured at 75° C. for two hours.

EXAMPLE 14

Polyurea Capsules Prepared with Guanidine Carbonate

Preparation of the Fragrance Emulsion. Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, TAKENA D-110N (Mitsui Chemicals corporation, Rye Brook, N.Y.), to form the oil phase. In a separate beaker, a solution (130 g) containing 1.0% of MOWIOL 3-83 (Kuraray America Inc., Houston, Tex.) was mixed with a solution (30 g) of 1% CMC in Water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules. The fragrance emulsion was heated to 35° C. in a round bottom vessel and a mixture containing 10.1 g of 36% guanidine carbonate (Sigma-Aldrich, St. Louis, Mo.) and 0.3 g catalyst, DABCO Crystalline (1,4-diazabicyclo[2.2.2]octane) (Dow Chemical, Midland, Mich.), was added under constant mixing with an overhead mixer. Formation of capsules was immediately visible by optical microscopy. The mixer speed was reduced after the addition of guanidine carbonate was complete. The capsule slurry was cured at 75° C. for two hours.

EXAMPLE 15

Physical Characterization of Polyurea Capsules

Figure 1B:
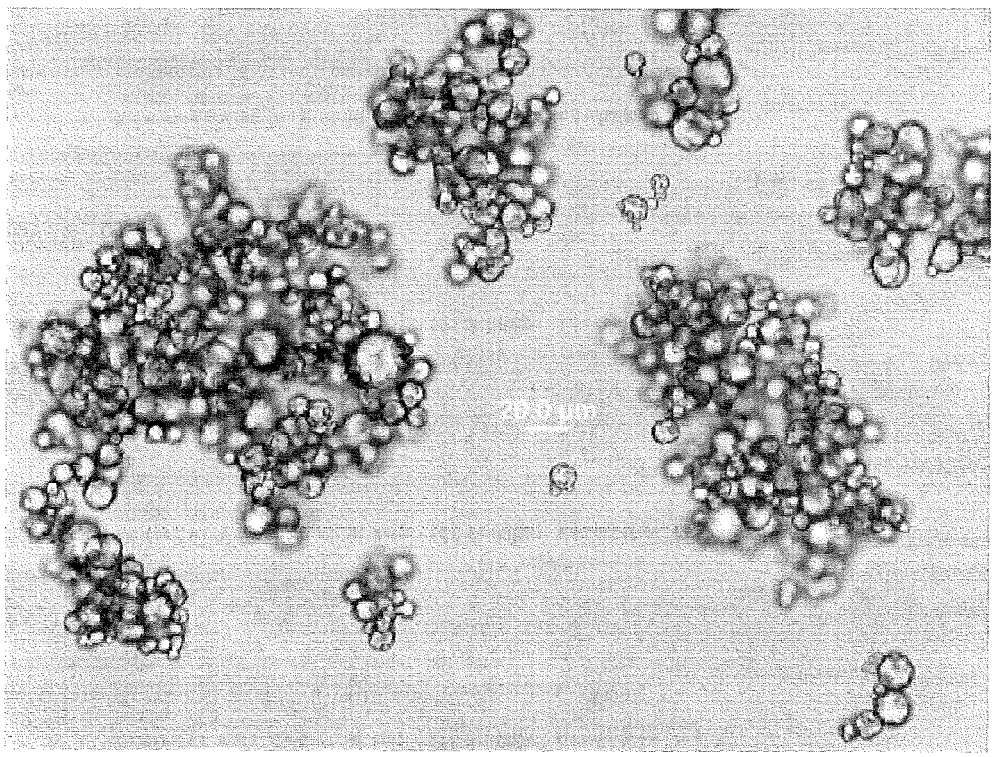
FIG. 1B shows an optical image of capsules prepared in accordance with the present invention.

The capsules prepared in Example 5 were analyzed with scanning electron microscopy (FIG. 1A) and optical microscopy (FIG. 1B). It was found that the capsules prepared in accordance with the present invention have robust mechanical stability.

EXAMPLE 16

Fragrance Leakage from Polyurea Capsules

The capsule slurries prepared in Examples 3-15 were analyzed for fragrance leakage. The fragrance capsule slurries were diluted with DOWNY fabric softener (Procter & Gamble, Cincinnati, Ohio) to yield mixtures containing 0.5% capsule slurry. The mixtures were aged in an oven for 0, 3 and 6 days at 50° C. Three samples were prepared by filtering the mixtures through 1 μm filters (Fisher Scientific, Pittsburgh, Pa.). The content of free fragrance in the mixtures was analyzed. The results are presented in Table 1.

TABLE 1

| | | Percent Leakage | | |
| --- | --- | --- | --- | --- |
| Sample | FO (%) | 0 days | 3 days @ 50° C. | 6 days @ 50° C. |
| Example 3 | 2.2 | <10 | 1 | 11 |
| Example 5 | 0.3 | <10 | <10 | <10 |
| Example 6 | 0.4 | <10 | 22 | 29 |
| Example 7 | 0.4 | 15 | 21 | 13 |
| Example 8 | 0.5 | <10 | <10 | 16 |
| Example 9 | 0.9 | <10 | <10 | 13 |
| Example 10 | 0.05 | <10 | <10 | <10 |
| Example 11 | 0.8 | <10 | <10 | <10 |
| Example 12 | 0.4 | <10 | <10 | <10 |
| Example 13 | 0.6 | <10 | <10 | <10 |
| Example 14 | 0.3 | <10 | <10 | <10 |

The results demonstrated that the capsules prepared in accordance with the present method had excellent stability.

EXAMPLE 17

Perfumery Performance of Polyurea Capsules in a Hair Refresher Application

To establish the consumer benefits of the capsules of this invention, the capsule slurry prepared in Example 3 was blended into a hair refresher base and evaluated for its consumer benefits. The fragrance load was 0.25% neat equivalent. For comparison, a similar solution was prepared using neat fragrance at 0.5%. Hair swatches were sprayed with the dispersion and were air-dried overnight before being evaluated by a panel of 12 judges. The fragrance intensity was rated from a scale ranging from 0 to 10. A numerical value of 5 indicated the hair swatches produced a strong intensity, while a value of 10 indicated the hair swatches generated a very strong smell. The results of this analysis are presented in Table 2.

TABLE 2

| Samples | Pre-rubbing intensity | $I_{pre, capsule}/I_{pre, neat}$ | Post-rubbing intensity | $I_{post, capsule}/I_{post, neat}$ |
|---|---|---|---|---|
| Neat | 1.0 | | 1.2 | |
| Sample containing capsule after 24 hours | 2.5 | 2.5 | 6.3 | 5.25 |

The data demonstrated that the samples containing capsules prepared in accordance with this invention gave much stronger perfumery intensity at both the pre-rubbing and post-rubbing stage. The fragrance intensity of the samples containing capsules was 2.5 times that of the neat samples at the pre-rubbing stage and 5.25 that of the neat sample in the post-rubbing stage. This analysis indicated that the polyurea capsule provided significant and long-lasting perfumery benefits and suitable for a personal care application.

EXAMPLE 18

Perfumery Performance of Polyurea Capsules in a Fabric Refresher Application

To establish the consumer benefits of the capsules of this invention, the capsule slurry prepared in Example 3 was blended into a fabric refresher base and evaluated for its consumer benefits. The fragrance load was 0.2% neat equivalent. For comparison, a similar solution was prepared using neat fragrance at 0.2%. Hair swatches were sprayed with the dispersion and air-dried for 72 hours before being evaluated by a panel of 6 judges. The fragrance intensity was rated on a scale ranging from 0 to 10. A numerical value of 5 indicated the hair swatches produced a strong intensity, while a value of 10 indicated the hair swatches generated a very strong smell. The results of the analysis are presented in Table 3.

TABLE 3

| Samples | Pre-rubbing intensity | $I_{pre, capsule}/I_{pre, neat}$ | Post-rubbing intensity | $I_{post, capsule}/I_{post, neat}$ |
|---|---|---|---|---|
| Neat | 1.0 | | 1.0 | |
| Sample containing capsule after 24 hours | 2.0 | 2.0 | 5.5 | 5.50 |

The results demonstrated that the samples containing capsules prepared in accordance with this invention gave much stronger perfumery intensity at both the pre-rubbing and post-rubbing stage. The fragrance intensity of the samples containing capsules was unexpectedly 2 times that of the neat samples at the pre-rubbing stage and 5.5 times that of the neat sample in the post-rubbing stage. This analysis indicated that the polyurea capsule provided significant and long-lasting perfumery benefits and suitable for fabric care application.

EXAMPLE 19

Application Benefit of Polyurea Capsule in Hair Conditioner Application

Application benefit of the instant capsules in a personal care product was evaluated using a hair conditioner formulation. To conduct the experiment, the capsule slurry was dispersed in a hair conditioner base at 0.5% neat fragrance equivalent. The hair conditioner base was a Magick Botanicals oil-free conditioner base. To the base was added 1.0 g polyurea capsules. The formulation was applied to bundles of hair (40 g each), which contained four hair strands. The bundles were subsequently washed by wetting two bundles (8 strands) under water (water temperature: 100 F/38 C; flow rate: 1 gallon/minute) and lightly squeezing off the excess water. The hair was placed onto a balance and 2 g of unfragranced shampoo was directly applied onto the wet hair. The hair was lathered between palms, 10× clockwise and 10× counterclockwise, keeping the wax part of the swatches between two fingers (not to spread wax over surface of hair). The hair swatches were allowed to stand for 15 seconds and subsequently rinsed under a stream of water for 45 seconds. The process was repeated with hair conditioner. Excess water was gently squeezed out and the hair was allowed to dry overnight.

Figure 2:
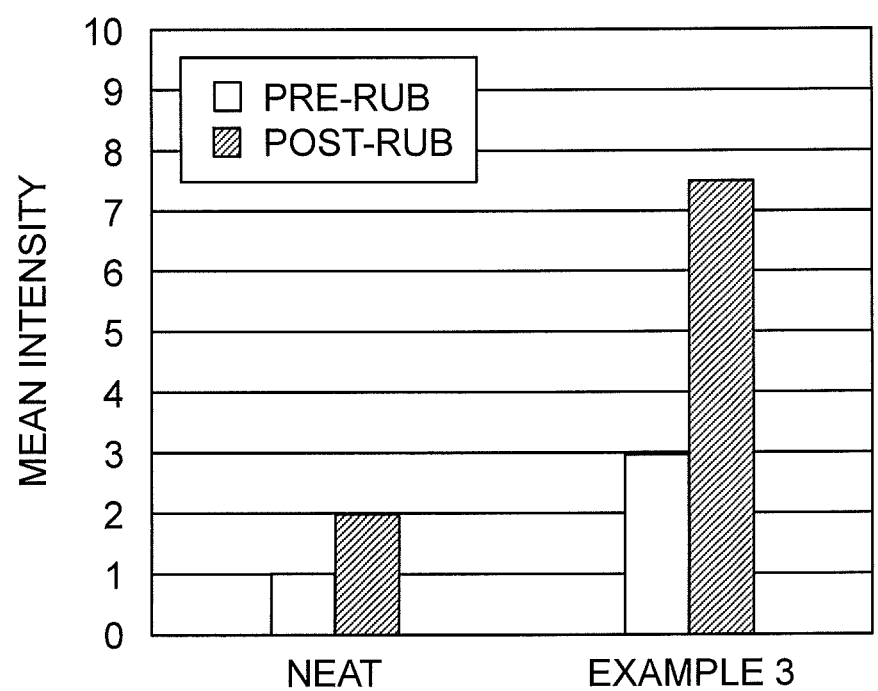
FIG. 2 shows the sensory performance of polyurea capsules of the invention in a hair conditioner formulation.

The dried samples were than evaluated by 16 trained panelists and the results are presented in FIG. 2. The results clearly demonstrate that the product containing polyurea capsules had much stronger perfumery intensity than the neat fragrance. Thus, the polyurea capsules of this invention can deliver excellent consumer benefits both in the pre- and post-rubbing stage.

EXAMPLE 20

Preparation of Polyurea Capsule Using Branched Polyethylenimine

Preparation of the Fragrance Emulsion. Ninety-six grams of a fragrance, Greenfields (International Flavors and Fragrance, Union Beach, N.J.) was weighed out and combined with 24 g of NEOBEE oil M-5 (caprylic/capric triglyceride, Stepan, Chicago, Ill.) and 9.6 g of isocyanate monomer, TAKENATE D110-N (trimethylol propane-adduct of xylylene diisocyanate, Mitsui Chemicals Corporation, Rye Brook, N.Y.), to form the oil phase. In a separate beaker, a solution (130 g) containing 1% of FLEXAN II (polystyrene sulfonate, Akzo Nobel, Bridgewater, N.J.) was mixed with a solution (30 g) of 1% CMC (WALOCEL CRT 50000 PA 07, Dow, Midland, Mich.) in water to form the aqueous phase. The oil phase was then emulsified into the aqueous phase to form a fragrance emulsion under shearing (ULTRA TURRAX, T25 Basic, IKA WERKE) at 6500 rpm for two minutes.

Formation of Fragrance Capsules. The fragrance emulsion was heated to 35° C. in a round bottom vessel and 10.4 g of 49% branched polyethylenimine (Sigma-Aldrich, St. Louis, Mo.) was added under constant mixing with an overhead mixer. Formation of capsules was immediately visible by optical microscopy. The mixer speed was reduced after the addition of branched polyethylenimine was complete. The capsule slurry was cured at 55° C. for two hours.

EXAMPLE 21

Preparation of Polyurea Capsule with PVP and PQ11 as Dispersants

Preparation of the Fragrance Emulsion. Ninety-six grams of a fragrance, Greenfields (International Flavors and Fragrance, Union Beach, N.J.) was weighed out and combined with 24 g of NEOBEE oil M-5 (caprylic/capric triglyceride, Stepan, Chicago, Ill.) and 9.6 g of isocyanate monomer, TAKENATE D110-N (trimethylol propane-adduct of xylylene diisocyanate, Mitsui Chemicals Corporation, Rye Brook, N.Y.), to form the oil phase. In a separate beaker, a solution (122.5 g) containing 0.6% of PVP (polyvinylpyrrolidone, Luviskol ® K 90 Pulver, BASF, Ludwigshafen, Germany) was mixed with a solution (37.5 g) of 20% POLYQUATERNIUM-11 (PQ11, Vinyl pyrrolidone/dimethylaminoethyl methacrylate copolymer, cationic polymer, LUVIQUAT PQ11 AT 1, Ludwigshafen, Germany) in water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules. The fragrance emulsion was heated to 35° C. in a round bottom vessel and 10.4 g of 49% branched polyethylenimine (Sigma-Aldrich, St. Louis, Mo.) was added under constant mixing with an overhead mixer. The mixer speed was reduced after the addition of crosslinker was complete. The capsule slurry was cured at 55° C. for two hours.

EXAMPLE 22

Preparation of Polyurea Capsule with Cross-Linking Agent of a Different Molecular Weight Preparation of the Fragrance Emulsion. Ninety-six grams of a fragrance, Greenfields (International Flavors and Fragrance, Union Beach, N.J.) was weighed out and combined with 24 g of NEOBEE oil M-5 (caprylic/capric triglyceride, Stepan, Chicago, Ill.) and 9.6 g of isocyanate monomer, TAKENATE D110-N (trimethylol propane-adduct of xylylene diisocyanate, Mitsui Chemicals Corporation, Rye Brook, N.Y.), to form the oil phase. In a separate beaker, a solution (130 g) containing 1% of FLEXAN II (polystyrene sulfonate, Akzo Nobel, Bridgewater, N.J.) was mixed with a solution (30 g) of 1% CMC (WALOCEL CRT 50000 PA 07, Dow, Midland, Mich.) in water to form the aqueous phase. The oil phase was then emulsified into the aqueous phase to form the fragrance emulsion under shearing (ULTRA TURRAX, T25 Basic, IKA WERKE) at 6500 rpm for two minutes.

Formation of Fragrance Capsules. The fragrance emulsion was heated to 35° C. in a round bottom vessel and 10.4 g of 49% Lupasol P (multifunctional cationic polyethylenimine; MW 750,000 Da; BASF, Tarrytown, N.Y., USA) was added under constant mixing with an overhead mixer. Formation of capsules was immediately visible by optical microscopy. The mixer speed was reduced after the addition of crosslinker was complete. The capsule slurry was cured at 55° C. for two hours.

EXAMPLE 23

Preparation of Polyurea Capsule Cured at Elevated Temperature

Preparation of the Fragrance Emulsion. Ninety-six grams of a fragrance, Greenfields (International Flavors and Fragrance, Union Beach, N.J.) was weighed out and combined with 24 g of Neobee oil M-5 (caprylic/capric triglyceride, Stepan, Chicago, Ill., USA) and 9.6 g of isocyanate monomer, and Takenate D110-N (trimethylol propane-adduct of xylylene diisocyanate, Mitsui Chemicals corporation, Rye Brook, N.Y., USA) to form the oil phase. In a separate beaker, a 1% surfactant solution (160 g) was prepared by dissolving sufficient amount of Flexan II (polystyrene sulfonate, Akzo Nobel, Bridgewater, N.J., USA) and CMC (carboxymethyl cellulose, WALOCEL CRT 50000 PA 07, Dow, Midland, Mich.) in water. The oil phase was then emulsified into the aqueous phase to form the fragrance emulsion under shearing (Ultra Turrax®, T25 Basic, and IKA® WERKE) at 6500 rpm for two minutes.

Formation of Fragrance Capsules. The fragrance emulsion prepared in step 1 was heated to 35° C. in a round bottom vessel and to which 10.4 g of 49% branched polyethylenimine (Sigma-Aldrich, St. Louis, Mo.) was added under constant mixing with an overhead mixer. Formation of capsule was immediately visible by optical microscopy. The mixer speed was reduced after the addition of crosslinker was complete. The temperature was raised 75° C. and kept at 75° C. for 2 hours.

EXAMPLE 24

Preparation of Polyurea Capsule with Large Amount of Isocyanate and Amine Cross-Linking Agent Preparation of the Fragrance Emulsion. Ninety-six grams of a fragrance, Greenfields (International Flavors and Fragrance, Union Beach, N.J.) was weighed out and combined with 24 g of Neobee oil (Stepan, Chicago, Ill., USA) and 14.4 g of isocyanate monomer, Takenate D110-N (Mitsui Chemicals corporation, Rye Brook, N.Y., USA) to form the oil phase. In a separate beaker, a 1.0% surfactant solution (145 g) was prepared by dissolving sufficient amount of Flexan II (Akzo Nobel, Bridgewater, N.J., USA) in Water. The oil phase was then emulsified into the aqueous phase to form the fragrance emulsion under shearing (Ultra Turrax®, T25 Basic, and IKA® WERKE) at 6500 rpm for two minutes.

Formation of Fragrance Capsules. The fragrance emulsion prepared in step 1 was placed in a round bottom vessel and to which 15.4 g of 50% branched polyethylenimine (Sigma-Aldrich, St. Louis, Mo.) was added under constant mixing with an overhead mixer. Formation of capsule was immediately visible by optical microscopy. The mixer speed was reduced after the addition of crosslinker was complete. The capsule slurry was cured at 55° C. temperature for two hours.

The amounts of the isocyanate and cross-linking agent are about three folds those used in example 20.

EXAMPLE 25

Encapsulation Performance of Polyurea Capsules

Figure 3:
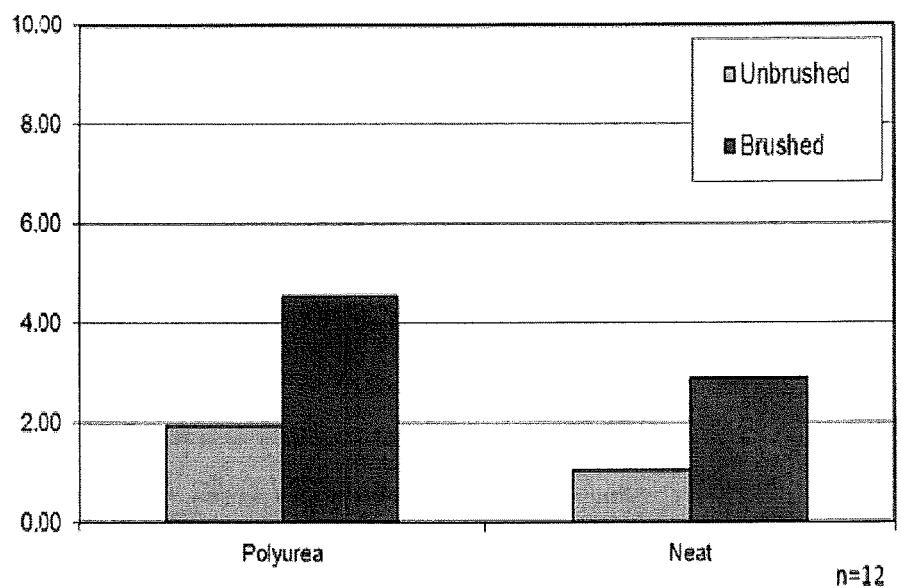
FIG. 3 shows the sensory performance of the polyurea capsule composition prepared in Example 20 in a hair conditioner formulation.

The capsule composition prepared in Example 20 was blended into a model hair conditioner solution. The fragrance load was 0.5% neat equivalent. A comparative solution was prepared with the neat fragrance at 0.5%. The perfumery benefit of the capsules was evaluated by conducting a hair wash experiment using standard protocols. More specifically, hairs were used for the washing experiments and were air-dried overnight before being evaluated by a panel of 12 judges. The fragrance intensity was rated from a scale ranging from 0 to 10. A numerical value of 2 suggests the hair only produce weak intensity while a value of 10 indicates the subject generate a very strong smell. The results are in FIG. 3.

Unexpectedly, this polyurea capsule composition provides much greater fragrance intensity than neat fragrance in hair conditioner base at both the pre-brush and post-brush stages.

EXAMPLE 26

Physical Characterizations of Polyurea Capsules

Figure 4:
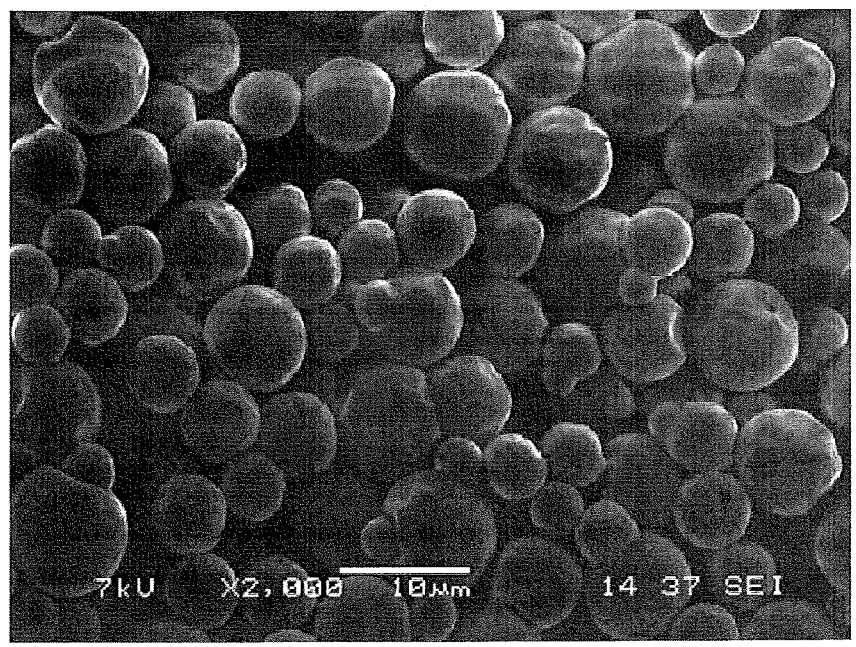
FIG. 4 shows a scanning electron microscopic image of capsules prepared in Example 20.

Scanning Electron Microscopy. A scanning electron microscopic picture was taken for the capsules prepared in Example 20. See FIG. 4. Unexpectedly, the capsules showed robust mechanical stability.

Zeta Potential. The zeta-potential of the capsules prepared in above examples was measured. More specifically, it was evaluated in a 0.14 wt % capsule solution in water following an experimental protocol provided by Zetasizer Nano-ZS (Malvern, Inc.). The results are shown in Table 4 below. Unexpectedly, the capsules prepared in Example 20 have a positive Zeta potential as high as 51 mV.

TABLE 4

| Precursor | Crosslinker | Dispersant | Zeta potential (mV) |
|---|---|---|---|
| Takenate D-110N | Branched polyethylenimine | Flexan/CMC | 51.6 |
| Takenate D-110N | Guanidine Carbonate | PVA/CMC | −62.6 |
| Desmodur N100 | Guanidine Carbonate | PVA/CMC | −71.8 |
| Desmodur 3600 | Lysine | Flexan/CMC | −42.6 |
| Desmodur N100 | 1,3-Diaminoguanidine Monohydrochloride | PVA/CMC | −30.8 |

EXAMPLE 27

Preparation of Polyurea Capsule Slurry with Improved Stability

To improve stability, twenty-six grams of the capsule slurry as prepared in Example 20 was weighed out and 4 g of POLYQUATERNIUM-11 (PQ11, Vinyl pyrrolidone/dimethylaminoethyl methacrylate copolymer, cationic polymer, LUVIQUAT PQ11 AT 1, BASF, Ludwigshafen, Germany) was added. The mixture was stirred for approximately 30 minutes via an overhead IKA lab mixer until the surfactant was completely dissolved and homogeneous.

Alternatively, a 10% solution of POLYQUATERNIUM-11 was prepared by dissolving 20 grams of the LUVIQUAT PQ11 AT 1 in 20 grams of water. The stabilized capsule slurry was prepared by mixing 7.5 grams of the fragrance capsule slurry prepared as in Example 20 with 22.5 grams of the 5% solution of POLYQUATERNIUM-11 under consistent mixing for 30 minutes.

Unexpectedly, the stability of the capsule mixtures were improved.

EXAMPLE 28-33

Polyurea Capsule Formulations Containing Surfactants and Polymers as Adjuvants

To evaluate other adjuvants, polyurea capsule slurries prepared in Example 20 were combined with one or more adjuvants as listed in Table 5 to obtain six capsule formulations. More specifically, a 10% polyquaternium-6 solution was prepared by adding water to a 40% polyquaternium-6 solution, commercially available from Nalco Inc. The 10% polyquaternium-6 solution was then mixed with a polyurea capsule slurry. The resultant mixture was homogenized using an overhead misted at 500 rpm for 30 minutes before being placed in oven for storage tests.

TABLE 5

| Formulation | Abbreviation of capsule adjuvant | Components of Adjuvant |
|---|---|---|
| 28 | CA106 | Poly(diallyldimethyl ammonium chloride), cationic polymer |
| 29 | CA111 | Vinyl pyrrolidone/dimethylaminoethyl methacrylate copolymer, cationic polymer |
| 30 | CA201 | Branched polyethylenimine |
| 31 | CA202 | Polyvinylamine |
| 32 | CA301 | Polyvinylpyrrolidone, non-ionic polymer |
| 33 | CA401 | Poly(acrylic acid, sodium salt) |

EXAMPLE 34

Performance Investigation of Polyurea Capsule Slurries with and without Polymer Adjuvants in EU Liquid Detergent Base To evaluate the performance of the polyurea capsules, the capsule slurries prepared in Example 20-27 were blended into a model European liquid detergent solution that was supplied by Unilever Company. The fragrance load was 0.5% neat equivalent. A comparative formulation was prepared using melamine-formaldehyde (MF) capsules described in US2007/0138671 at 0.5%. Another comparative capsule formulation was prepared using polyurea capsules without adding a dispersant. Each formulation was aged for 4 weeks at 37° C. The perfumery benefit of the capsules was evaluated by conducting a laundry experiment using standard experimental protocols with European wash machine. Terry towels were used for the washing experiments and were air-dried overnight before being evaluated by a panel of 12 judges. The fragrance intensity is rated from a scale ranging from 0 to 10. A numerical value of 2 suggests the fabric only produce weak intensity while a value of 10 indicates the subject generate a very strong smell.

Unexpectedly, polyurea formulations using the compositions prepared in Examples 20-27 had a much greater fragrance intensity than polyurea formulation without a dispersant, both in the pre-rub and post-rub tests; and two polyurea formulations, i.e., one containing PVP/CMC and the other PVP/CA111, had a much greater fragrance intensity than the MF formulation, also both in the pre-rub and post-rub tests.

EXAMPLE 35

Performance of Polyurea Capsule Slurries with Polymer Adjuvants in EU Fabric Conditioner Base To evaluate the performance of the polyurea capsules, the capsule slurries prepared in Example 20-27 were blended into a model European fabric conditioner solution that was supplied by Unilever Company. The fragrance load was 0.5% neat equivalent. A comparative formulation was prepared using melamine-formaldehyde (MF) capsules described in US2007/0138671 at 0.5%. Another comparative capsule formulation was prepared using polyurea capsules without adding a dispersant. Each formulation was aged for 4 weeks at 37° C. The perfumery benefit of the capsules was evaluated by conducting a laundry experiment using a standard experimental protocol with an European wash machine. Terry towels were washed with one of the formulations and then air-dried overnight before being evaluated by panel of 12 judges. The fragrance intensity is rated from a scale ranging from 0 to 10. A numerical value of 2 would suggest the fabric only produce weak intensity while a value of 10 indicates the subject generate a very strong smell.

Unexpectedly, polyurea formulations using the compositions prepared in Examples 20-27 had a much greater fragrance intensity than polyurea formulation without a dispersant, both in the pre-rub and post-rub tests; and two polyurea formulations, i.e., one containing CA106 and the other CA301, had a much greater fragrance intensity than the MF formulation, also both in the pre-rub and post-rub tests

EXAMPLE 36

Performance of Polyurea Capsule Slurries with Polymer Adjuvants in Hair Conditioner Base To evaluate their performance, the capsule slurries prepared in Example 20-27 were blended into a model hair conditioner base. The fragrance load was 0.5% neat equivalent. A comparative formulation was prepared using melamine-formaldehyde (MF) capsules described in US2007/0138671 at 0.5%. Another comparative capsule formulation was prepared using polyurea capsules without adding a dispersant. The perfumery benefit of the capsules was evaluated by conducting a personal wash experiment using a standard experimental protocol. Hair swatches were washed with one of the formulations and then air-dried overnight before being evaluated by a panel of 12 judges. The fragrance intensity is rated from a scale ranging from 0 to 10. A numerical value of 2 would suggest the hair only produce weak intensity while a value of 10 indicates the subject generate a very strong smell.

Unexpectedly, polyurea formulations using the compositions prepared in Examples 20-27 had a much greater fragrance intensity than polyurea formulation without a dispersant, both in the brushed and un-brushed tests; and three polyurea formulations, i.e., one containing CA202, one CA111/CA202, and the last CA301, had a much greater fragrance intensity than the MF formulation, also both in the brushed and un-brushed tests.

EXAMPLE 37

Performance of Polyurea Capsule Slurries with Polymer Adjuvants in Shampoo Base

To evaluate their performance, the capsule slurries prepared in Example 20-27 were blended into a model shampoo base. The fragrance load was 0.5% neat equivalent. A comparative formulation was prepared using melamine-formaldehyde (MF) capsules described in US2007/0138671 at 0.5%. Another comparative capsule formulation was prepared using polyurea capsules without adding a dispersant. The perfumery benefit of the capsules was evaluated by conducting a personal wash experiment using a standard experimental protocol. Hair swatches were washed with one of the formulations and then air-dried overnight before being evaluated by a panel of 12 judges. The fragrance intensity is rated from a scale ranging from 0 to 10. A numerical value of 2 would suggest the hair only produce weak intensity while a value of 10 indicates the subject generate a very strong smell.

Unexpectedly, polyurea formulations using the compositions prepared in Examples 20-27 had a greater fragrance intensity than polyurea formulation without a dispersant, both in the brushed and un-brushed tests; and three polyurea formulations, i.e., one containing CA106, one CA106/CA202, and the last CA201, had a much greater fragrance intensity than the MF formulation, also both in the brushed and un-brushed tests.

EXAMPLE 38

Polyurea Capsule Composition

Preparation of Sample 1-A. Ninety-six grams of a fragrance, Apple (International Flavors and Fragrance, Union Beach, N.J.) was weighed out and combined with 24 g of NEOBEE oil (Stepan, Chicago, Ill.) and 9.6 g of isocyanate monomer, LUPRANATE M20 (BASF corporation, Wyandotte, Mich.) to form the oil phase. In a separate beaker, a 1% surfactant solution (160 g) was prepared by dissolving sufficient amount of MORWET D-425 (Akzo Nobel, Fort Worth, Tex.) in water. The oil phase was then emulsified into the aqueous phase to form the fragrance emulsion under shearing (ULTRA TURRAX, T25 Basic, IKA WERKE) at 6500 rpm for two minutes.

The fragrance emulsion was placed in a round bottom vessel and 10.8 g of 40% hexamethylene diamine (HMDA) (INVISTA, Wichita, Kans.) was added under constant mixing with an overhead mixer. Formation of capsule was immediately visible by optical microscopy. The mixer speed was reduced after the addition of HMDA was complete. The capsule slurry was cured at 55° C. for three hours.

Preparation of Sample 2-A. Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, LUPRANATE M20 (BASF corporation, Wyandotte, Mich.) to form the oil phase. In a separate beaker, a solution (160 g) containing 1% MORWET D-425 (Akzo Nobel, Fort Worth, Tex.) was used as the aqueous phase. The oil phase was then emulsified into the aqueous phase to form the fragrance emulsion under shearing (ULTRA TURRAX, T25 Basic, and IKA WERKE) at 6500 rpm for two minutes.

The fragrance emulsion was placed in a round bottom vessel and 10.8 g of 40% HMDA (INVISTA, Wichita, Kans.) was added under constant mixing with an overhead mixer. Formation of capsule was immediately visible by optical microscopy. The mixer speed was reduced after the addition of HMDA was complete. The capsule slurry was cured at 55° C. for three hours.

After capsule preparation, the capsule slurry was washed with Water using a separatory funnel. Specifically, 300 mL Water was mixed with 300 g capsule slurry in a 1000 mL separatory funnel. The funnel was then sealed and shaken gently and was allowed to sit overnight so the capsule slurry separated from Water. The water layer was then removed. This process was repeated several times until the pH of the slurry was 7.0. Analytical measurement indicated the concentration of HMDA is less than 0.05%.

While 9.6 g of LUPRANATE M20 was used in this example, the amount of LUPRANATE M20 can be varied from 9.6 g to 28.8 g, with the addition of corresponding amount of 40% HMDA solution (10.8 g to 32.4 g). Likewise, the amount of MORWET D-425 can be varied from 0.5 to 4% depending on formulation need. Moreover, other dispersants include PVA (polyvinyl alcohol), CMC (carboxymethyl cellulose), PSSS (polystyrene sulfonic acid, sodium salt) can be employed.

Preparation of Sample 3-A. Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, LUPRANATE M20 (BASF corporation, Wyandotte, Mich.) to form the oil phase. In a separate beaker, a solution (160 g) containing 1% MORWET D-425 (Akzo Nobel, Fort Worth, Tex.) was used as the aqueous phase. The oil phase was then emulsified into the aqueous phase to form the fragrance emulsion under shearing (ULTRA TURRAX, T25 Basic, and IKA WERKE) at 6500 rpm for two minutes.

The fragrance emulsion was placed in a round bottom vessel and 10.8 g of 40% HMDA (INVISTA, Wichita, Kans.) was added under constant mixing with an overhead mixer. Formation of capsule was immediately visible by optical microscopy. The mixer speed was reduced after the addition of HMDA was complete. The capsule slurry was cured at 55° C. for three hours.

After preparation, the capsule slurry was washed with 1M NaCl aqueous solution using a separatory funnel. Specifically, 300 mL 1M NaCl aqueous solution was mixed with 300 g capsule slurry in a 1000 mL separatory funnel. The funnel was then sealed and shaken gently and was allowed sit overnight so that the capsule slurry could separate from the aqueous solution. The aqueous layer was then removed. This process was repeated several times until the pH of the slurry was 7.0. The capsule slurry was further washed with water several times using a separatory funnel.

EXAMPLE 39

Sensory Performance of Polyurea Capsules

To establish the consumer benefit of the polyurea capsules, Sample 1-A as prepared in Example 38 was incorporated into an aerosol formulation. The composition of the aerosol is provided in Table 6.

TABLE 6

| Raw Material | Description | % |
| --- | --- | --- |
| A46 | Propellant(Butane/Isobutane Mix) | 53.8 |
| Alcohol | Diluent | 44 |
| Fragrance | Perfume | 1.4 |
| Propylene Glycol | Solubilizer | 0.6 |
| COSMOCIL CQ | Deodorant Active | 0.2 |

A technician applied (sprayed) 1 g of each aerosol formulation onto a fragrance wearer's upper forearm. Eight arms were tested per sample using 15 trained judges. The judges rated the intensity of the product on skin at 5 hours after application under two conditions, prior to activation (pre-rub) and again in post-rubbed condition. For the post-rub evaluation, each wearer gently rubbed the upper forearm up and down to a count of six with two fingers. Judges smelled the top part of the forearm when evaluating the sample. Two-way analysis of variance was conducted with sample and panelists as independent variables and intensity as dependant variable, and again with condition (pre and post) and panelists as independent variables and intensity as dependant variable. Post hock analysis was by Duncan Multiple Comparison with significance set at 95% CI.

Figure 5:
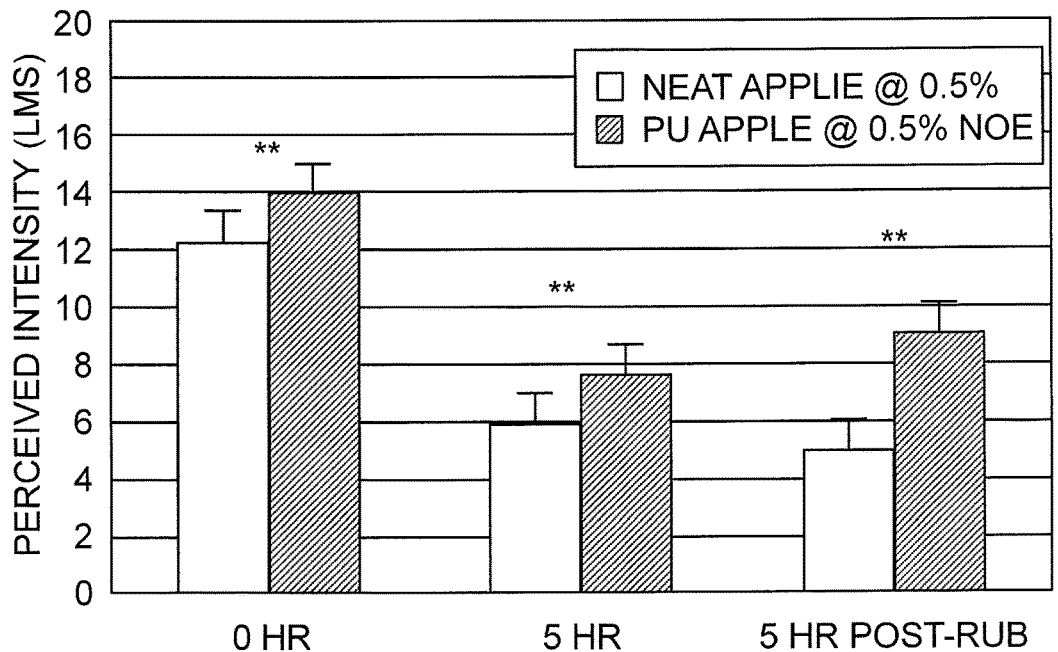
FIG. 5 shows the sensory performance of polyurea (PU) capsules as compared to neat fragrance in a hydroalcoholic aerosole formulation. The perceived intensity is shown using the labeled magnitude scale (LMS). N=14.

The sensory results are given in FIG. 5. This analysis indicated that the polyurea capsules provided significantly greater fragrance intensity at all-time points compared to neat fragrance. Moreover, the polyurea capsules had a significant increase in fragrance intensity from pre to post evaluation.

EXAMPLE 40

Sensory Performance of Purified Polyurea Capsules

Figure 6:
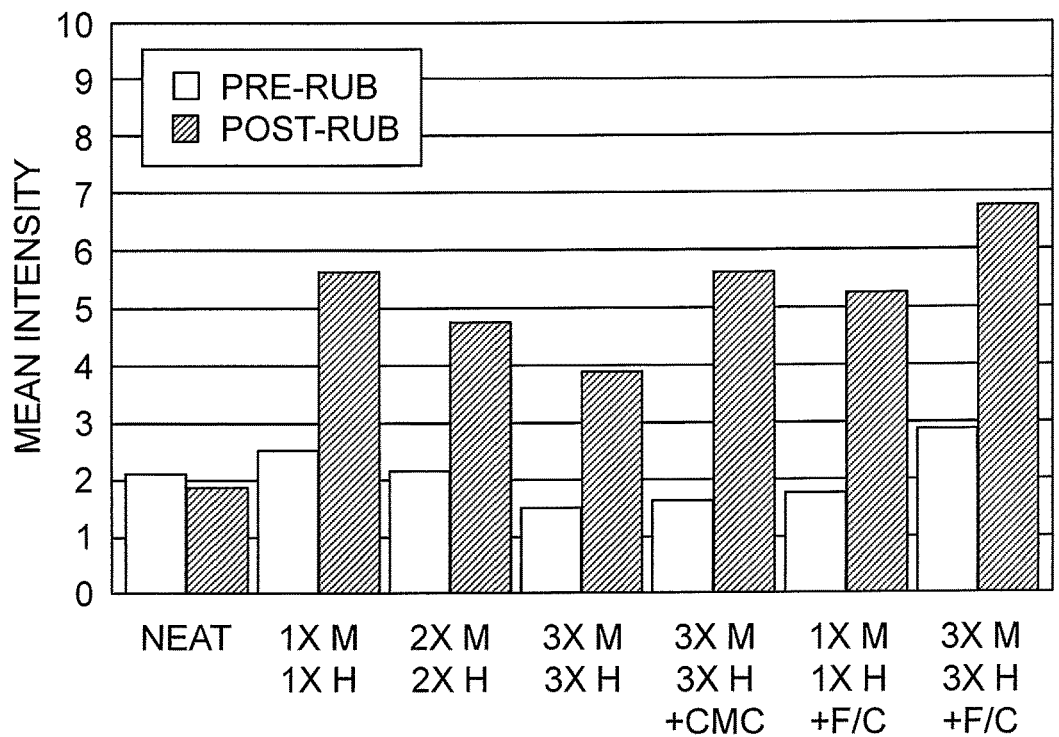
FIG. 6 shows sensory performance of polyurea capsules in hydroalcoholic medium (80:20 EtOH:$H_2O$) as compared to neat fragrance. Capsules were composed of 9.6 g (1× M), 19.2 g (2× M) or 28.8 g (3× M) LUPRANATE M20; or 10.8 g (1× H), 21.6 g (2× H) or 32.4 g (3× H), with (+) or without (−) CMC or FLEXAN/CMC (F/C). All samples were purified and had a pH of 7.

To establish the consumer benefit of the purified polyurea capsules, polyurea capsules prepared in accordance with Sample 2-A in Example 38 was mixed into a hydroalcoholic solution that contained 80% ethanol and 20% water. The concentration of the capsules was 4.5%. The polyurea capsule solution (0.3 g) was then sprayed onto a blotter (4×6) and allowed to dry overnight before being evaluated by a panel of 12 judges. The fragrance intensity was rated on a scale ranging from 0 to 10. A numerical value of 10 would suggest the subject generated a strong smell. The results are shown in FIG. 6.

Figure 7:
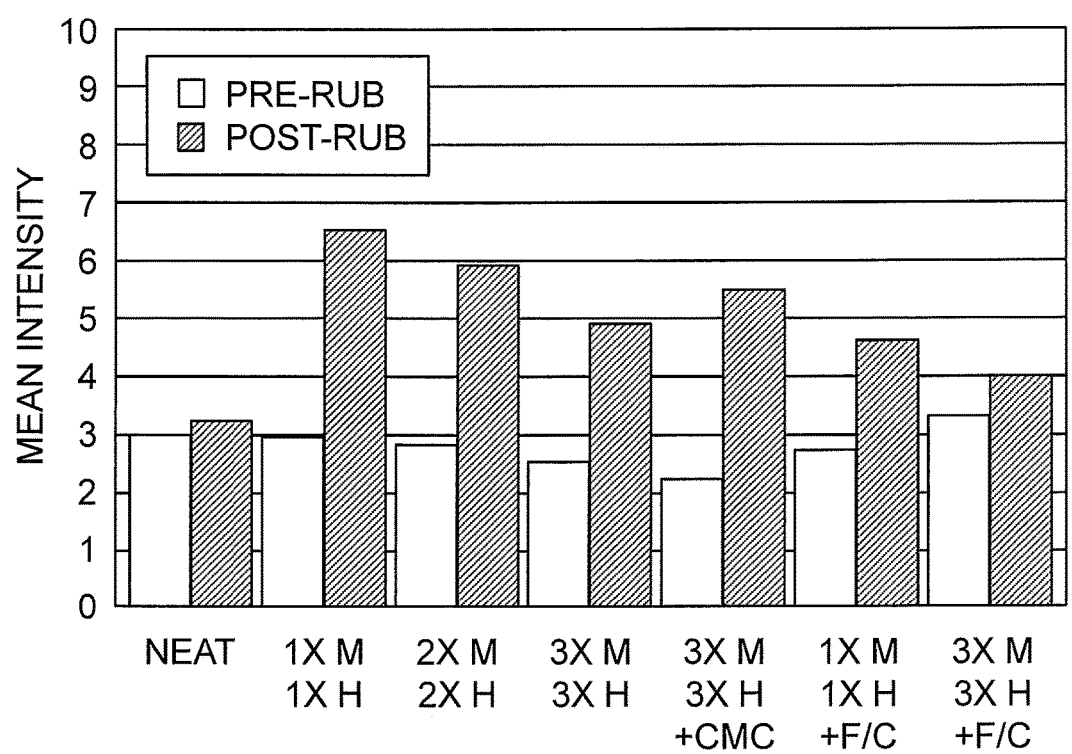
FIG. 7 shows sensory performance of polyurea capsules of FIG. 6 in hydroalcoholic medium after being aged at 25° C. for 4 weeks.

The results of this analysis indicated that capsules prepared in accordance with the present invention had a much stronger fragrance intensity compared to neat fragrance in the post-rubbing stage and were able to deliver the full benefit of the fragrance formulation. Moreover, the sensory performance of the polyurea capsules was retained after the samples were aged at 25° C. for 4 weeks (FIG. 7), demonstrating the unexpected robust storage stability and performance of the capsules.

EXAMPLES 41 AND 42

Washed Capsule Compositions

Two capsule compositions, i.e., Samples 12-A and 16-A, were prepare following a similar procedure as Sample 3-A in Example 38.

More specifically, Sample 12-A was prepared following a similar procedure as Sample 3-A except that the following different variables were applied: (i) fragrance Violet (International Flavors and Fragrance, Union Beach, N.J.), instead of Greenfields, (ii) 6000 rpm shearing, instead of 6500 rpm shearing, and (iii) that the amount of the fragrance being 0.3 fold that of Sample 3-A. Sample 16-A was prepared following a similar procedure as Sample 3-A except the following different variables were applied: (i) the amount of the polyurea or polyurethane wall material being 0.2 folds that of Sample 3-A, and (ii) the amount of Morwet D-425 being 0.5 folds that of Sample 3-A.

Two comparative samples, 12-A' and 16-A', were also prepared following the same procedures as 12-A and 16-A, respectively, except that the comparative samples were not washed with water, i.e., un-purified.

The contents of cross-linking agent HMDA were analyzed. Each of 12-A and 16-A showed a level of HMDA lower than 0.06%.

Further, 12-A and 16-A showed a greater fragrance intensity than their un-purified counterparts, i.e., 12-A' and 16-A'.

EXAMPLE 43

Polyurea Capsules Prepared with Aliphatic/Aromatic Polyisocyanate and Guanidine Amines/Salts Sample 1-B: Polyurea Capsule. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (130 g) containing 1.0% of MOWIOL 3-83 (Kuraray America Inc., Houston, Tex.) was mixed with deionized (DI) water (30 g) to form the aqueous phase. The oil phase was then emulsified into the aqueous phase under shearing (ULTRA TURRAX, T25 Basic, and IKA WERKE) at 6500 rpm for two minutes to form the fragrance emulsion.

The fragrance emulsion was placed in a round bottom vessel and 10.4 g of 36% guanidine carbonate (Sigma-Aldrich, St. Louis, Mo.) was added slowly under constant mixing with an overhead mixer. Formation of capsule was immediately visible by optical microscopy. The mixer speed was reduced after the addition of guanidine carbonate was complete. The capsule slurry was cured at 75° C. for three hours.

Sample 2-B: Polyurea Capsules with a Mixture of Nonionic and Anionic Dispersants. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (130 g) containing 1.0% of MOWIOL 3-83 (Kuraray America Inc., Houston, Tex.) was mixed with a solution (30 g) of 1% CMC in Water to form the aqueous phase. The oil phase was then emulsified into the aqueous phase under shearing (ULTRA TURRAX, T25 Basic, IKA WERKE) at 6500 rpm for two minutes to form the fragrance emulsion.

The fragrance emulsion was placed in a round bottom vessel and 10.4 g of 36% guanidine carbonate (Sigma-Aldrich, St. Louis, Mo.) was added slowly under constant mixing with an overhead mixer. Formation of capsule was immediately visible by optical microscopy. The mixer speed was reduced after the addition of guanidine carbonate was complete. The capsule slurry was cured at 75° C. for three hours.

Sample 3-B: Polyurea Capsules with a Mixture of Nonionic and Anionic Dispersants and a Catalyst. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (130 g) containing 1.0% of MOWIOL 3-83 (Kuraray America Inc., Houston, Tex.) was mixed with a solution (30 g) of 1% CMC in Water to form the aqueous phase. The oil phase was then emulsified into the aqueous phase under shearing (ULTRA TURRAX, T25 Basic, and IKA WERKE) at 6500 rpm for two minutes to form the fragrance emulsion.

The fragrance emulsion was heated to 35° C. before drop-wise addition of guanidine carbonate (10.1 g, 36%) and 0.30 g of DABCO (1,4-diazabicyclo[2.2.2]octane). Capsules formed immediately after the addition of guanidine carbonate. The capsule slurry was transferred into a round bottom vessel and cured at 75° C. for three hours.

Sample 4-B: Polyurea Capsules Prepared with DESMODUR 3600, a Mixture of Nonionic and Anionic Dispersants and a Catalyst. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR 3600 (Bayer Corp., Pittsburgh, Pa.) to form the oil phase. In a separate beaker, a solution (130 g) containing 1.0% of MOWIOL 3-83 (Kuraray America Inc., Houston, Tex.) was mixed with a solution (30 g) of 1% CMC in Water to form the aqueous phase. The oil phase was then emulsified into the aqueous phase under shearing (ULTRA TURRAX, T25 Basic, and IKA WERKE) at 6500 rpm for two minutes to form the fragrance emulsion.

The fragrance emulsion was heated to 35° C. before drop-wise addition of guanidine carbonate (10.1 g, 36%) and 0.30 g of DABCO. Capsules formed immediately after the addition of guanidine carbonate. The capsule slurry was transferred into a round bottom vessel and cured at 75° C. for three hours.

Sample 5-B: Polyurea Capsules Prepared with LUPRANATE M20, a Mixture of Nonionic and Anionic Dispersants, and a Catalyst. Ninety-six grams of a fragrance, Greenfields (IFF, Union Beach, N.J.) was weighed out and combined with 24 g of NEOBEE oil (Stepan, Chicago, Ill., USA) and 9.6 g of isocyanate monomer, LUPRANATE M20 (BASF Corp., Wyandotte, Mich.) to form the oil phase. In a separate beaker, a solution (130 g) containing 1.0% of MOWIOL 3-83 (Kuraray America Inc., Houston, Tex.) was mixed with a solution (30 g) of 1% CMC in Water to form the aqueous phase. The oil phase was then emulsified into the aqueous phase under shearing (ULTRA TURRAX, T25 Basic, and IKA WERKE) at 6500 rpm for two minutes to form the fragrance emulsion.

The fragrance emulsion was heated to 35° C. before drop-wise addition of guanidine carbonate (10.1 g, 36%) and 0.30 g of DABCO. Capsules formed immediately after the addition of guanidine carbonate. The capsule slurry was transferred into a round bottom vessel and cured at 75° C. for three hours.

Sample 6-B: Polyurea Capsules Containing a Blend of Nonionic and Cationic Dispersants. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (130 g) containing 0.6% of MOWIOL 18-88 (Kuraray America Inc., Houston, Tex.) was mixed with a solution (7.5 g) of 1% LUVIQUAT Ultra Care (polyquaternium-44, BASF, Tarrytown, N.Y.) in Water to form the aqueous phase. The oil phase was then emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of guanidine carbonate (10.1 g, 36%) and 0.30 g of DABCO. Capsules formed immediately after the addition of guanidine carbonate. The capsule slurry was transferred into a round bottom vessel and cured at 75° C. for three hours.

Sample 7-B: Polyurea Capsules Containing Guanidine Hydrochloride. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (130 g) containing 1.0% of PVA (polyvinyl alcohol, MOWIOL 3-83, (Kurray, Houston, Tex.) was mixed with a solution (30 g) of 1% CMC in Water to form the aqueous phase. The oil phase was then emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of guanidine hydrochloride (10.1 g, 36%) and 0.30 g of DABCO. Capsules formed immediately after the addition of guanidine hydrochloride. The capsule slurry was transferred into a round bottom vessel and cured at 75° C. for three hours.

Sample 8-B: Polyurea Capsules Containing Guanidine Hydrochloride Prepared Under Basic Conditions. Ninety-six grams of a fragrance, Greenfields (International IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (130 g) containing 1.0% PVA (polyvinyl alcohol, MOWIOL 3-83, (Kurray, Houston, Tex.) was mixed with a solution (30 g) of 1% CMC in Water to form the aqueous phase. The oil phase was then emulsified into the aqueous phase under shearing (ULTRA TURRAX, T25 Basic, IKA WERKE) at 6500 rpm for two minutes to form the fragrance emulsion.

A mixture of guanidine hydrochloride (10.1 g, 36%) and catalyst (0.30 g), DABCO (Dow Chemical, Midland, Mich.) was adjusted to pH 12 using 12 mol/L sodium hydroxide. The fragrance emulsion was heated to 35° C. before drop-wise addition of the aqueous mixture. Capsules formed immediately after the addition of guanidine hydrochloride. The capsule slurry was transferred into a round bottom vessel and cured at 75° C. for three hours.

Sample 9-B: Polyurea Capsules Containing Guanidine Hydrochloride and Sodium Carbonate Prepared Under Basic Conditions. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (130 g) containing 1.0% PVA (polyvinyl alcohol, MOWIOL 3-83, (Kurray, Houston, Tex.) was mixed with a solution (30 g) of 1% CMC in Water to form the aqueous phase. The oil phase was then emulsified into the aqueous phase under shearing (ULTRA TURRAX, T25 Basic, IKA WERKE) at 6500 rpm for two minutes to form the fragrance emulsion.

A mixture containing guanidine hydrochloride (10.1 g, 36%), sodium carbonate (3 g), and catalyst (0.30 g), DABCO (Dow Chemical, Midland, Mich.) was adjusted to pH 12 by 12 mol/L sodium hydroxide. The fragrance emulsion was heated to 35° C. before drop-wise addition of the aqueous mixture. Capsules formed immediately after the addition of guanidine hydrochloride. The capsule slurry was transferred into a round bottom vessel and cured at 75° C. for two hours.

Figure 8A:
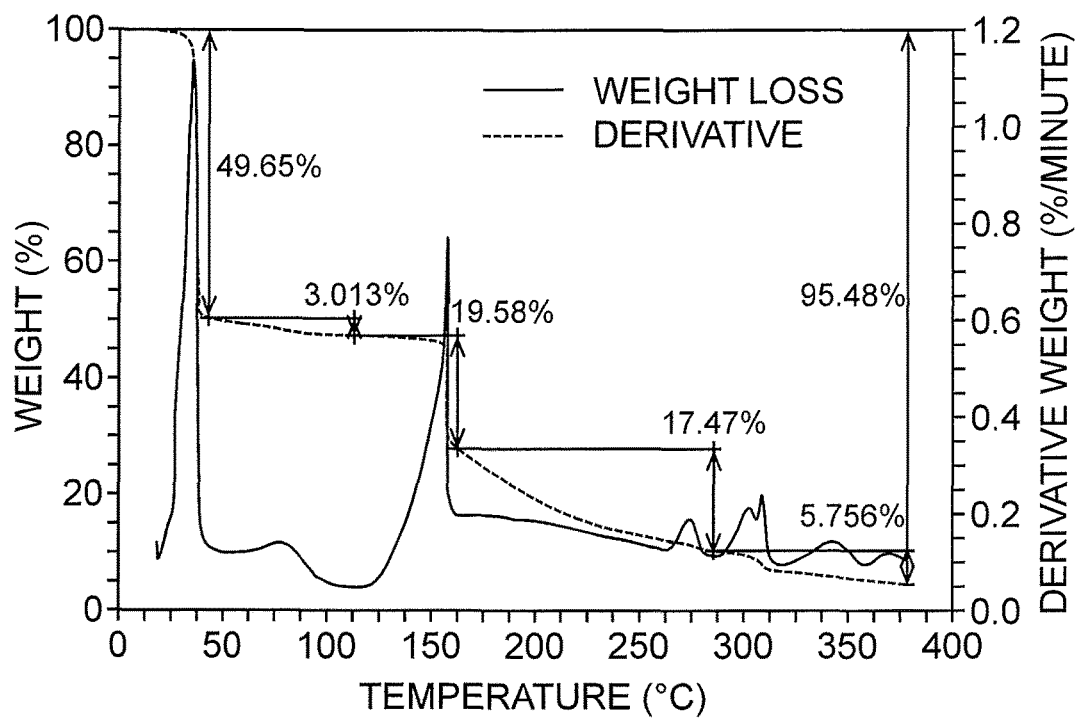
FIGS. 8A-8D show thermogravimetric analyses of samples prepared with polyvinyl alcohol (PVA) and carboxymethyl cellulose (CMC) (FIGS. 8A and 8D); PVA and Polyquaternium-44 (FIG. 8B); or PVA alone (FIG. 8C). These results demonstrate the thermal stability of the samples prepared with a capsule formation aid. Polyurea capsules of FIGS. 8A-8C were prepared with the aliphatic polyisocyanate DESMODUR N100 and guanidine carbonate, whereas the polyurea capsules of FIG. 8D were prepared with the aliphatic polyisocyanate DESMODUR 3600 and guanidine carbonate.
Figure 8B:
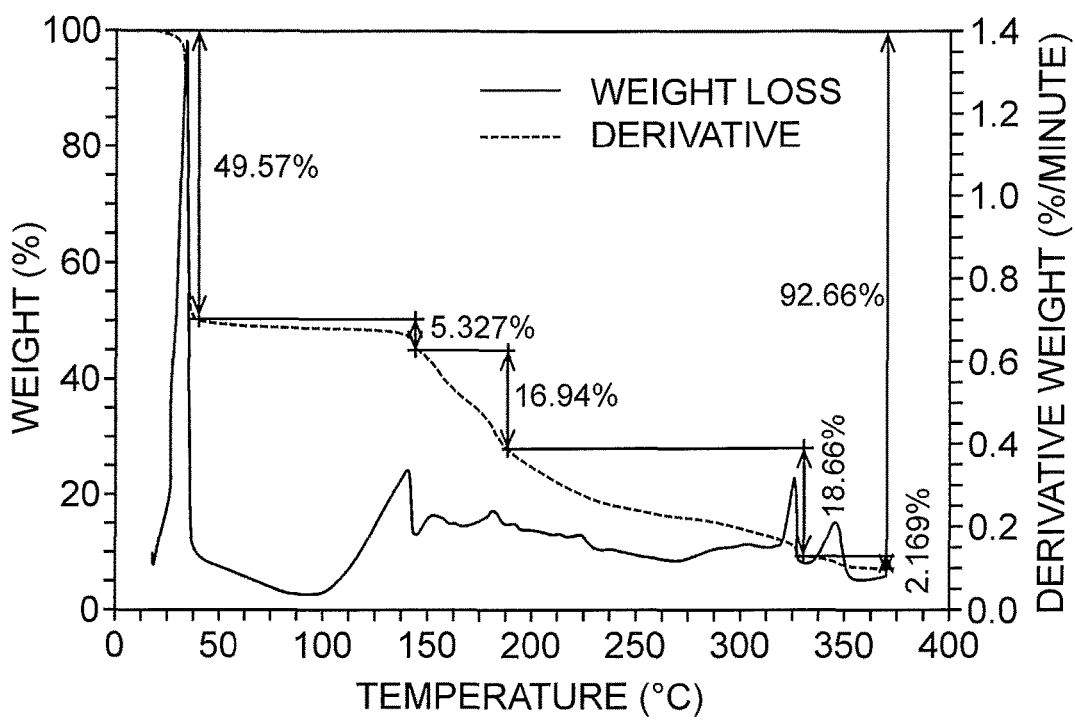
Figure 8C:
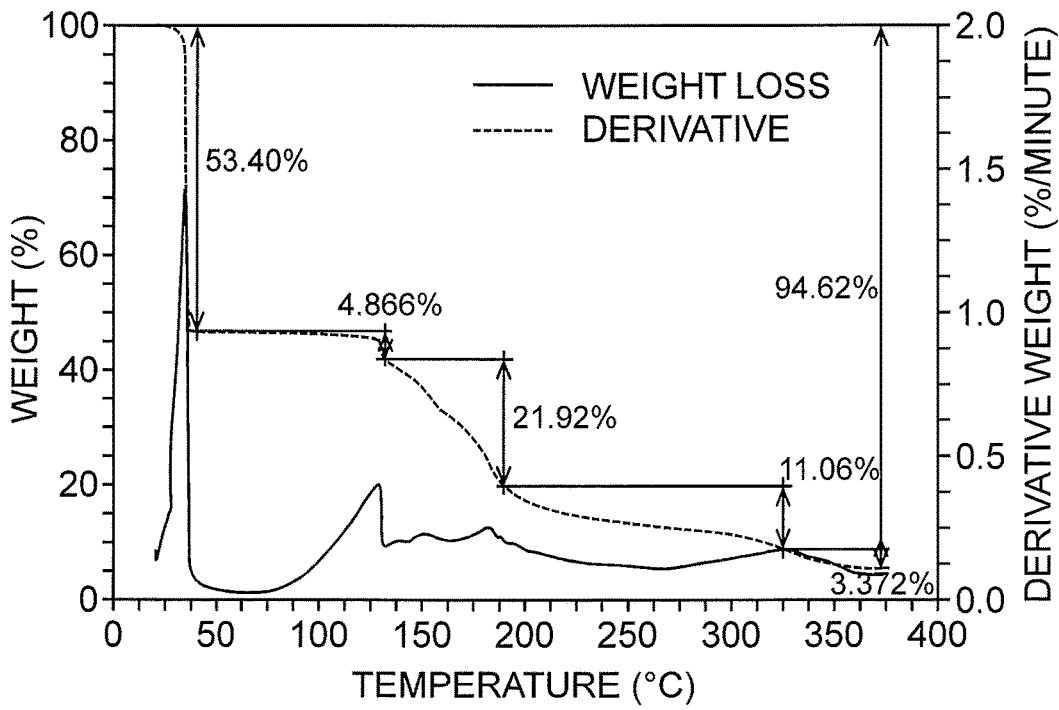
Figure 8D:
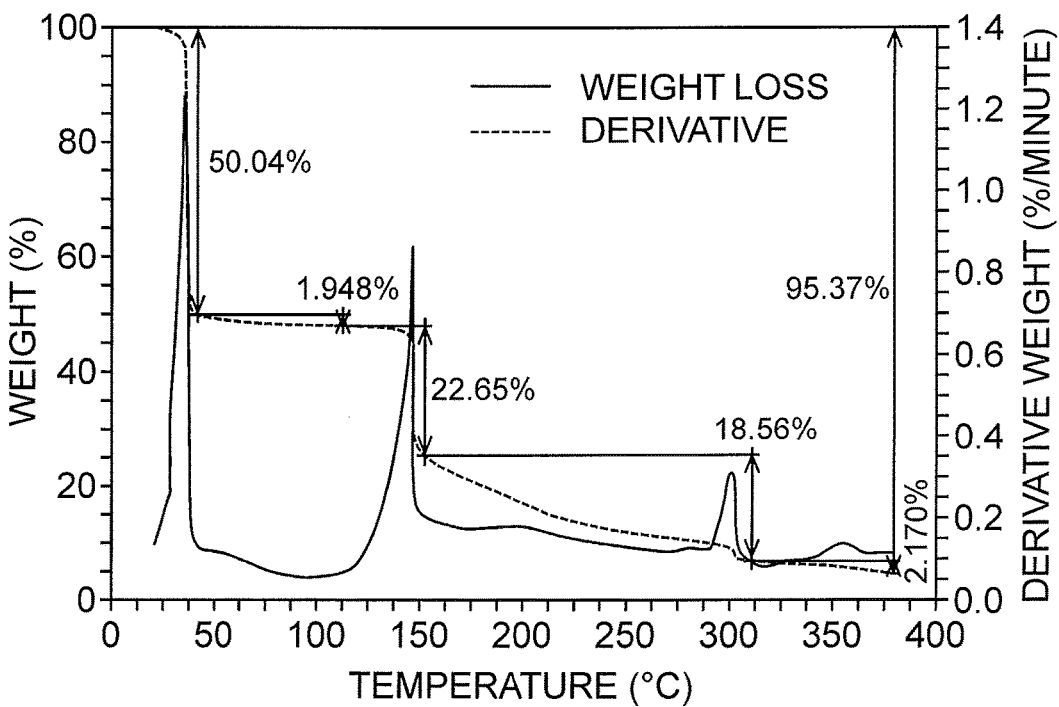

Physical Characterization of Polyurea Capsule. Microscopic analysis indicated that the capsules prepared in accordance with this invention had robust mechanical stability. Furthermore, thermogravimetric analyses (FIGS. 8A-8D) indicated that samples prepared with a mixture of PVA and CMC as capsule formation aid (FIGS. 8A and 8D) released their contents at a higher temperature than capsules made from a mixture of PVA and POLYQUATERNIUM-44 (FIG. 1B) or PVA alone (FIG. 8C). These results demonstrate the thermal stability of the samples prepared with a capsule formation aid.

Encapsulation Performance of Polyurea Capsules. Sample 2-B was diluted with distilled water to yield a mixture containing 0.2% capsule slurry. One gram each of the diluted capsule slurry was directly applied to each side of a 4×6 fabric swatch. Two samples were prepared. The swatches were air-dried overnight and the headspace of the fabrics was analyzed before and after stirring with stainless steel ball bearings to rupture intact capsules. The results of this analysis are presented in Table 7.

TABLE 7

|  | Unstirred | Stirred |
| --- | --- | --- |
| Headspace | 3746 | 16556 |
| Ratio Stirred/Unstirred | — | 4.11 |

This analysis indicated that there was a dramatic increase in headspace after the capsules were disrupted by milling. This demonstrated that increased perfumery perception can be achieved once the capsules are deposited on fabric and ruptured by physical forces.

Sensory Performance of Polyurea Capsules. To establish the consumer benefits of the polyurea capsules, a capsule slurry was blended into a roll-on base and evaluated for its consumer benefits. The fragrance load was 0.50% neat equivalent. For comparison, a similar solution was prepared using neat fragrance at 0.5%. The sample (0.3 g) was then applied to a blotter (4×6) and was allowed to dry overnight before being evaluated by a panel of 12 judges. The fragrance intensity was rated on a scale ranging from 0 to 10. A numerical value of 10 would suggest the subject generated a strong smell. The results of this analysis are presented in Table 8.

TABLE 8

| Samples | Pre-rubbing intensity | Post-rubbing intensity | $I_{post,\ capsule}/I_{post,\ neat}$ |
| --- | --- | --- | --- |
| Neat | 1.7 | 2.7 |  |
| Capsule Slurry | 1 | 6.1 | 2.25 |

This analysis indicated that the capsules prepared in accordance with the present invention had a much stronger fragrance intensity compared with neat fragrance in the post-rubbing stage and was able to deliver the full benefit of the fragrance formulation.

Perfumery Performance of Polyurea Capsules. To establish the performance of the polyurea capsules, Samples 3-B and 4-B were blended into a model rinse conditioner solution that contained 24% cationic surfactant. The fragrance load was 0.5% neat equivalent. For comparison, a similar solution was prepared using neat fragrance at 1%. The perfumery benefit of the capsules was evaluated by conducting a laundry experiment using conventional experimental protocols. Terry towels were used for the washing experiments and were air-dried overnight before being evaluated by a panel of 12 judges. The fragrance intensity was rated on a scale ranging from 0 to 10. A numerical value of 2 would suggest the fabric only produced very week intensity while a value of 10 indicated the subject generated a strong smell. The results of this analysis are presented in Table 9.

TABLE 9

| Samples | Pre-rubbing intensity | Post-rubbing intensity | $I_{pre, capsule}/I_{pre, neat}$ | $I_{post, capsule}/I_{post, neat}$ |
|---|---|---|---|---|
| Neat | 0.5 | 1.5 | | |
| Sample 3-B | 1 | 6 | 2 | 4 |
| Sample 4-B | 1 | 6.5 | 2 | 4.3 |

This analysis indicated that the polyurea fragrance capsules produced much greater fragrance intensity at the pre-rubbing and post-rubbing stages. The increase in fragrance intensity was much more pronounced in the post-rubbing stage. This demonstrates that the polyurea fragrance capsules prepared in accordance with the current invention are able to retain the fragrance effectively and are capable of delivering the full consumer benefits of the fragrance products.

Application Benefit of Polyurea Capsules. Application benefit in a personal care product was further evaluated using a hair conditioner formulation. To conduct the experiment, the capsule slurry was dispersed in a hair conditioner base at 0.5% neat fragrance equivalent. The hair conditioner base was a Magick Botanicals oil-free conditioner base. To the base was added Sample 3-B. The formulation was applied to bundles of hair (40 g each), which contained four hair strands. The bundles were subsequently washed by wetting two bundles (8 strands) under water (water temperature: 100 F/38 C; flow rate: 1 gallon/minute) and lightly squeezing off the excess water. The hair was placed onto a balance and 2 g of unfragranced shampoo was directly applied onto the wet hair. The hair was lathered between palms, 10× clockwise and 10× counterclockwise, keeping the wax part of the swatches between two fingers (not to spread wax over surface of hair). The hair swatches were allowed to stand for 15 seconds and subsequently rinsed under a stream of water for 45 seconds. The process was repeated with hair conditioner. Excess water was gently squeezed out and the hair was allowed to dry overnight. The dried samples were then evaluated by 16 trained panelists and the results are presented in Table 10.

TABLE 10

| Samples | Pre-rubbing intensity | Post-rubbing intensity | $I_{pre, capsule}/I_{pre, neat}$ | $I_{post, capsule}/I_{post, neat}$ |
|---|---|---|---|---|
| Neat | 1.0 | 0.8 | | |
| Sample 3-B | 0.5 | 4.0 | 0.5 | 5.0 |

This analysis demonstrated that the product containing polyurea capsules had much stronger perfumery intensity than the neat fragrance. Thus, the polyurea capsule delivered excellent consumer benefits both in the pre- and post-rubbing stage.

EXAMPLE 44

Polyurea Capsule Prepared with Polyaliphatic Isocyanate and Amphoteric Amines

Sample 1-C: Preparation of Polyurea Capsule. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a 1.0% surfactant solution (160 g) was prepared by dissolving a sufficient amount of MORWET D-425 (Akzo Nobel, Fort Worth, Tex.) in Water. The oil phase was then emulsified into the aqueous phase under shearing (ULTRA TURRAX, T25 Basic, and IKA WERKE) at 6500 rpm for two minutes to form the fragrance emulsion.

The fragrance emulsion was placed in a round bottom vessel and 10.4 g of 56% lysine (Sigma-Aldrich, St. Louis, Mo.) was added under constant mixing with an overhead mixer. Formation of capsule was immediately visible by optical microscopy. The mixer speed was reduced after the addition of lysine was complete. The capsule slurry was cured at 55° C. temperature for three hours.

Sample 2-C: Polyurea Capsules Prepared with a Catalyst. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (130 g) containing 1.0% of FLEXAN II (Akzo Nobel, Bridgewater, N.J.) was mixed with a solution (30 g) of 1% CMC in Water to form the aqueous phase. The oil phase was then emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of a mixture containing lysine (10.1 g, 58%) and DABCO (0.30 g, Dow Chemical, Midland, Mich.). Capsules were formed was immediately after the addition of lysine and catalyst. The capsule slurry was transferred into a round bottom vessel and the capsules were cured at 55° C. for 2 hours.

Sample 3-C: Polyurea Capsule Prepared with More Amino Acid. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a 1.0% surfactant solution (160 g) was prepared by dissolving sufficient amount of MORWET D-425 (Akzo Nobel, Fort Worth, Tex.) in Water. The oil phase was then emulsified into the aqueous phase under shearing (ULTRA TUR- RAX, T25 Basic, IKA WERKE) at 6500 rpm for two minutes to form the fragrance emulsion.

The fragrance emulsion was placed in a round bottom vessel and 19.8 g of 57% lysine (Sigma-Aldrich, St. Louis, Mo.) and 0.60 g DABCO were added under constant mixing with an overhead mixer. Formation of capsule was immediately visible by optical microscopy. The mixer speed was reduced after the addition of lysine was complete. The capsule slurry was cured at 55° C. temperature for three hours.

Sample 4-C: Polyurea Capsule Prepared with the Addition of Amino Acid at Elevated Temperature. Ninety six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a 1.0% surfactant solution (160 g) was prepared by dissolving sufficient amount of MORWET D-425 (Akzo Nobel, Fort Worth, Tex., USA) in Water. The oil phase was then emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of lysine (10.1 g, 58%) and 0.30 g of DABCO. Formation of capsule was immediately visible by optical microscopy. The capsule slurry was transferred into a round bottom vessel and cured at 55° C. temperature for two hours.

Sample 5-C: Polyurea Capsule Prepared with the Addition of Amino Acid at Elevated Temperature and Curing at Elevated Temperature. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a 1.0% surfactant solution (160 g) was prepared by dissolving a sufficient amount of MORWET D-425 (Akzo Nobel, Fort Worth, Tex.) in Water. The oil phase was then emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of lysine (10.1 g, 58%) and 0.30 g of DABCO. Formation of capsule was immediately visible by optical microscopy. The capsule slurry was transferred into a round bottom vessel and the capsule slurry was cured at 55° C. for 2 hours and then at 80° C. for 2 hours.

Sample 6-C: Polyurea Capsules Prepared with a Blend of Dispersants. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (130 g) containing 1.0% of FLEXAN II (Akzo Nobel, Bridgewater, N.J.) was mixed with a solution (30 g) of 1% CMC in Water to form the aqueous phase. The oil phase was then emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of lysine (10.1 g, 58%) and 0.30 g of DABCO. Formation of capsule was immediately visible by optical microscopy. The capsule slurry was transferred into a round bottom vessel and cured at 55° C. for 2 hours.

Sample 7-C: Polyurea Capsules Prepared with Arginine. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (120 g) containing 1.1% of FLEXAN II (Akzo Nobel, Bridgewater, N.J.) was mixed with a solution (30 g) of 1% CMC in Water to form the aqueous phase. The oil phase was then emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of arginine (20.1 g, 25%) and 0.30 g DABCO. Fragrance capsule was immediately after the addition of lysine and catalyst. Formation of capsule was immediately visible by optical microscopy. The capsule slurry was transferred into a round bottom vessel and cured at 55° C. for 2 hours.

Sample 8-C: Polyurea Capsules Prepared with Arginine Monohydrochloride. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (120 g) containing 1.1% PVA (polyvinyl alcohol, MOWIOL 3-83; Kurray, Houston, Tex.) was combined with 30 g of Water to form the aqueous phase. The oil phase was then emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of arginine monohydrochloride (20.1 g, 32%) and 0.30 g DABCO. Formation of capsule was immediately visible by optical microscopy. The capsule slurry was transferred into a round bottom vessel and cured at 55° C. for 2 hours.

Sample 9-C: Polyurea Capsules Prepared with Lysine Under Basic Conditions. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (130 g) containing 1.0% PVA (polyvinyl alcohol, MOWIOL 3-83; Kurray, Houston, Tex.) was mixed with a solution (30 g) of 1% CMC in Water to form the aqueous phase. The oil phase was then emulsified into the aqueous phase under shearing (ULTRA TURRAX, T25 Basic, IKA WERKF) at 6500 rpm for two minutes to form the fragrance emulsion.

A mixture containing lysine (10.1 g, 58%) and DABCO (0.30 g) was adjusted to pH 12 by 12 mol/L sodium hydroxide. The fragrance emulsion was heated to 35° C. before the aqueous mixture was added drop-wise. Formation of capsule was immediately visible by optical microscopy. The capsule slurry was transferred into a round bottom vessel and cured at 55° C. for 2 hours.

Sample 10-C: Polyurea Capsules Prepared with Lysine and Sodium Carbonate Under Basic Conditions. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (130 g) containing 1.0% PVA (polyvinyl alcohol, MOWIOL 3-83; Kurray, Houston, Tex.) was mixed with a solution (30 g) of 1% CMC in Water to form the aqueous phase. The oil phase was then emulsified into the aqueous phase under shearing (ULTRA TURRAX, T25 Basic, IKA WERKE) at 6500 rpm for two minutes to form the fragrance emulsion.

A mixture containing lysine (10.1 g, 56%), sodium carbonate (4 g), and DABCO (0.30 g) was adjusted to pH 12 by 12 mol/L sodium hydroxide. The fragrance emulsion was heated to 35° C. before drop-wise addition of the aqueous mixture. Formation of capsule was immediately visible by optical microscopy. The capsule slurry was transferred into a round bottom vessel and cured at 55° C. for 2 hours.

Sample 11-C: Polyurea Capsules Prepared with Arginine Monohydrochloride Under Basic Condition. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (120 g) containing 1.1% PVA (polyvinyl alcohol, MOWIOL 3-83; Kurray, Houston, Tex.) was mixed with a solution (30 g) of 1% CMC in Water to form the aqueous phase. The oil phase was then emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of a mixture containing arginine monohydrochloride (18.9 g, 35%), sodium hydroxide (1.2 g), and DABCO (0.30 g). Formation of capsule was immediately visible by optical microscopy. The capsule slurry was transferred into a round bottom vessel and cured at 55° C. for 2 hours.

Sample 12-C: Polyurea Capsules Prepared with Arginine Monohydrochloride and Sodium Carbonate. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (120 g) containing 1.0% PVA (polyvinyl alcohol, MOWIOL 3-83; Kurray, Houston, Tex.) was mixed with a solution (30 g) of 1% CMC in Water to form the aqueous phase. The oil phase was then emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of a mixture containing arginine monohydrochloride (16.1 g, 41%), sodium carbonate (4 g), and DABCO (0.30 g). Formation of capsule was immediately visible by optical microscopy. The capsule slurry was transferred into a round bottom vessel and cured at 55° C. for 2 hours.

Figure 9A:
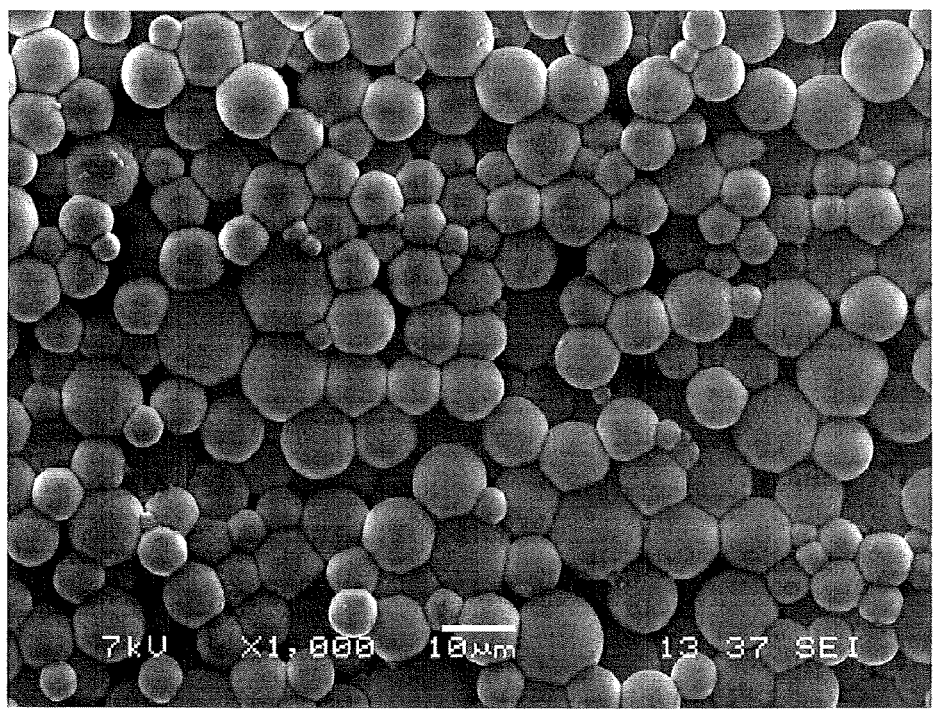
FIGS. 9A and 9B respectively show a scanning electron microscope (SEM) image and optical image of capsules from Sample 2-C in Example 44.
Figure 9B:
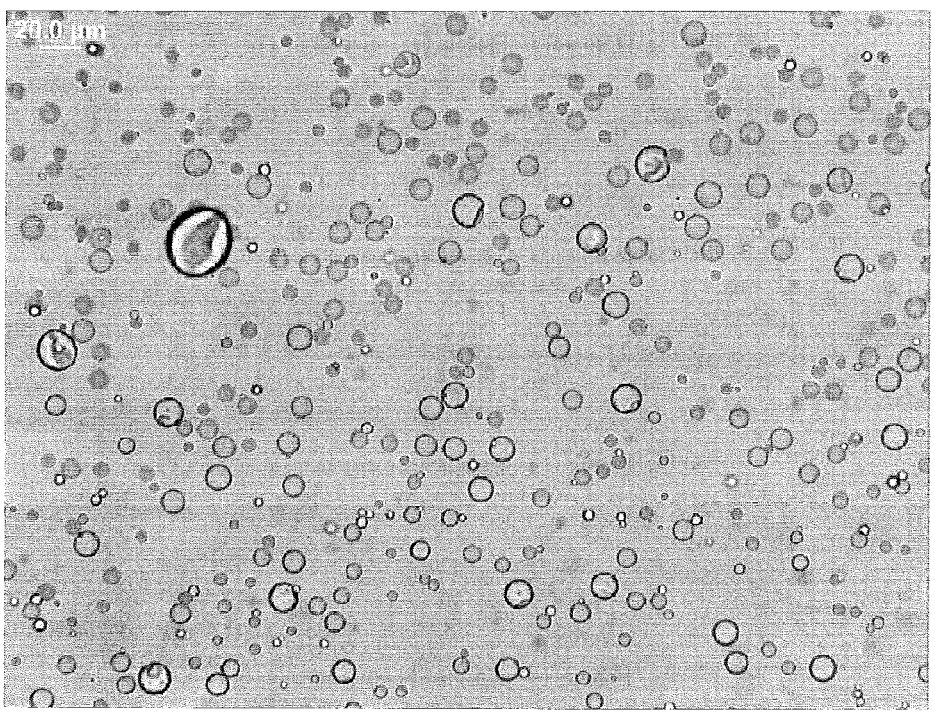

Physical Characterization of Polyurea Capsules. The capsules from Sample 2-C were analyzed with scanning electron microscopy (FIG. 9A) and optical microscopy (FIG. 9B). It was found that the capsules prepared in accordance with the present invention have robust mechanical stability.

Encapsulation Performance of Polyurea Capsules. The fragrance capsule slurry (Sample 2-C) was diluted with distilled water to yield a mixture containing 0.2% capsule slurry. One gram of the diluted capsule slurry was directly applied to each side of a 4×6 fabric swatch. Two experiments were prepared. The swatches were air-dried overnight and the headspace of the fabrics was analyzed before and after stirring with stainless steel ball bearings to rupture intact capsules. The results of this analysis are presented in Table 11.

TABLE 11

|  | Experiment 1 | | Experiment 2 | |
| --- | --- | --- | --- | --- |
|  | Unstirred | Stirred | Unstirred | Stirred |
| Headspace | 2500 | 35000 | 2600 | 55000 |
| Ratio Stirred/Unstirred | — | 14.0 | — | 21.1 |

This analysis indicated that there was a dramatic increase in headspace after the capsules were disrupted by milling. This demonstrated that increased perfumery perception can be achieved once the capsules are deposited on fabric and ruptured by physical forces.

Sensory Performance of Polyurea Capsules. To establish the consumer benefits of the polyurea capsules, a capsule slurry prepared with an aliphatic isocyanate and amphoteric amine was blended into a roll-on base and evaluated for its consumer benefits. The fragrance load was 0.5% neat equivalent. For comparison, a similar solution was prepared using neat fragrance at 0.5%. The sample (0.3 g) was then applied to a blotter (4×6) and was allowed to dry overnight before being evaluated by a panel of 12 judges. The fragrance intensity was rated on a scale ranging from 0 to 10. A numerical value of 10 would suggest the subject generated a strong smell. The results of this analysis are presented in Table 12.

TABLE 12

| Samples | Pre-rubbing intensity | Post-rubbing intensity | $I_{post,\ capsule}/I_{post,\ neat}$ |
| --- | --- | --- | --- |
| Neat | 1.5 | 2.5 | |
| Capsule Slurry | 1.0 | 7.4 | 2.96 |

Capsules prepared with current invention had a much stronger fragrance intensity compared with neat fragrance in the post-rubbing stage and were able to deliver the full benefit of the fragrance formulation.

EXAMPLE 45

Polyurea Capsules Prepared with Polyaliphatic Isocyanate and a Diamine

Sample 1-D: Preparation of Polyurea Capsule. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N3600 (Bayer corporation, Pittsburgh, Pa.) to form the oil phase. In a separate beaker, a 1.5% surfactant solution (160 g) was prepared by dissolving a sufficient amount of MORWET D-425 (Akzo Nobel, Fort Worth, Tex.) in Water. The oil phase was emulsified into the aqueous phase under shearing (ULTRA TURRAX, T25 Basic, IKA WERKE) at 6500 rpm for two minutes to form the fragrance emulsion.

The fragrance emulsion was placed in a round bottom vessel and 10.8 g of 70% hexamethylene diamine (HMDA) (INVISTA, Wichita, Kans.) was added under constant mixing with an overhead mixer. Formation of capsule was immediately visible by optical microscopy. The mixer speed was reduced after the addition of HMDA was complete. The capsule slurry was cured at 55° C. for three hours.

Sample 2-D: Preparation of Polyurea Capsule with More Amine. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N3600 (Bayer corporation, Pittsburgh, Pa.) to form the oil phase. In a separate beaker, a 1.5% surfactant solution (160 g) was prepared by dissolving a sufficient amount of MORWET D-425 (Akzo Nobel, Fort Worth, Tex.) in Water. The oil phase was emulsified into the aqueous phase under shearing (ULTRA TURRAX, T25 Basic, IKA WERKF) at 6500 rpm for two minutes to form the fragrance emulsion.

The fragrance emulsion was placed in a round bottom vessel and 21.6 g of 70% HMDA (INVISTA, Wichita, Kans.) was added under constant mixing with an overhead mixer. Formation of capsule was immediately visible by optical microscopy. The mixer speed was reduced after the addition of HMDA was complete. The capsule slurry was cured at 55° C. for three hours.

Sample 3-D: Polyurea Capsule with the Addition of HMDA at Elevated Temperature. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N3600 (Bayer corporation, Pittsburgh, Pa.) to form the oil phase. In a separate beaker, a 1.5% surfactant solution (160 g) was prepared by dissolving a sufficient amount of MORWET D-425 (Akzo Nobel, Fort Worth, Tex.) in Water. The oil phase was emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of HMDA (10.8 g, 70%). Formation of capsule was immediately visible by optical microscopy. The capsule slurry was cured at 55° C. for two hours.

Sample 4-D: Polyurea Capsule with Addition of HMDA at Elevated Temperature and Curing at Elevated Temperature. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N3600 (Bayer corporation, Pittsburgh, Pa.) to form the oil phase. In a separate beaker, a 1.5% surfactant solution (160 g) was prepared by dissolving a sufficient amount of MORWET D-425 (Akzo Nobel, Fort Worth, Tex.) in Water. The oil phase was emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of HMDA (10.8 g, 70%). Formation of capsule was immediately visible by optical microscopy. The capsule slurry was transferred into a round bottom vessel and the capsule slurry was cured at 55° C. for 2 hours and then at 80° C. for 2 hours.

Sample 5-D: Polyurea Capsules Prepared with a Blend of Dispersants. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N3600 (Bayer corporation, Pittsburgh, Pa.) to form the oil phase. In a separate beaker, a solution (130 g) containing 1.85% FLEXAN II (Akzo Nobel, Bridgewater, N.J.) was mixed with a solution (30 g) of 1% CMC in Water to form the aqueous phase. The oil phase was emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of HMDA (10.8 g, 70%). Formation of capsule was immediately visible by optical microscopy. The capsule slurry was transferred into a round bottom vessel and the capsule slurry was cured at 55° C. for 2 hours.

Sample 6-D: Polyurea Capsules Prepared with a Catalyst. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N3600 (Bayer corporation, Pittsburgh, Pa.) to form the oil phase. In a separate beaker, a solution (130 g) containing 1.85% FLEXAN II (Akzo Nobel, Bridgewater, N.J.) was mixed with a solution (30 g) of 1% CMC in Water to form the aqueous phase. The oil phase was emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of HMDA (10.8 g, 70%) and DABCO catalyst 0.30 g. Formation of capsule was immediately visible by optical microscopy. The capsule slurry was transferred into a round bottom vessel and the capsule slurry was cured at 55° C. for 2 hours.

Physical Characterization of Polyurea Capsules. SEM analysis of the capsules indicated that the capsules prepared with current invention had robust mechanical stability.

Encapsulation Performance of Polyurea Capsules. A fragrance capsule slurry (Sample 5-D) was diluted with distilled water to yield a mixture containing 0.2% capsule slurry. One gram of the diluted capsule slurry was directly applied to each side of a 4×6 fabric swatch. Two experiments were prepared. The swatches were air-dried overnight and the headspace of the fabrics was analyzed before and after stirring with stainless steel ball bearings to rupture intact capsules. The results are presented in Table 13.

TABLE 13

|  | Experiment 1 | | Experiment 2 | |
| --- | --- | --- | --- | --- |
|  | Unstirred | Stirred | Unstirred | Stirred |
| Headspace | 4608 | 34289 | 2600 | 88312 |
| Ratio Stirred/Unstirred | — | 7.44 | — | 34.0 |

This analysis indicated that there was a dramatic increase in headspace after the capsules were disrupted by milling. This demonstrated that increased perfumery perception can be achieved once the capsules are deposited on fabric and ruptured by physical forces.

Sensory Performance of Polyurea Capsules. To establish the consumer benefits of the polyurea capsules, the capsule slurry was blended into a roll-on base and evaluated for its consumer benefits. The fragrance load was 0.5% neat equivalent. For comparison, a similar solution was prepared using neat fragrance at 0.5%. The sample (0.3 g) was then applied to a blotter (4×6) and was allowed to dry overnight before being evaluated by a panel of 12 judges. The fragrance intensity was rated on a scale ranging from 0 to 10. A numerical value of 10 would suggest the subject generated a strong smell. The results are presented in Table 14.

TABLE 14

| Samples | Pre-rubbing intensity | Post-rubbing intensity | $I_{post, capsule}/I_{post, neat}$ |
|---|---|---|---|
| Neat | 1.5 | 2.8 | |
| Capsule Slurry | 0.5 | 5.7 | 2.03 |

This analysis indicated that the capsules had a much stronger fragrance intensity compared with neat fragrance in the post-rubbing stage and were able to deliver the full benefit of the fragrance formulation.

EXAMPLE 46

Preparation of Polyurea Capsule Composition

Preparation of the Fragrance Emulsion. Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, Desmodur® N100 (Bayer corporation, Pittsburgh, Pa., USA), to form the oil phase. In a separate beaker, an aqueous solution (120 g) containing 1.25% of FLEXAN II (Akzo Nobel, Bridgewater, N.J.) was mixed with a solution (30 g) of 1% CMC in water to form the aqueous phase. The oil phase was then emulsified into the aqueous phase to form the fragrance emulsion under shearing (ULTRA TURRAX, T25 Basic, IKA WERKE) at 12500 rpm for two minutes.

Formation of Fragrance Capsules. The fragrance emulsion was heated to 35° C. in a round bottom vessel before drop-wise addition of arginine monohydrochloride (20.1 g, 32%) and DABCO (0.3 g) under constant mixing with an overhead mixer. Formation of capsules was immediately visible by optical microscopy. The mixer speed was reduced after the addition of arginine monohydrochloride was complete. The capsule slurry was cured at 55° C. for two hours.

EXAMPLE 47

Preparation of Polyurea Capsule with High Shearing Speed

Preparation of the Fragrance Emulsion. Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, Desmodur® N100 (Bayer corporation, Pittsburgh, Pa., USA), to form the oil phase. In a separate beaker, an aqueous solution (120 g) containing 1.25% of FLEXAN II (Akzo Nobel, Bridgewater, N.J.) was mixed with a solution (30 g) of 1% CMC in Water to form the aqueous phase. The oil phase was then emulsified into the aqueous phase to form the fragrance emulsion under shearing (ULTRA TURRAX, T25 Basic, IKA WERKE) at 9500 rpm for two minutes.

Formation of Fragrance Capsules. The fragrance emulsion was heated to 35° C. in a round bottom vessel before drop-wise addition of arginine monohydrochloride (20.1 g, 32%) and DABCO (0.3 g) under constant mixing with an overhead mixer. Formation of capsules was immediately visible by optical microscopy. The mixer speed was reduced after the addition of arginine monohydrochloride was complete. The capsule slurry was cured at 55° C. for two hours.

EXAMPLE 48

Preparation of Cured Polyurea Capsule Cured at Elevated Temperature

Preparation of the Fragrance Emulsion. Ninety-six grams of a fragrance, Greenfields (International Flavors and Fragrance, Union Beach, N.J.) was weighed out and combined with 24 g of NEOBEE oil (Stepan, Chicago, Ill.) and 9.6 g of isocyanate monomer, Desmodur® N100 (Bayer corporation, Pittsburgh, Pa., USA), to form the oil phase. In a separate beaker, an aqueous solution (120 g) containing 1.25% of FLEXAN II (Akzo Nobel, Bridgewater, N.J.) was mixed with a solution (30 g) of 1% CMC in Water to form the aqueous phase. The oil phase was then emulsified into the aqueous phase to form the fragrance emulsion under shearing (ULTRA TURRAX, T25 Basic, IKA WERKE) at 12500 rpm for two minutes.

Formation of Fragrance Capsules. The fragrance emulsion was heated to 35° C. in a round bottom vessel before drop-wise addition of arginine monohydrochloride (20.1 g, 32%) and DABCO (0.3 g) under constant mixing with an overhead mixer. Formation of capsules was immediately visible by optical microscopy. The mixer speed was reduced after the addition of arginine monohydrochloride was complete. The temperature was raised 75° C. and then kept at 75° C. for 2 hours.

EXAMPLE 49

Preparation of Polyurea Capsule with More Isocyanate Precursors and Amine Crosslinkers Preparation of the Fragrance Emulsion. Ninety-six grains of a fragrance, Greenfields (International Flavors and Fragrance, Union Beach, N.J.) was weighed out and combined with 24 g of NEOBEE oil (Stepan, Chicago, Ill.) and 14.4 g of isocyanate monomer, Desmodur® N100 (Bayer corporation, Pittsburgh, Pa., USA), to form the oil phase. In a separate beaker, an aqueous solution (115.2 g) containing 1.3% of FLEXAN II (Akzo Nobel, Bridgewater, N.J.) was mixed with a solution (30 g) of 1% CMC in Water to form the aqueous phase. The oil phase was then emulsified into the aqueous phase to form the fragrance emulsion under shearing (ULTRA TURRAX, T25 Basic, IKA WERKE) at 12500 rpm for two minutes.

Formation of Fragrance Capsules. The fragrance emulsion was heated to 35° C. in a round bottom vessel before drop-wise addition of arginine monohydrochloride (20 g, 48%) and DABCO (0.4 g) under constant mixing with an overhead mixer. Formation of capsules was immediately visible by optical microscopy. The mixer speed was reduced after the addition of arginine monohydrochloride was complete. The temperature was raised 55° C. and then kept at 55° C. for 2 hours.

EXAMPLE 50

Preparation of Polyurea Capsule with More Isocyanate Precursors and Amine Crosslinkers Preparation of the Fragrance Emulsion. Ninety-six grams of a fragrance, Greenfields (International Flavors and Fragrance, Union Beach, N.J.) was weighed out and combined with 24 g of NEOBEE oil (Stepan, Chicago, Ill.) and 19.2 g of isocyanate monomer, Desmodur® N100 (Bayer corporation, Pittsburgh, Pa., USA), to form the oil phase. In a separate beaker, an aqueous solution (115.2 g) containing 1.36% of FLEXAN II (Akzo Nobel, Bridgewater, N.J.) was mixed with a solution (30 g) of 1% CMC in Water to form the aqueous phase. The oil phase was then emulsified into the aqueous phase to form the fragrance emulsion under shearing (ULTRA TURRAX, T25 Basic, IKA WERKE) at 12500 rpm for two minutes.

Formation of Fragrance Capsules. The fragrance emulsion was heated to 35° C. in a round bottom vessel before drop-wise addition of arginine monohydrochloride (19.8 g, 64%) and DABCO (0.6 g) under constant mixing with an overhead mixer. Formation of capsules was immediately visible by optical microscopy. The mixer speed was reduced after the addition of arginine monohydrochloride was complete. The temperature was raised 55° C. and then kept at 55° C. for 2 hours.

EXAMPLE 51

Preparation of Polyurea Capsule Slurry with Improved Stability

To improve stability, twenty-six grams of the capsule slurry as prepared in Example 46 was weighed out and 4 g of POLYQUATERNIUM-11 (PQ11, Vinyl pyrrolidone/dimethylaminoethyl methacrylate copolymer, cationic polymer, LUVIQUAT PQ11 AT 1, BASF, Ludwigshafen, Germany) was added. The mixture was stirred for approximately 30 minutes via an overhead IIIA lab mixer until the surfactant was completely dissolved and homogeneous.

Alternatively, a 10% solution of POLYQUATERNIUM-11 was prepared by dissolving 20 grams of the LUVIQUAT PQ11 AT 1 in 20 grams of water. The stabilized capsule slurry was prepared by mixing 7.5 grams of the fragrance capsule slurry prepared as in Example 46 with 22.5 grams of the 5% solution of POLYQUATERNIUM-11 under consistent mixing for 30 minutes.

EXAMPLE 52

Preparation of Polyurea Capsules Incorporating Surfactants and Polymers as Adjuvants To evaluate other adjuvants, polyurea capsule slurries were prepared as described in Example 46 and combined with one or more adjuvants as listed in Table 15. A general procedure for preparing the formulations is provided using Polyquaternium-6 as an example. A 10% Polyquaternium-6 solution was prepared by adding water to a 40% Polyquaternium-6 solution commercially available from Nalco. The diluted polymer solution was then mixed with the polyurea capsule slurry to give polyurea capsules with the appropriate level of adjuvant. The mixture was homogenized using an overhead misted at 500 rpm for 30 minutes before being placed in oven for storage tests.

TABLE 15

| Capsule adjuvant | Components of Adjuvant |
| --- | --- |
| CA106 | Poly(diallyldimethyl ammonium chloride), cationic polymer |
| CA111 | Vinyl pyrrolidone/dimethylaminoethyl methacrylate copolymer, cationic polymer |
| CA201 | Branched polyethyleneimine |
| CA202 | Polyvinylamine |

TABLE 15-continued

| Capsule adjuvant | Components of Adjuvant |
| --- | --- |
| CA301 | Polyvinylpyrrolidone, non-ionic polymer |
| CA401 | Poly(acrylic acid, sodium salt) |

EXAMPLE 53

Physical Characterizations of Polyurea Capsules

A scanning electron microscopic picture was taken for the capsules prepared in Example 46. The picture showed that the capsules prepared with current invention has robust mechanical stability.

EXAMPLE 54

Fragrance Loading Capacity from Polyurea Capsules

The capsule compositions prepared in Examples 46 and 47 were used to evaluate their fragrance loading capacities. The content of free fragrance in the slurries and the average particle size of capsules were analyzed following known procedures. The results are shown in Table 16.

TABLE 16

| Sample | FO (%) | Average particle size (μm) |
| --- | --- | --- |
| Example 46 | 0.2 | 6.6 |
| Example 47 | 0.1 | 163.6 |

EXAMPLE 55

Encapsulation Performance of Polyurea Capsules

The capsule composition prepared in Example 46 was blended into a model hair conditioner solution. The fragrance load was 0.5% neat equivalent. For comparison, similar solutions were prepared with neat fragrance at 0.5%. The perfumery benefit of the capsules was evaluated by conducting a hair wash experiment using accepted experimental protocols. Hairs were washed and then air-dried overnight before being evaluated by a panel of 12 judges. The fragrance intensity is rated from a scale ranging from 0 to 10. A numerical value of 2 would suggest the hair only produce weak intensity while a value of 10 would indicate a very strong smell.

Hairs treated with the capsule composition prepared in Example 46 showed a fragrance intensity of 4.5 post-brush and an intensity of 2 pre-brush. By contrast, Hairs treated with the neat fragrance showed an intensity of only 3 post-brush and an intensity of only 1 pre-brush.

EXAMPLE 56

Performance Investigation of Polyurea Capsule Slurries with Polymer Adjuvants in EU Liquid Detergent Base To evaluate the performance of the polyurea capsule compositions, the capsule slurries prepared in Examples 51 and 52 were blended into a model European liquid detergent solution to prepare five capsule formulations, i.e., (i) capsules and 2.5% CA111, (ii) capsules and 2.5% CA202, (iii) capsules, 1% CA111 and 1.5% CA202, (iv) capsules, 1.5% CA301, and 1% CA202, and (v) capsules and 2.5% CA201. The fragrance load was 0.5% neat equivalent. A comparative capsule formulation was prepared using capsules without any adjuvant at 0.5% fragrance neat equivalent. The perfumery benefit of the capsules was evaluated by conducting a laundry experiment using accepted experimental protocols with a European wash machine. Terry towels were washed and then air-dried overnight before being evaluated by a panel of 12 judges. The fragrance intensity is rated from a LMS scale ranging from 0 to 10. A numerical value of 2 would suggest the fabric only produce weak intensity while a value of 10 would indicate a very strong smell. The five capsule formulations with adjuvants each showed a fragrance intensity higher than that of the comparative capsule formulation. More specifically, the fragrance intensity of formulation (i) was 4 and that of the comparative was only 2.2, both measured at the post-rub stage.

EXAMPLE 57

Performance of Polyurea Capsule Slurries with Polymer Adjuvants in EU Fabric Conditioner Base To evaluate their performance, the capsule compositions prepared in Example 51 and 52 were blended into a model European fabric conditioner solution to obtain two formulations: one with 2.5% CA111 and the other with 2.5% CA202. A comparative formulation was prepared using capsules without any adjuvants. The perfumery benefit of the capsules was evaluated by conducting a laundry experiment using accepted experimental protocols with a European wash machine. Terry towels were washed and then air-dried overnight before being evaluated by a panel of 12 judges. The results showed that the two capsule formulations showed a fragrance intensity of 3.7 and 3.4 and the comparative formulation had a fragrance intensity of 3.1.

EXAMPLE 58

Performance Investigation of Polyurea Capsule Slurries with Polymer Adjuvants in Hair Conditioner Base To evaluate their performance, the capsule compositions prepared in Examples 51 and 52 were blended into a model hair conditioner solution. The fragrance load was 0.5% neat equivalent. Two capsule formulations were prepared: one with 2.5% CA202 and the other with 1% CA111 and 1.5% CA202. Two comparative formulations were prepared, one using hydrogel capsules described in patent WO2014011860A2 and the other using polyurea capsules without any adjuvant. In both comparative formulations, the fragrance load was at 0.5% neat equivalent. Each formulation was aged 4 weeks at 37° C. The perfumery benefit of the capsules was evaluated by conducting a hair wash experiment using accepted experimental protocols. Hairs were washed and then air-dried overnight before being evaluated by a panel of 12 judges. The fragrance intensity is rated from a scale ranging from 0 to 10. Unexpectedly, the two capsule formulations had a fragrance intensity of 6.8 and 6.3, post-brush. By contrast, the two comparative formulations had a fragrance intensity of 3.1.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Indeed, to achieve the purpose of encapsulating an active material, one skilled in the art can design and prepare a capsule composition by using different polyisocyanates, cross-linking agents, and/or capsule formation aids, varying the concentrations of these wall-forming materials and/or catalysts to achieve desirable organoleptic or release profiles in a consumable product. Further, the ratios among polyisocyanates, cross-linking agents, capsule forming aids, adjuvents, core modifiers, active materials, and catalysts can also be determined by a skilled artisan through assays known in the art to prepare capsule compositions with desirable properties.

From the above description, a skilled artisan can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A polyurea capsule composition comprising a plurality of capsules and a capsule formation aid, wherein each of the capsules contains a polyurea wall and an oil core, the polyurea wall is formed of a reaction product of a polyisocyanate and a cross-linking agent in the presence of the capsule formation aid, the cross-linking agent contains a branched polyethylenimine at a level of 0.1% to 5%, the polyisocyanate is a trimethylol propane-adduct of toluene diisocyanate, and a trimethylol propane-adduct of xylylene diisocyanate, or a combination of thereof and is present at a level of 0.1% to 10%, the oil core contains a fragrance at a level of 0.5% to 80%, and all percentages are based on the weight of the polyurea capsule composition.

2. The polyurea capsule composition of claim 1, wherein the branched polyethylenimine has a molecular weight of 200 to 2,000,000 Da.

3. The polyurea capsule composition of claim 1, wherein the capsule formation aid is (i) a mixture of carboxymethyl cellulose and polystyrene sulfonate, or (ii) a mixture of carboxymethyl cellulose and polyvinylpyrrolidone, carboxymethyl cellulose is present at a level of 0.1% to 5%, sulfonated polystyrene when present is at a level of 0.1% to 5%, and polyvinylpyrrolidone when present is at a level of 0.1% to 5%.

4. The polyurea capsule composition of claim 1, wherein the oil core further contains a malodor counteracting agent or a core modifier.

5. The polyurea capsule composition of claim 1, further comprising a deposition aid that is an anionic, cationic, nonionic, or zwitterionic polymer.

6. A method of preparing a polyurea capsule composition of claim 1 comprising:
   (a) preparing an oil phase comprising an active material and a polyisocyanate;
   (b) preparing a dispersant solution containing a capsule formation aid;
   (c) emulsifying the oil phase into the dispersant solution to form an active emulsion;

(d) adding a cross-linking agent to the active emulsion to form a capsule slurry; and (e) curing the capsule slurry, thereby obtaining a polyurea capsule composition, wherein the capsule composition has a plurality of capsules and the capsule formation aid; each of the capsules contains a polyurea wall and an oil core; the polyurea wall is formed of a reaction product of the polyisocyanate and the cross-linking agent in the presence of the capsule formation aid; the polyisocyanate is a trimethylol propane-adduct of toluene diisocyanate, a trimethylol propane-adduct of xylylene diisocyanate, or a combination thereof and is present at a level of 0.1 to 10%; the oil core contains a fragrance at a level of 0.5 to 80%; and the cross-linking agent contains a branched polyethylenimine at a level of 0.1 to 5%; the capsule formation aid is (i) a mixture of carboxymethyl cellulose and sulfonated polystyrene or (ii) a mixture of carboxymethyl cellulose and polyvinylpyrrolidone; carboxyrnethyl cellulose is present at a level of 0.1% to 5%; sultonated polystyrene when used is present at a level of 0.1% to 5%, polyvinylpyrrolidone when used is present at a level of 0.1% to 5%; and all percentages are based on the weight of the polyurea capsule composition.

7. The method of claim 6, further comprising adding a base or a catalyst into the active emulsion, wherein the base is a metal carbonate, metal bicarbonate, metal hydroxide, or combination thereof; and the catalyst is capable of increasing the rate of the reaction between the polyisocyanate and the cross-linking agent.

8. The method of claim 6, wherein the capsule slurry is cured at 55° C. to 135° C.

9. The method of claim 6, further comprising purifying the cured capsule slurry by diafiltration, centrifugation, or washing with water until a neutral pH is achieved.

10. The method of claim 9, further comprising adding a salt to the cured capsule slurry before washing the capsule slurry with water.

11. A polyurea capsule composition prepared by the method of claim 6.

12. A consumer product comprising the capsule composition of claim 1.

13. A consumer product comprising the capsule composition of claim 11.

14. The consumer product of claim 12, wherein the consumer product is a shampoo, a hair conditioner, a soap, a body wash, a cosmetic preparation, a body liquid detergent, an all-purpose cleaner, a fabric softener or refresher, an ironing water, a fabric detergent, a softener, a drier sheet, a fine fragrance, an Eau De Toilette product, a deodorant, an roll-on product, or an aerosol product.

* * * * *